United States Patent
Nishi et al.

(10) Patent No.: US 11,744,484 B2
(45) Date of Patent: Sep. 5, 2023

(54) BEHAVIOR ESTIMATING METHOD, BEHAVIOR ESTIMATING SYSTEM, SERVICE PROVIDING METHOD, SIGNAL DETECTING METHOD, SIGNAL DETECTING UNIT, AND SIGNAL PROCESSING SYSTEM

(71) Applicants: KABUSHIKI KAISHA TOSHIBA, Minato-ku (JP); Toshiba Digital Solutions Corporation, Kawasaki (JP)

(72) Inventors: Kazuyoshi Nishi, Suginami (JP); Yasuyoshi Hyodo, Ota (JP); Taisuke Yamanaka, Shinjuku (JP)

(73) Assignees: Kabushiki Kaisha Toshiba, Tokyo (JP); Toshiba Digital Solutions Corporation, Kawasaki (JP)

( * ) Notice: Subject to any disclaimer, the term of this patent is extended or adjusted under 35 U.S.C. 154(b) by 1173 days.

(21) Appl. No.: 16/193,314

(22) Filed: Nov. 16, 2018

(65) Prior Publication Data
US 2019/0099115 A1    Apr. 4, 2019

Related U.S. Application Data

(63) Continuation of application No. PCT/JP2017/012758, filed on Mar. 28, 2017.

(30) Foreign Application Priority Data

May 18, 2016 (JP) ................................ 2016-100007

(51) Int. Cl.
*A61B 5/11* (2006.01)
*A61B 5/22* (2006.01)
(Continued)

(52) U.S. Cl.
CPC ............... *A61B 5/1118* (2013.01); *A61B 5/11* (2013.01); *A61B 5/1107* (2013.01);
(Continued)

(58) Field of Classification Search
None
See application file for complete search history.

(56) References Cited

U.S. PATENT DOCUMENTS 9,068,843 B1 * 6/2015 Sohn ..................... G06F 3/0346
2004/0267140 A1 12/2004 Ito et al.
(Continued)

FOREIGN PATENT DOCUMENTS

JP    2001-166230    6/2001
JP    2008-188442    8/2008
(Continued)

OTHER PUBLICATIONS

Müller, "Information Retrieval for Music and Motion", 2007, Springer-Verlag, pp. 69-84 (Year: 2007).*
(Continued)

*Primary Examiner* — Brent A. Fairbanks
(74) *Attorney, Agent, or Firm* — Maier & Maier, PLLC

(57) ABSTRACT

According to one embodiment, a behavior estimating method for estimating behavior of a person being measured equipped with an activity meter including an acceleration sensor, includes presetting a first angle between a gravitation direction and a direction of action of a standard person being measured, calculating different acceleration waveforms from the activity meter, extracting a second angle between the gravitation direction and the direction of action of the person from the acceleration waveforms, performing a coordinate transformation process among the acceleration waveforms based upon the present first angle and the extracted
(Continued)

second angle, and performing behavior estimation of the person using a result of the coordinate transformation.

6 Claims, 58 Drawing Sheets

(51) Int. Cl.
  *A61B 5/00* (2006.01)
  *B66B 5/00* (2006.01)
(52) U.S. Cl.
  CPC .......... *A61B 5/1121* (2013.01); *A61B 5/1123* (2013.01); *A61B 5/22* (2013.01); *A61B 5/7257* (2013.01); *B66B 5/0025* (2013.01); *A61B 2503/20* (2013.01); *A61B 2562/0219* (2013.01)

(56) References Cited

U.S. PATENT DOCUMENTS

| | | | | |
|---|---|---|---|---|
| 2005/0080590 | A1* | 4/2005 | Kawai | B25J 13/088 |
| | | | | 702/141 |
| 2006/0284979 | A1* | 12/2006 | Clarkson | A61B 5/1118 |
| | | | | 348/143 |
| 2009/0054111 | A1 | 2/2009 | Takizawa et al. | |
| 2010/0069203 | A1 | 3/2010 | Kawaguchi et al. | |
| 2013/0041619 | A1 | 2/2013 | Kasama et al. | |
| 2013/0081451 | A1* | 4/2013 | Kamada | G01M 1/122 |
| | | | | 177/136 |
| 2013/0116602 | A1* | 5/2013 | Van Den Heuvel | |
| | | | | A61B 5/1126 |
| | | | | 600/595 |
| 2013/0133968 | A1* | 5/2013 | Shirokura | B62K 1/00 |
| | | | | 180/220 |
| 2016/0169680 | A1* | 6/2016 | Lee | G01C 21/16 |
| | | | | 702/151 |
| 2018/0343024 | A1* | 11/2018 | Sahebjavaher | H04B 1/385 |

FOREIGN PATENT DOCUMENTS

| | | |
|---|---|---|
| JP | 2008-307207 | 12/2008 |
| JP | 2009-55137 | 3/2009 |
| JP | 2009-116389 | 5/2009 |
| JP | 2010-68968 | 4/2010 |
| JP | 2010-207488 | 9/2010 |
| JP | 2010-257395 | 11/2010 |
| JP | 2013-41376 | 2/2013 |
| JP | 5417779 | 2/2014 |

OTHER PUBLICATIONS

International Search Report dated Jun. 13, 2017 in PCT/JP2017/012758, filed on Mar. 28, 2017.
Written Opinion dated Jun. 13, 2017 in PCT/JP2017/012758, filed on Mar. 28, 2017.
Togashi, H. et al., "Orientation-independent method for simultaneous recognition of pedestrian motion type and motion direction using 9-axis sensor on smartphones", The Institute of Electronics, Information and Communication Engineers (IEICE) Technical Report, vol. 114, No. 356, Dec. 4, 2014, pp. 31-38 (with unedited computer generated English translation).

* cited by examiner

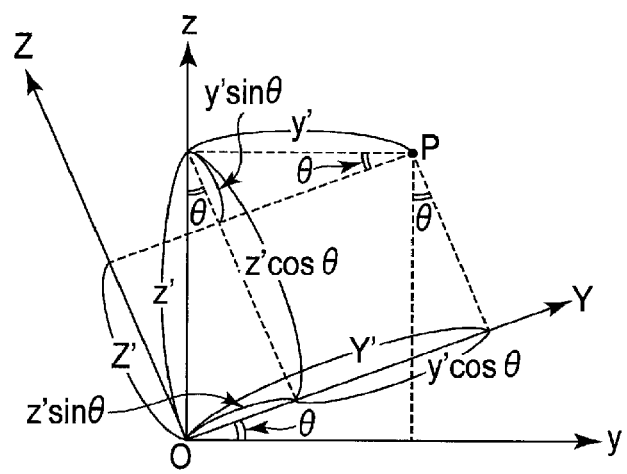
F I G. 4

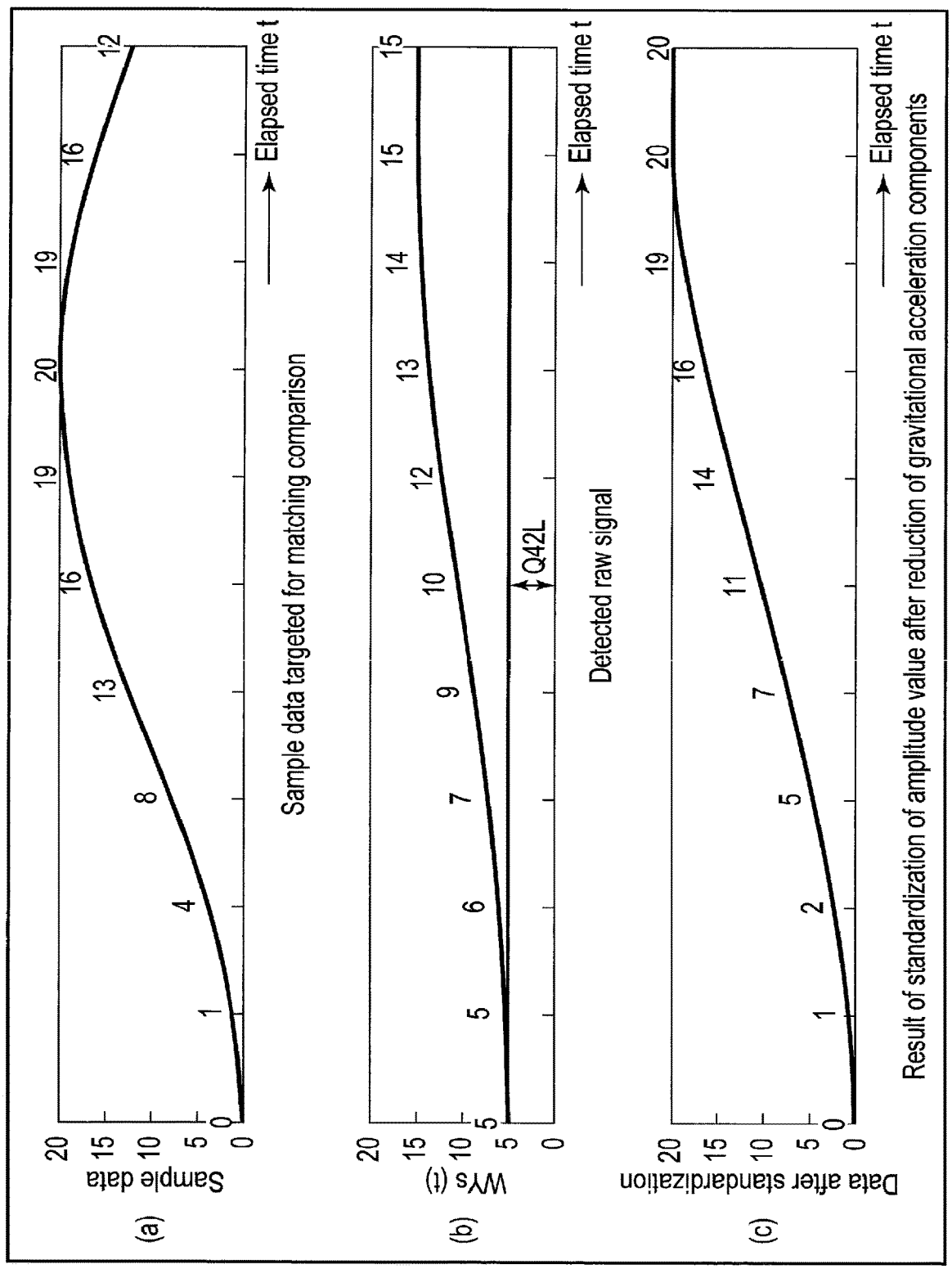
F I G. 18

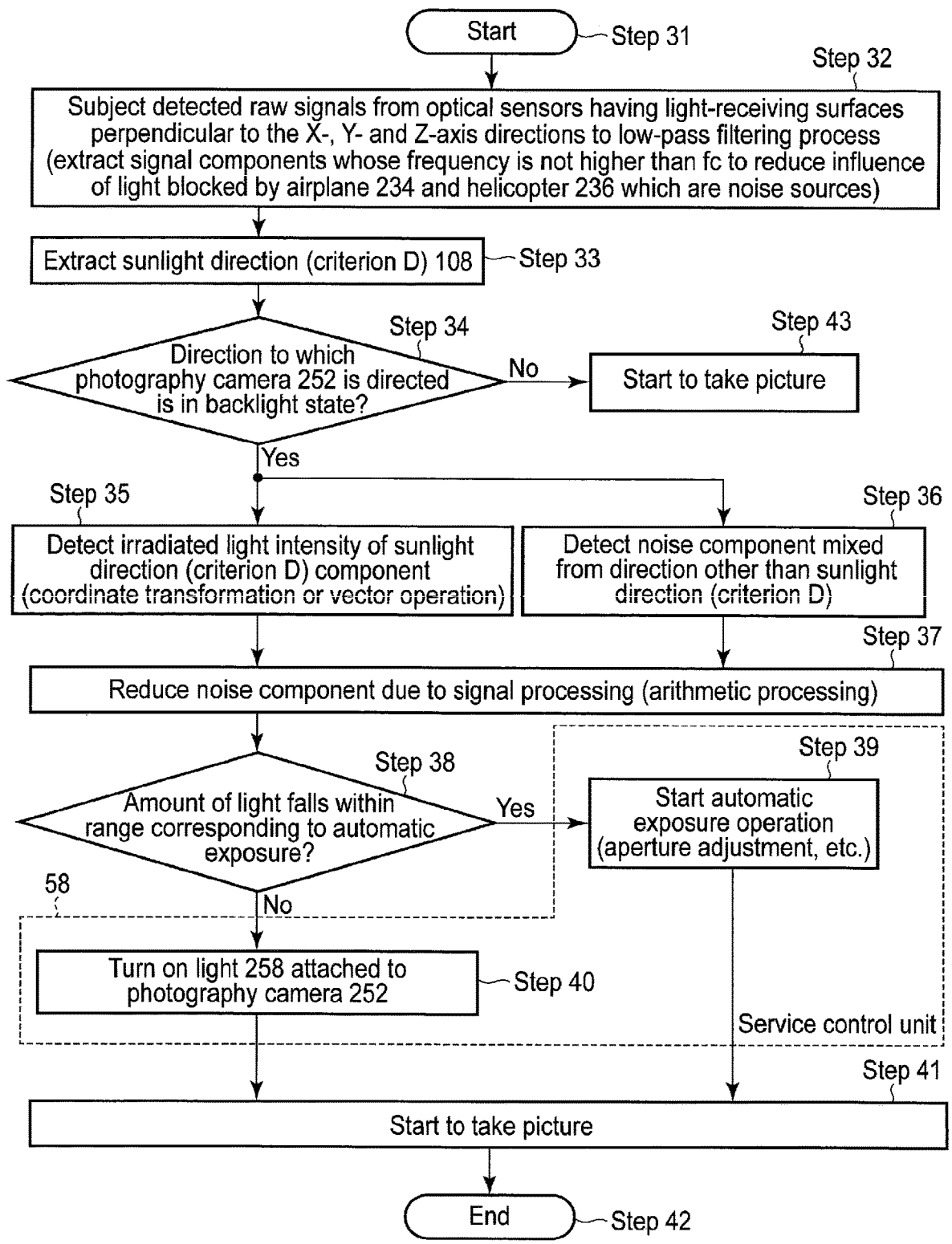
F I G. 31

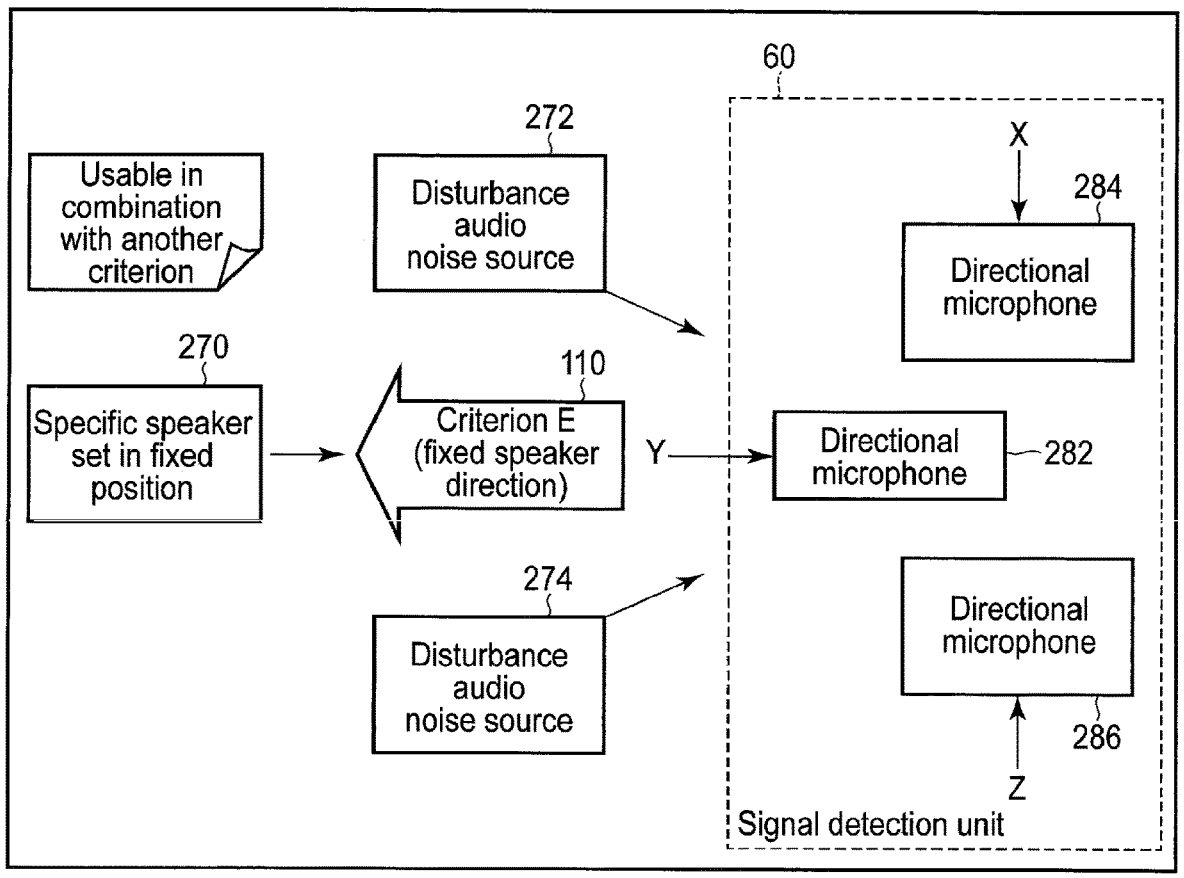
F I G. 32

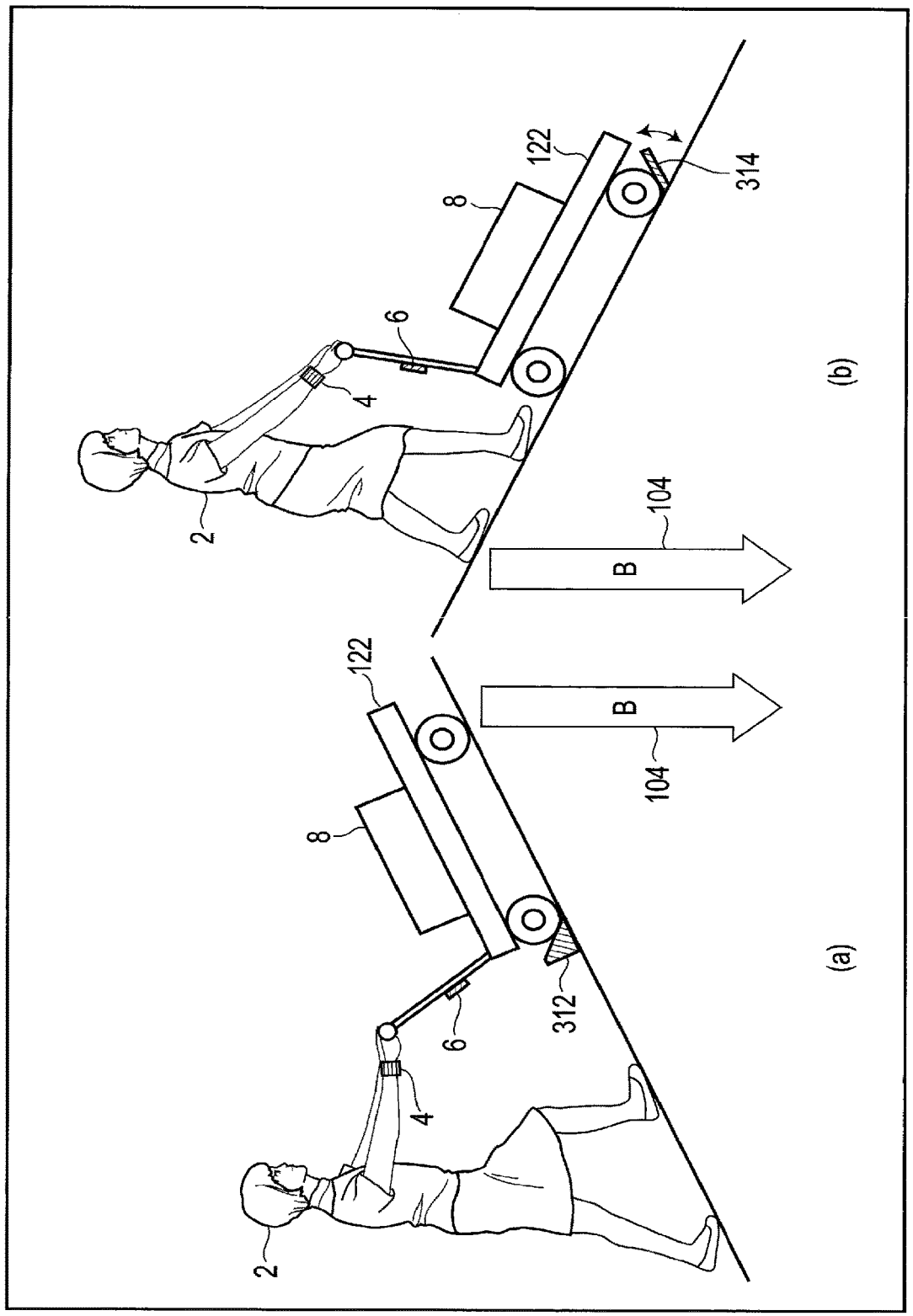
F I G. 36B

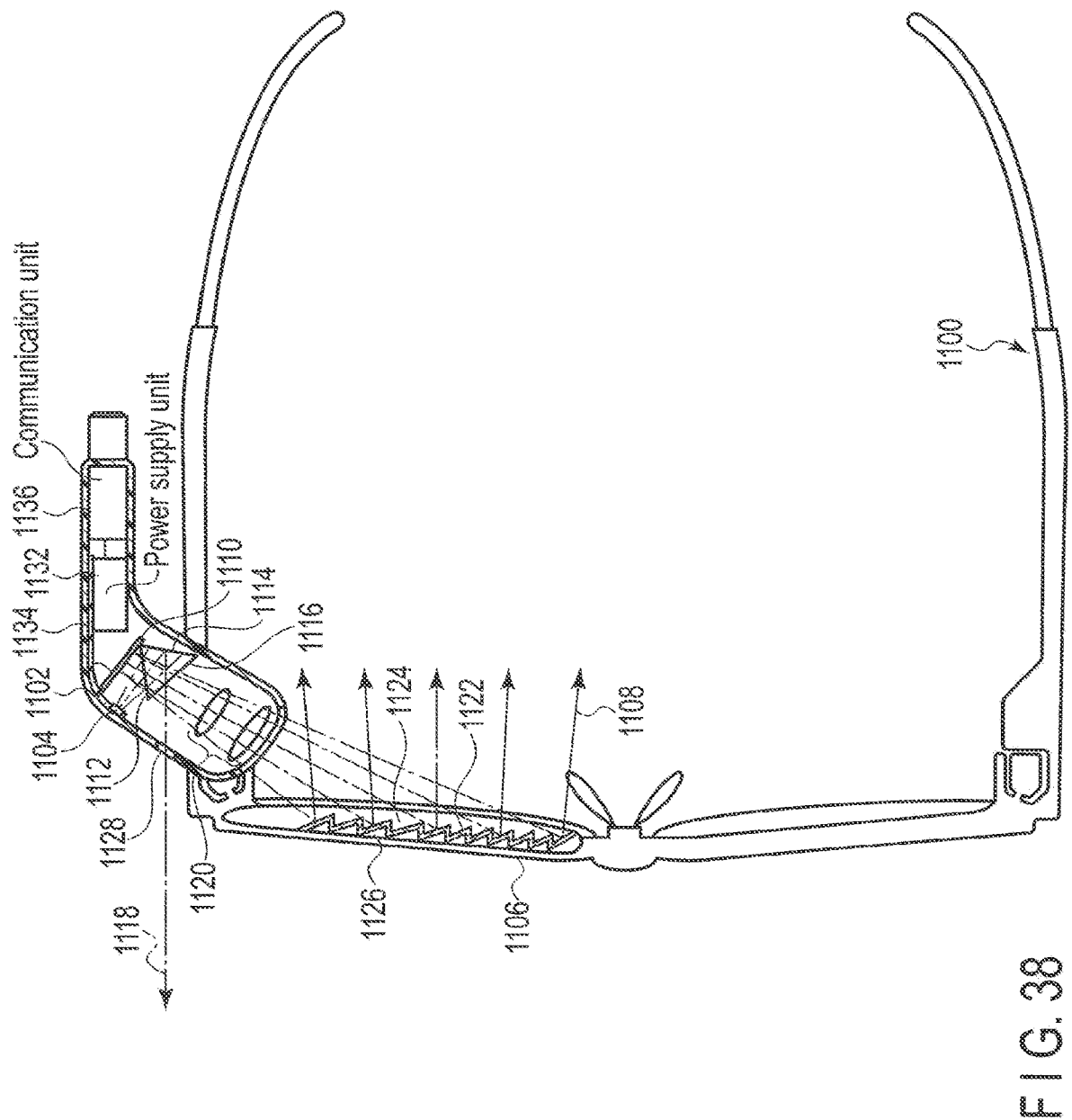
F I G. 38

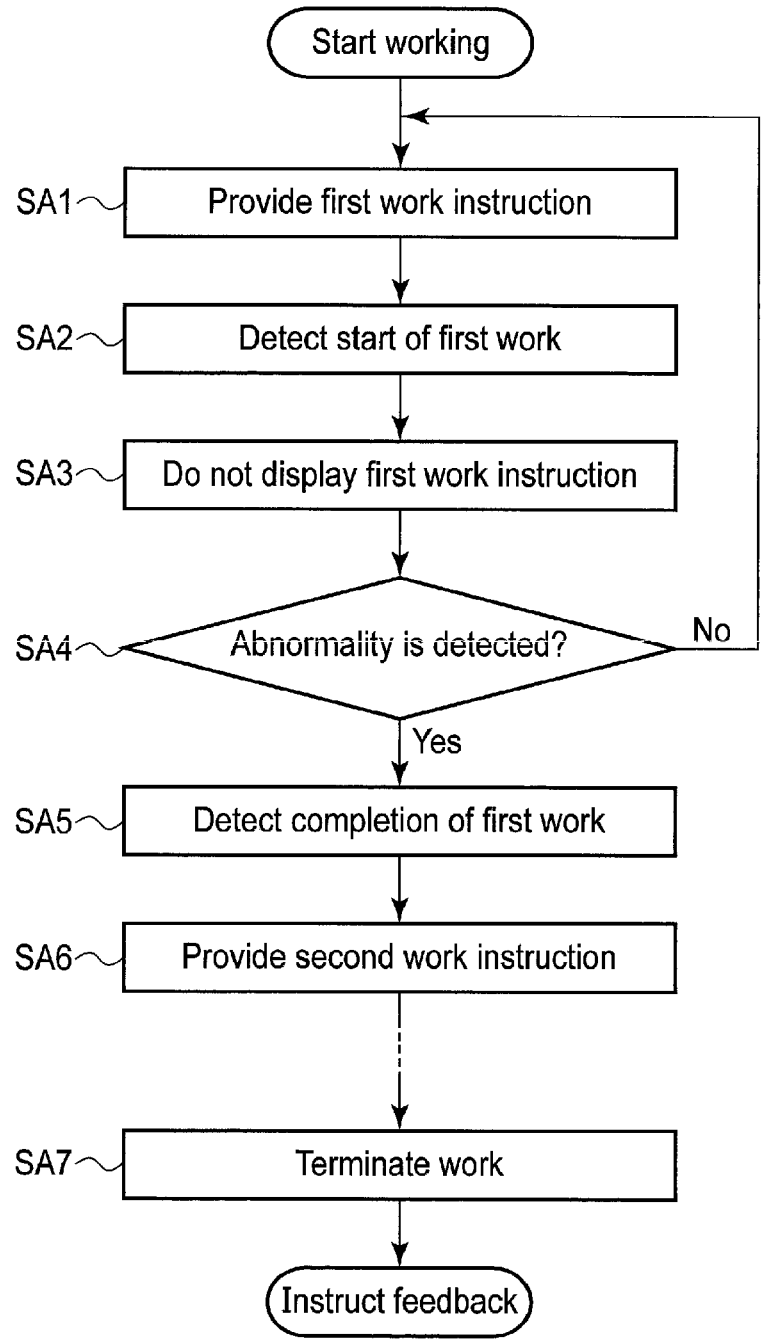
F I G. 39A

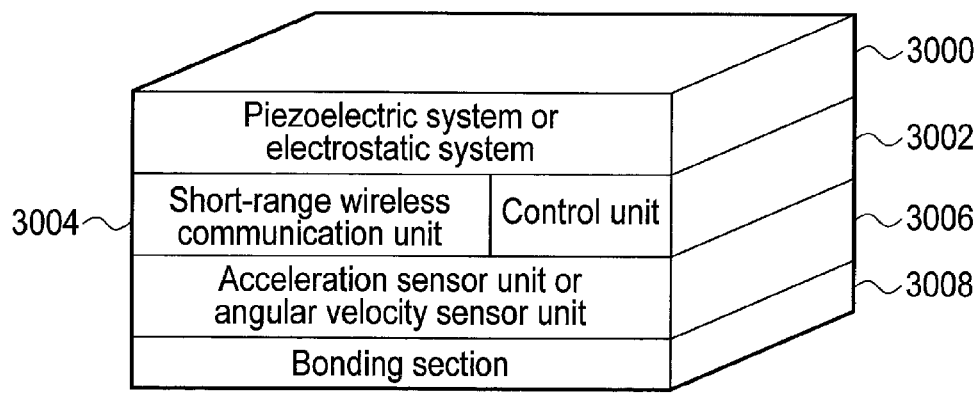
F I G. 41
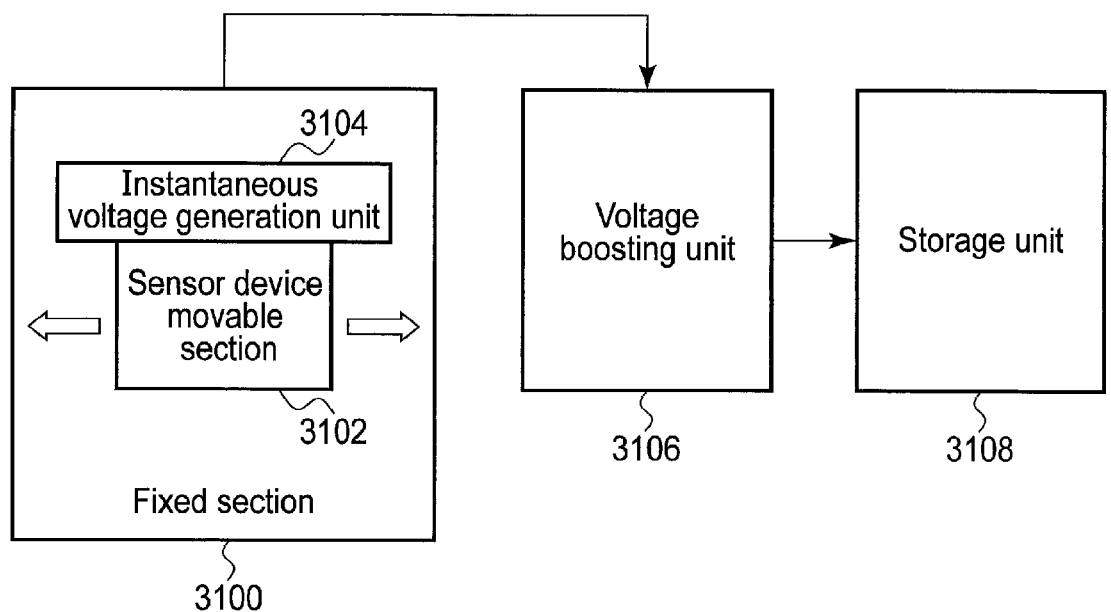
F I G. 42

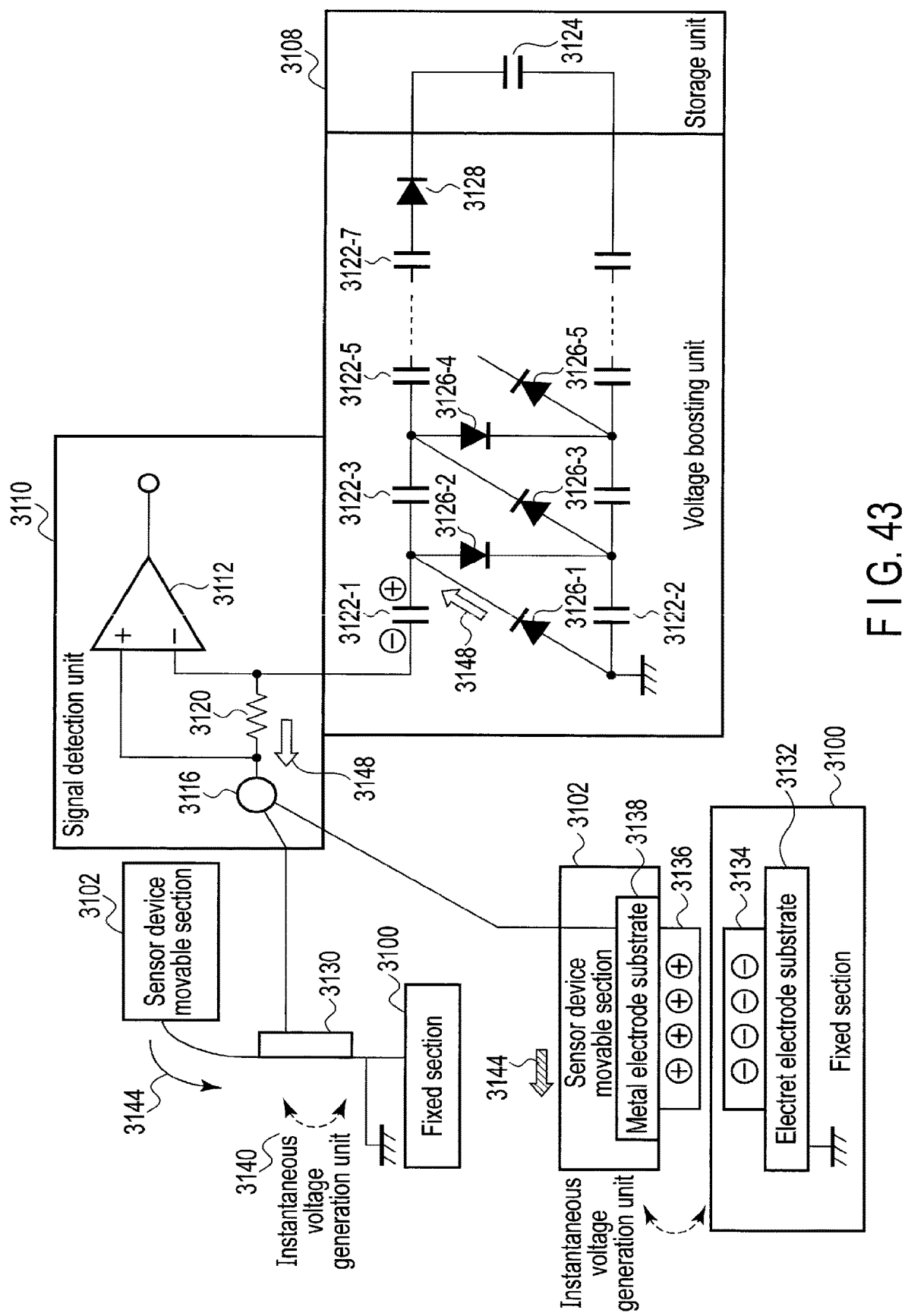
F I G. 43

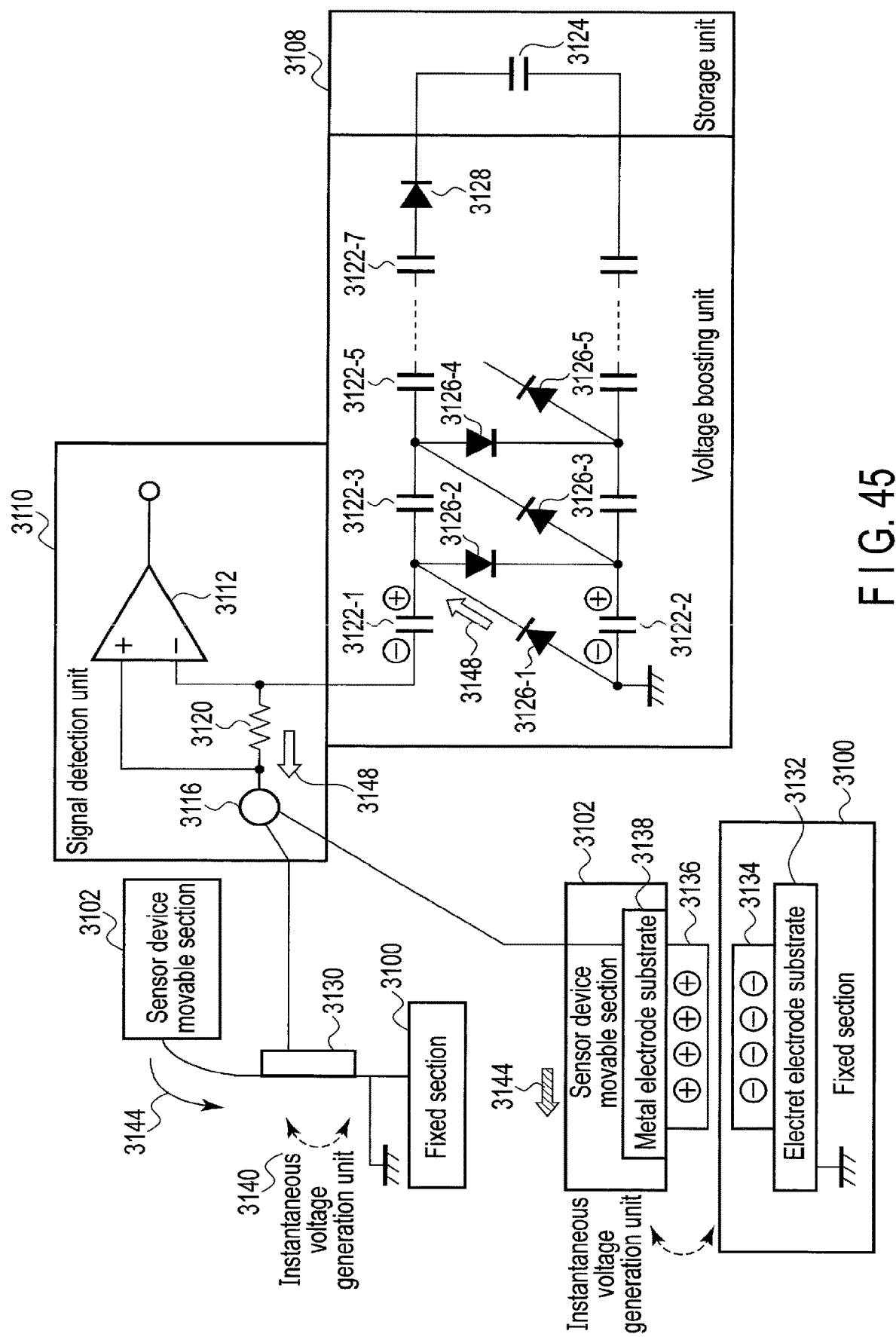
F I G. 45

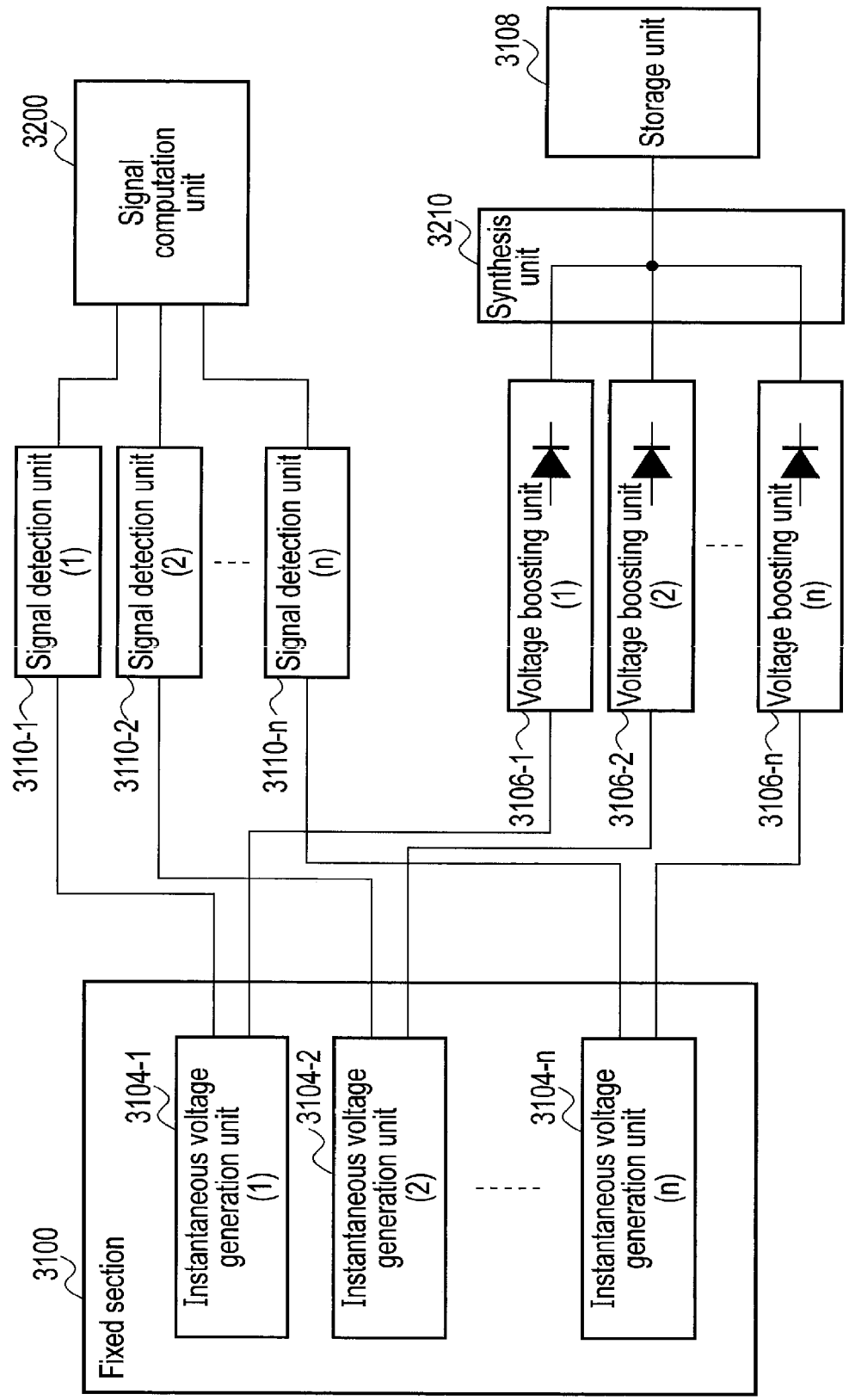
F I G. 48

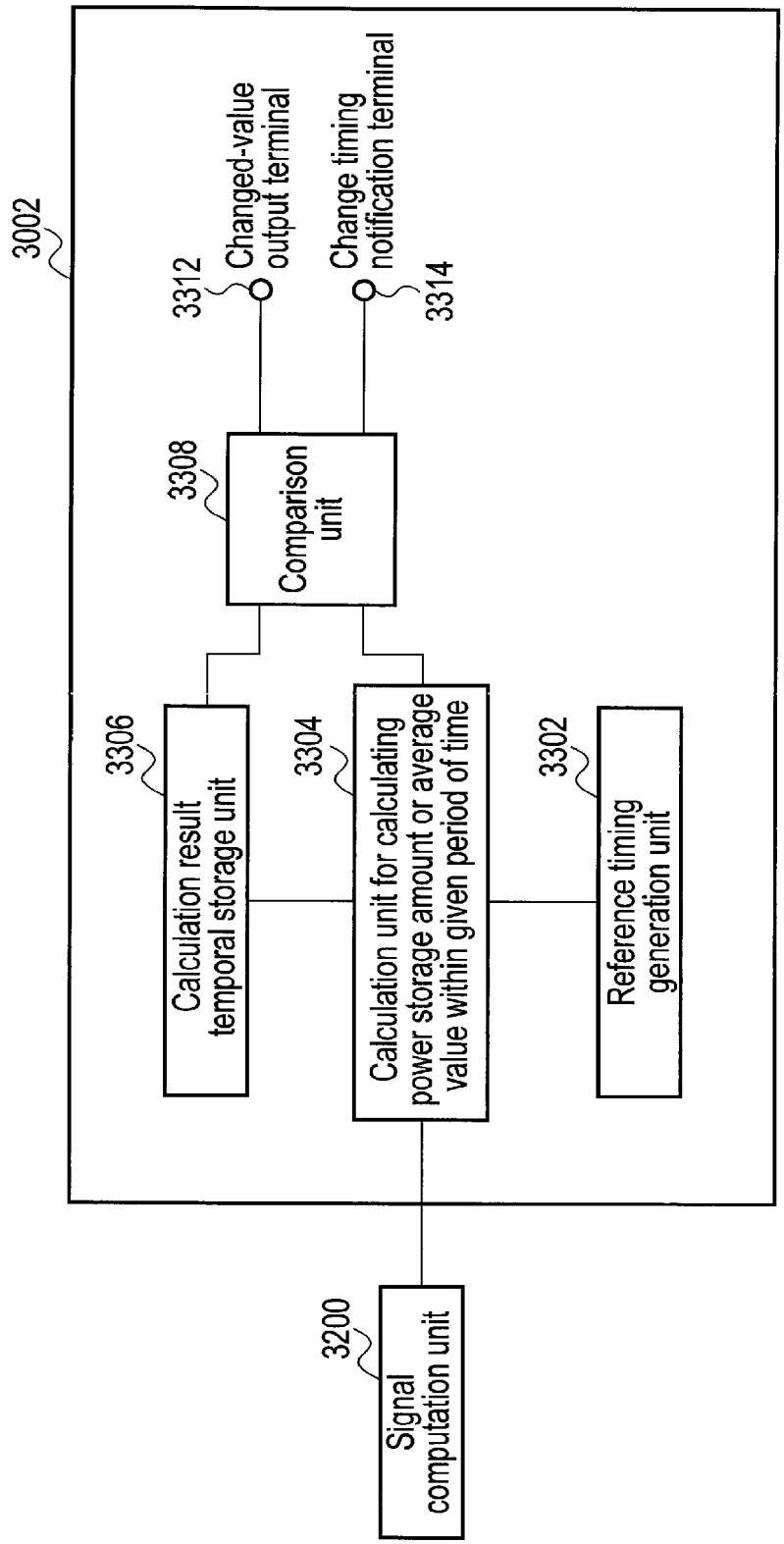
F I G. 51

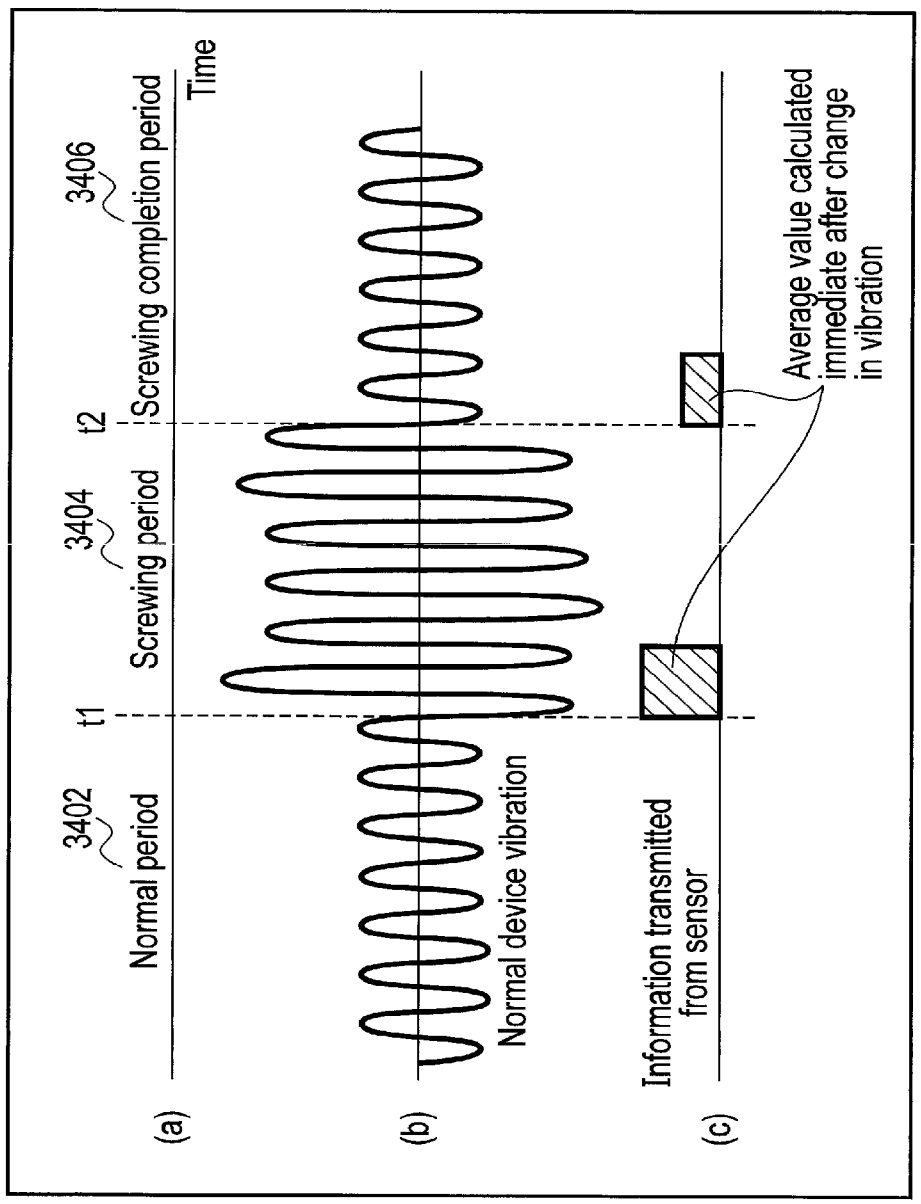
F I G. 52

BEHAVIOR ESTIMATING METHOD, BEHAVIOR ESTIMATING SYSTEM, SERVICE PROVIDING METHOD, SIGNAL DETECTING METHOD, SIGNAL DETECTING UNIT, AND SIGNAL PROCESSING SYSTEM

CROSS-REFERENCE TO RELATED APPLICATIONS

This application is a Continuation Application of PCT Application No. PCT/JP2017/012758, filed Mar. 28, 2017 and based upon and claiming the benefit of priority from Japanese Patent Application No. 2016-100007, filed May 18, 2016, the entire contents of all of which are incorporated herein by reference.

FIELD

Embodiments described herein relate generally to a behavior estimation technology using a signal detected from an activity meter attached to a person being measured.

However, the embodiments are not limited to the above technology, but include a detection technology of signals detected from a sensor, an estimation technology or a service providing technology using the detection technology.

BACKGROUND

In activity estimation using an activity meter, when workers who are persons being measured of the activity meter work using articles to be used outdoors, such as a device and equipment (e.g., dolly), working estimation accuracy may vary with differences in physical characteristics such as height among the workers.

Therefore, technologies to reduce variations in estimation accuracy among workers are required.

Disturbance noise components mixed into signals detected from a number of sensors as well as the activity meter also greatly affect detection environment and detection condition; consequently, the accuracy of detection using a sensor varies with the detection environment and detection condition.

On the other hand, individual optimization of a signal detecting method, which is performed for each detection environment or for each detection condition to reduce the variations in detection accuracy, has a harmful effect with significant complication.

Therefore, technologies capable of detecting a signal with small detection error by a simple method are required.

There is the conventional literature which discloses the technology relevant to the above-mentioned activity meter.

Conventionally, when workers moved dollies, correct waveform data of a detected signal used for activity estimation was prepared for each of the workers and activity estimation was done for each individual worker. It was therefore possible to reduce variations in estimation accuracy among workers. To obtain correct waveform data for each of the workers however needs labor and costs and greatly impairs convenience.

As a technology to remove disturbance noise components to be mixed into a signal detected from a common sensor as well as behavior estimation of workers who move dollies as described above, the conventional literature discloses removing low-frequency components of a signal detected from an acceleration sensor using a high-pass filter. However, when a worker wishes to detect a slow change, the components of the detected signal will be included in a low-frequency band. Therefore, this method incurs the risk of removing even the detected signal to the contrary.

When the acceleration sensor is attached to the worker's body, as a method of estimating whether the worker's behavior is "walking state" or "running state", the conventional literature discloses calculating the ratio between "magnitude of amplitude" and "cycle" of a signal detected from the acceleration sensor to discriminate between the walking and running states easily. However, even though such calculation is performed, estimation accuracy is still low in the detection environment where a number of disturbance noise components are mixed in the detected signal.

Therefore, even in the environment where disturbance noise components are mixed in the detected signal, it is desirable to ensure reliability of the signal detection.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 4 is an illustration of a coordinate transformation method among a plurality of detected signals.

FIG. 18 is an illustration of the relationship between sample data and pattern matching target data.

FIG. 31 is an illustration of an example of a processing flow regarding an application example using a photoelectric signal.

FIG. 32 is an illustration of an application example using a predetermined reference regarding an audio signal.

FIG. 36B is an illustration (2) of the method for mixing a disturbance signal into the extracted criterion.

FIG. 38 is an illustration of a configuration of a glasses-type wearable terminal (drive device).

FIG. 39A is a flowchart of an operation example of an application example of the system according to the present embodiment.

FIG. 41 is an illustration of a detailed configuration of a sensor device that detects and notifies a work completion state.

FIG. 42 is an illustration of a basic configuration of the interior of an environmental vibration power-generating device.

FIG. 43 is an illustration (1) of the principle of storage of the interior of the environmental vibration power-generating device.

FIG. 45 is an illustration (3) of the principle of storage of the interior of the environmental vibration power-generating device.

FIG. 48 is an illustration of another embodiment of a configuration of part of the interior of the sensor device.

FIG. 51 is an illustration of a method for detecting a value of the changed acceleration/angular velocity in the controller.

FIG. 52 is an illustration of vibration characteristics before and after a screwing operation.

DETAILED DESCRIPTION

Figure 1:
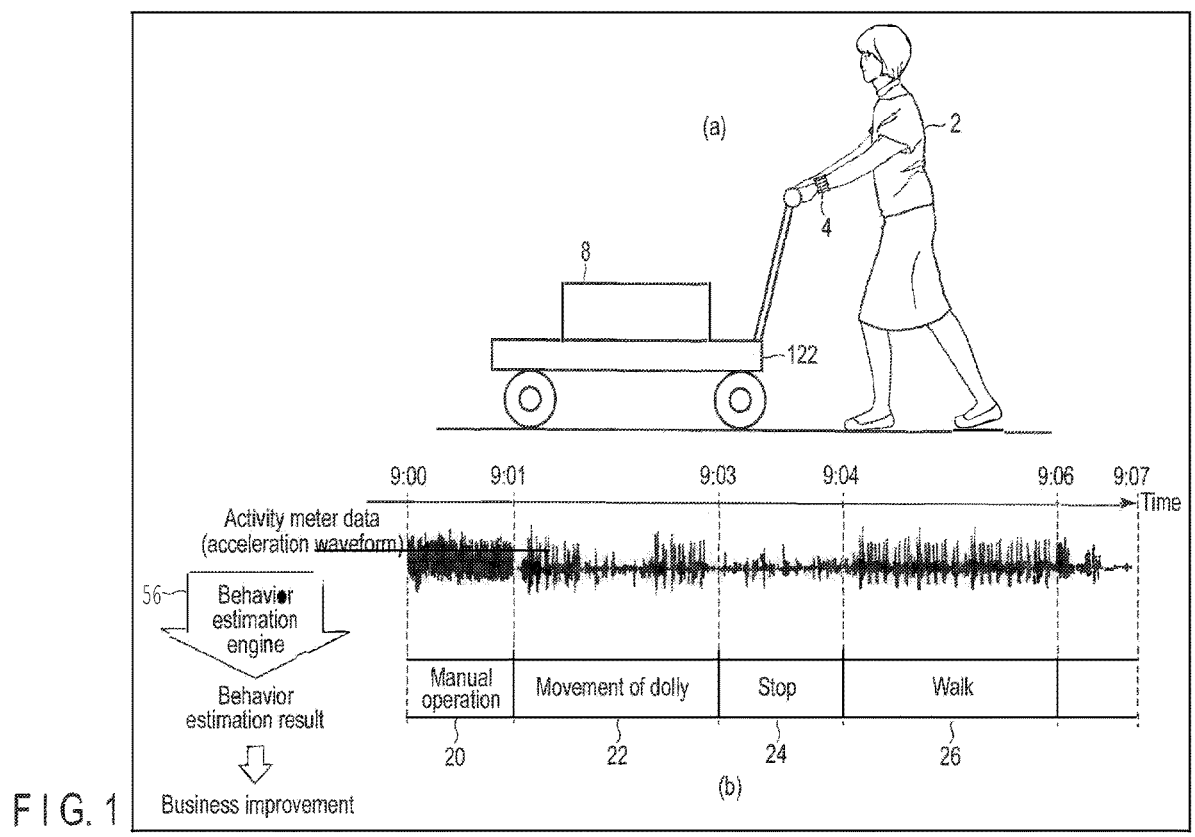
FIG. 1 is an illustration of an example of the present embodiment.

In the present embodiment, the coordinate system of measured acceleration is transformed into a coordinate system capable of estimating behavior of a worker (person being measured) using an angle between the arm of the worker and a dolly, extracted from the resolved gravity acceleration value. The behavior of the worker is estimated using the transformed detected signal. The behavior estimation is improved in accuracy by automatically correcting the conditions of the behavior estimation.

According to the present embodiment, coordinate transformation is performed for a plurality of detected signal waveforms using an angle between a reference direction such as a gravitation direction and a direction of action of the person being measured and based upon the result, the behavior of the person being measured is estimated or service is provided to the person being measured.

The direction of action can be adapted to a direction in which the person being measured pushes the dolly or an angle of the arms of the person being measured who holds the dolly.

As a result of the present embodiment, the accuracy of behavior estimation can be increasing without preparing or using correct waveform data corresponding to each worker whose behavior is to be estimated.

Various embodiments will be described hereinafter with reference to the accompanying drawings. In this specification, a sensor device attachable to the body of a person and capable of detecting an amount of activity of the person using a signal detected therefrom, will be referred to as an activity meter. As an example of a method for attaching the activity meter to the human body (person being measured 2), an activity meter (sensor device) 4 is shaped like a wristband and attached to the arm or leg of the person being measured 2 as shown in (a) of FIG. 1. In the example shown in (a) of FIG. 1, the person being measured 2 equipped with the activity meter 4 pushes a dolly 122, and behavior estimation as to whether "the person being measured 2 is moving 22 the dolly 122" is made from raw signals detected and collected from the activity meter 4. The activity meter is not limited to the wristband, but can be embedded in clothes and clothing such as hats, glasses and shoes. The basic contents of the present embodiment are to perform the following steps (1) to (6) (some of the steps can be omitted according to the circumstances):

(1) Detecting raw signals from the activity meter attached to the human body (or animal);
(2) Extracting a criterion from the detected raw signals;
(3) Processing the detected raw signals based on the extracted criterion;
(4) Estimating the behavior (or condition or demand) of the human body (or animal) based on a result of the signal processing;
(5) Analyzing the history of behavior for each person being measured (worker) (who is in business, working, etc.); and
(6) Improving business (improving a working process) based on a result of the analysis.

The embodiment is not limited to the above steps, but may include a step of (7) providing proper service using a result of the estimation obtained from steps (1) to (4). Furthermore, the system of the present embodiment is not limited to this step, but may include any application using the above result of the estimation.

Moreover, the present embodiment may include steps of fixing a sensor device to a given object (other than persons and animals), estimating a condition related to the given object based upon a signal detected from the sensor device and providing service based upon the result.

In FIG. 1, (b) shows variations in behavior of the person being measured 2 every elapsed time and variations in raw signals (acceleration waveforms) detected from the activity meter 4 during each behavior. Specifically, the person being measured 2:

performs manual operation 20 from 9:00 to 9:01;
moves the dolly from 9:01 to 9:03;
stops temporarily until 9:04; and
walks from 9:04 to 9:06.

In the above behavior, as shown in (b) of FIG. 1, a raw signal (acceleration waveform) proper (unique) to each behavior is detected from the activity meter 4.

Therefore, the behavior of the person being measured 2 can be estimated by extracting characteristics of the detected raw signals (acceleration waveforms) using a behavior estimation engine 56. In the present embodiment, the raw signals (acceleration waveforms) detected from the activity meter 4 are stored temporarily in a memory unit (output waveform data storage that stores waveform data output from a sensor) (corresponding to the above step (1)), and a series of steps of (2) criterion extraction, (3) signal processing, (4) behavior estimation, (5) history analysis and (6) business improvement 10 is performed using the detected raw signals (acceleration waveforms) read out of the memory unit (output waveform data storage unit).

The present embodiment is not limited to the above steps. The steps (2) to (6) can be performed in real time for the raw signals (acceleration waveforms) detected from the activity meter 4 in step (1). Furthermore, based upon a behavior estimation result 16, the step (7) (of providing proper service) can be performed.

As will be described later with reference to FIG. 3, three axes (X, Y and Z axes) which are orthogonal to one another are preset in the interior of a signal detection unit 60 of the activity meter 4 and a signal detection unit 60 of a sensor device 6. As the relationship between these axes and a predetermined criterion (e.g., a gravity direction along the z axis and a geomagnetism direction along the y axis), the direction from the arm 120 of the person being measured 2 equipped with the activity meter 4 toward the middle finger thereof is set as the Y axis, as will be described later with reference to FIG. 5, for example. Here, the action direction 100 in which the person being measured 2 pushes the dolly (the direction in which force is exerted by the person being measured 2) coincides with the Y-axis direction.

The axial direction perpendicular to the back of a hand of the person being measured is set as the Z-axis direction and the direction orthogonal to the Y and Z axes (direction from the little finger of the person being measured 2 toward the thumb thereof) is set as the X axis. In accordance with these coordinate axes, a three-axis acceleration sensor 72 outputs acceleration waveforms (detected raw signals WX(t), WY(t) and WZ(t)) in the X-axis direction, Y-axis direction and Z-axis direction.

At the same time, a three-axis geomagnetism sensor 74 outputs field intensity signals in the X-axis, Y-axis and Z-axis directions.

On the other hand, the direction along criterion A (geomagnetism direction) 102 is defined as the y axis (direction from the South Pole 114 to the North Pole 112). The direction from the west to the east is also defined as the x axis.

In most cases, the Y and y axes do not coincide with each other, and the waveforms of Wx(t) and Wy(t) are not directly detected as raw signals because the Y and y axes are inclined to each other. Based on these premises, the following explanation can be given.

The three-axis acceleration sensor 72 (FIG. 17) embedded in the activity meter 4 detects raw signals WX(t), WY(t) and WZ(t). The raw signal WZ(t)(or WY(t)) corresponds to activity meter data (acceleration waveform) 12 shown in FIG. 1.

Figure 17:
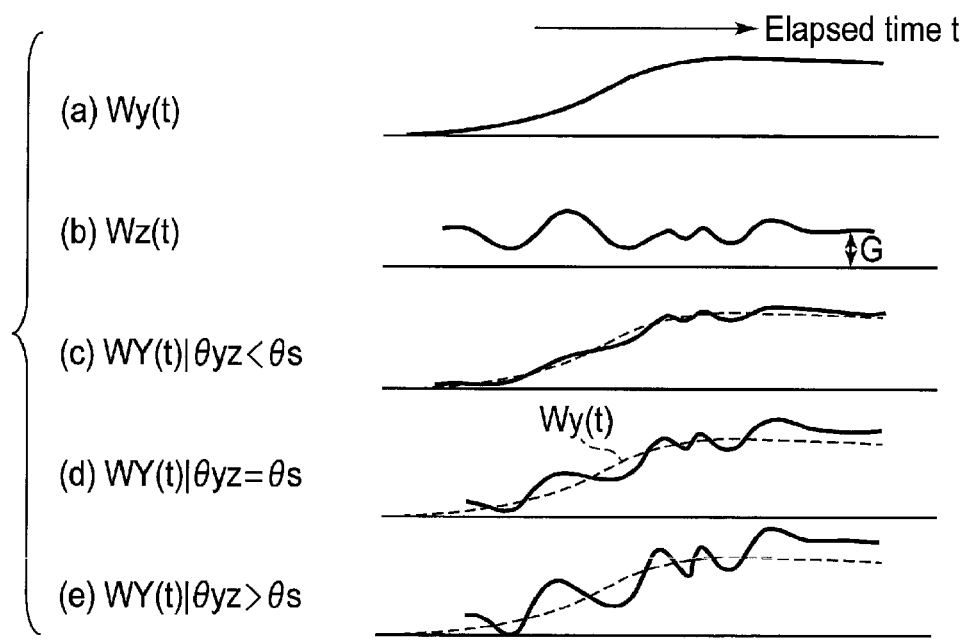
FIG. 17 is an illustration of the relationship between angle θyz of an arm of a person being measured and the detected raw signal waveform.

The detected raw signals WX(t), WY(t) and WZ(t) collected sequentially as time elapses are stored sequentially in a memory unit (output waveform data storage unit) 82 shown in FIG. 17. The detected raw signals WX(t), WY(t) and WZ(t) stored at once in the memory unit (output waveform data storage unit) 82 may data corresponding to continuous behavior of the person being measured 2 for two to three hours. Not only this data but also behavior data of the person being measured 2 for one day can be stored at once.

Figure 2:
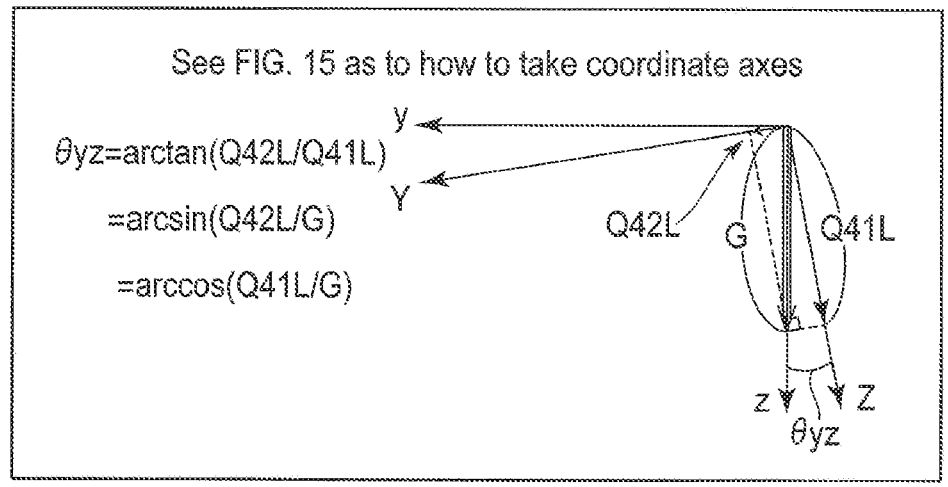
FIG. 2 is an illustration (1) of a method for extracting a predetermined criterion from detected raw signals.

FIG. 2 shows a method for extracting criterion B (geomagnetism direction) 104 using signal components Q41L and Q42L that have been subjected to a low-pass filtering process, which represent acceleration. There is the following relationship among low-frequency component Q42L of the raw signal WY(t) detected in the Y-axis direction, low-frequency component Q41L of the raw signal WZ(t) detected in the Z-axis direction and gravity acceleration component G in the z-axis direction.

$$\theta yz = \arctan(Q42L/Q41L) \quad \text{Equation (1)}$$

$$\theta yz = \arcsin(Q42L/G) \quad \text{Equation (2)}$$

$$\theta yz = \arccos(Q41L/G) \quad \text{Equation (3)}$$

Using one of the above equations (1), (2) and (3), angle θyz can be calculated.

Figure 3:
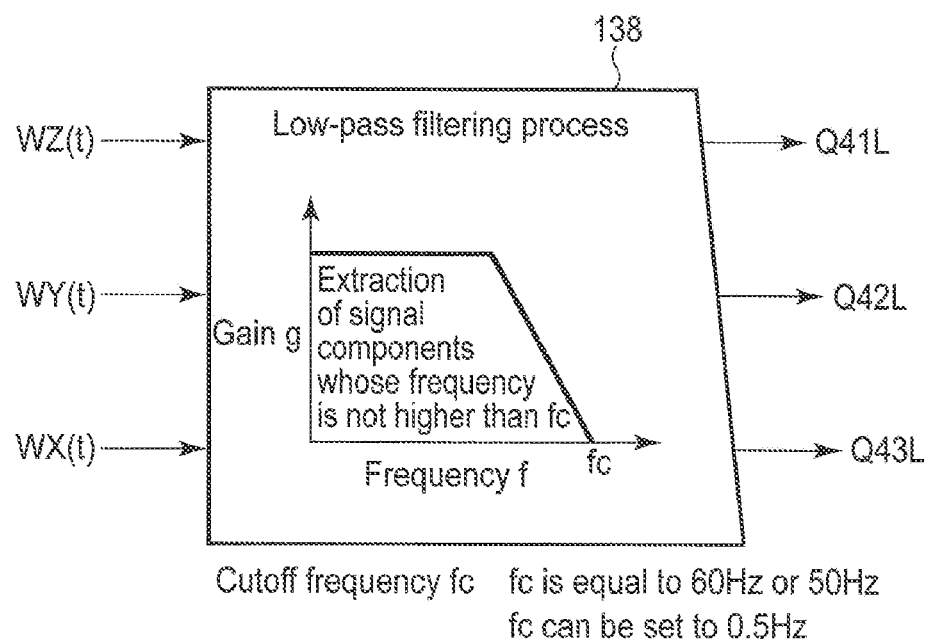
FIG. 3 is an illustration (2) of the method for extracting a predetermined criterion from detected raw signals.
Figure 12:
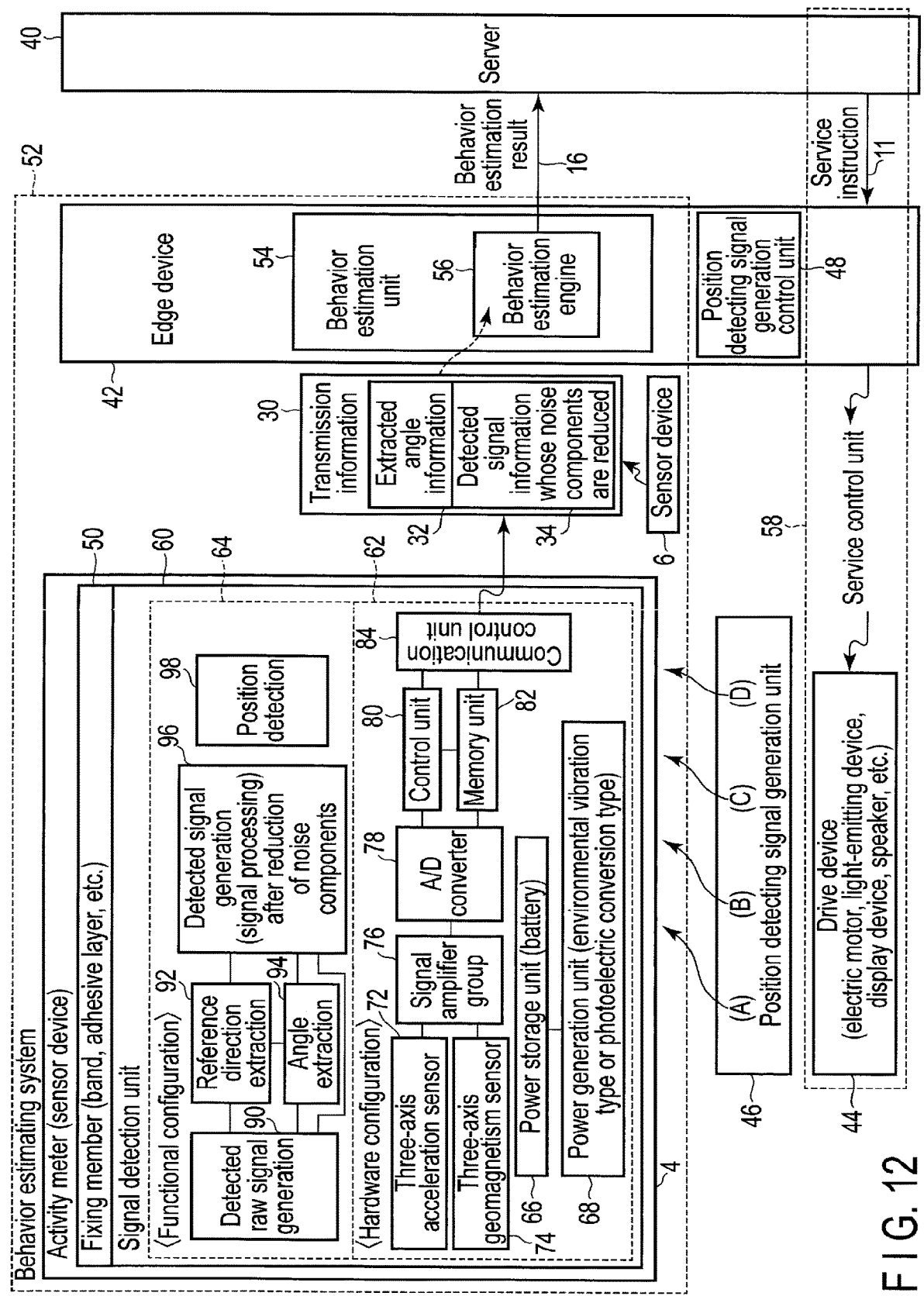
FIG. 12 is an illustration of an example of a signal processing system in the present embodiment.
Figure 13:
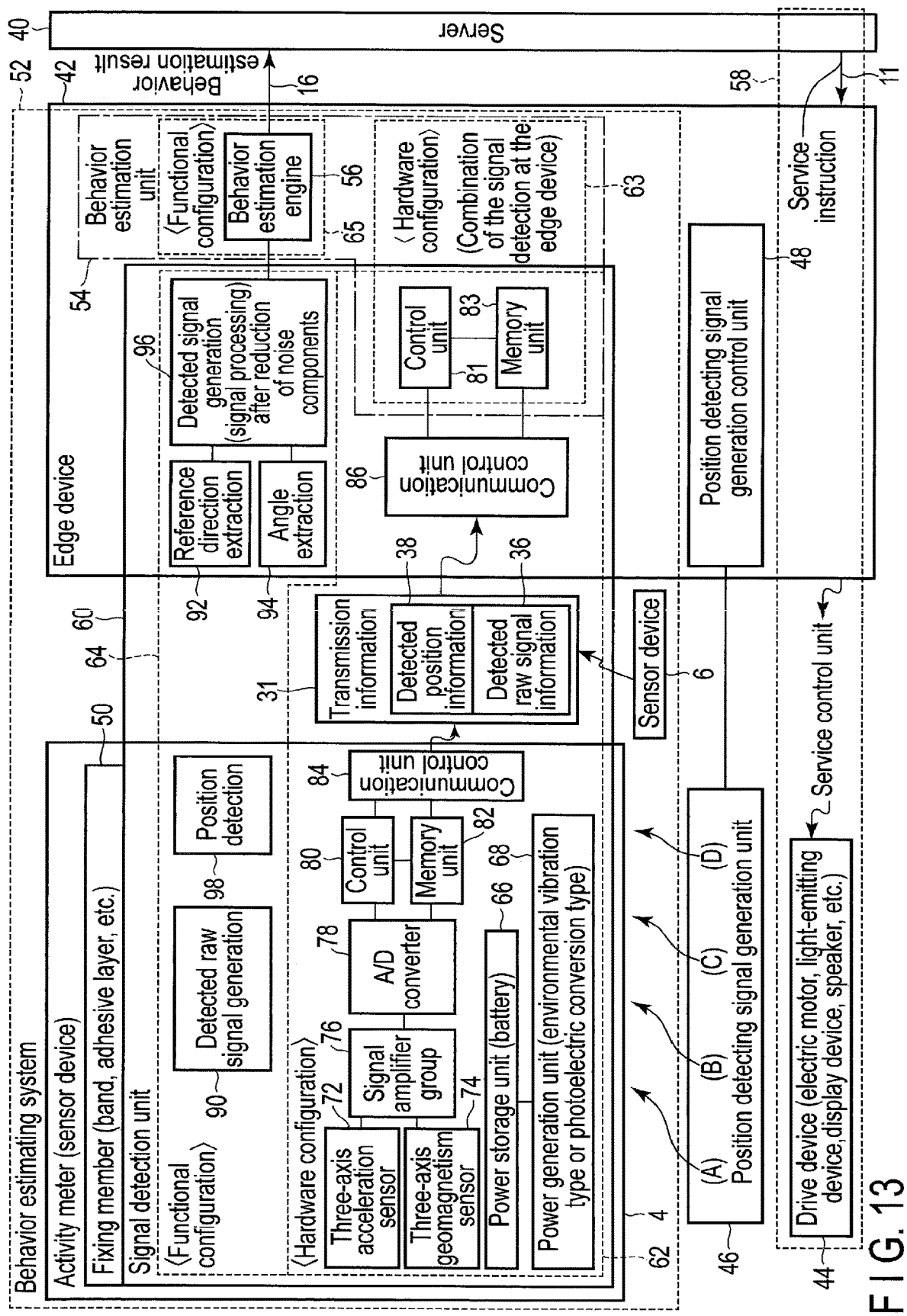
FIG. 13 is an illustration of a signal processing system according to another embodiment.

The function of reference direction extraction 92 and the function of angle extraction 94 shown in FIGS. 12 and 13 respectively correspond to a function of extracting the criterion B (gravity direction) 104 from the detected raw signals to calculate angle θ in FIGS. 3 and 2 and a function of extracting the criterion A (geomagnetism direction) 102 from the detected raw signals to calculate angle θ in FIGS. 2 and 3.

Furthermore, the function of detected signal generation (signal processing) whose noise components have been reduced shown in FIGS. 12 and 13 corresponds to a function of processing the detected raw signals WX(t), WY(t) and WZ(t) using equations (4) to (7) and converting the processed signals into detected signals "WY(t)|θyz=θs" and Wy(t) in a predetermined direction.

When the arm 120 of the person being measured 2 equipped with the activity meter 4 is vibrated, the vibration is mixed into the detected raw signals WX(t), WY(t) and WZ(t) as disturbance nose components. In most cases, the frequency due to the vibration of the arm 120 of the person being measured 2 is 0.5 Hz or higher.

Therefore, the foregoing disturbance noise components can be reduced by extracting the signal components Q41L, Q42L and Q43L of the detected raw signals WZ(t), WY(t) and WX(t) which has been subjected to a low-pass filtering process 138, as shown in FIG. 3. When the characteristics of gain g with respect to the frequency f of the low-pass filter are characteristics shown in FIG. 3, only signal components whose frequency is cutoff frequency fc or lower can be extracted. The value of cutoff frequency fc when a low-pass filtering process 130 is performed can be set to 60 Hz or 50 Hz from the above description and may be set to 0.5 Hz.

The present embodiment is not limited to the frequency characteristic shown in FIG. 3, but may adopt all filtering processes. For example, a band-pass filtering process to extract specific frequency components only can be performed.

If any signal processing is performed for the detected raw signals WZ(t), WY(t) and WX(t) to reduce disturbance noise components as described above, the advantage in which a predetermined criterion (direction) can be extracted with high accuracy is brought about.

The following is a description of a method for transforming a coordinate system of measured acceleration into a coordinate system capable of estimating behavior of the person being measured 2 using an angle between the arm of the person being measured 2 and the dolly 122, extracted from the resolved gravity acceleration value, in order to reduce variations in working estimation accuracy due to differences in physical characteristics such as height among workers.

FIG. 4 shows a coordinate transformation state between y axis/z axis and Y axis/Z axis when the X axis and x axis coincide with each other. As shown in FIG. 4, the transformation equation between waveform Wy(t)/Wz(t) and raw signal WY(t)/WZ(t) detected after the transformation is expressed as follows.

$$\begin{Bmatrix} WX(t) \\ WY(t) \\ WZ(t) \end{Bmatrix} = \begin{Bmatrix} Wx(t) \\ \cos\theta yz Wy(t) + \sin\theta yz Wz(t) \\ -\sin\theta yz Wy(t) + \cos\theta yz Wz(t) \end{Bmatrix} \quad \text{Equation (4)}$$

$$= \begin{Bmatrix} 1 & 0 & 0 \\ 0 & \cos\theta yz & \sin\theta yz \\ 0 & -\sin\theta yz & \cos\theta yz \end{Bmatrix} \begin{Bmatrix} Wx(t) \\ Wy(t) \\ Wz(t) \end{Bmatrix}$$

the X axis and x axis coincide with each other

The use of equation (4) thus makes it possible to calculate signals Wx(t), Wy(t) and Wz(t) detected after the transformation, which could be obtained in the directions of the y axis parallel to the criterion A (geomagnetism direction) 102 and the z axis (and x axis orthogonal thereto) parallel to the criterion B (gravity) 104 from the raw signals WX(t), WY(t) and WZ(t) detected from the three-axis acceleration sensor 72 (or three-axis geomagnetism sensor 74).

Then, when X axis and Xs axis coincide with each other, an angle between Y axis and Ys axis and an angle between Z axis and Zs axis are defined by a difference value "dθyz=θs−θyz" therebetween.

Using the relationship in rotating coordinate transformation between Y and Z axes and Ys and Zs axes, the transformation equation to transform the measured acceleration waveforms (detected raw signals) WY(t) and WZ(t) into standard measured acceleration WYs(t) and WZs(t) is given as follows.

$$\begin{Bmatrix} WXs(t) \\ WYs(t) \\ WZs(t) \end{Bmatrix} = \begin{Bmatrix} WXs(t) \\ \cos d\theta yz WYs(t) + \sin d\theta yz WZs(t) \\ -\sin d\theta yz WYs(t) + \cos d\theta yz WZs(t) \end{Bmatrix} \quad \text{Equation (5)}$$

$$= \begin{Bmatrix} 1 & 0 & 0 \\ 0 & \cos d\theta yz & \sin d\theta yz \\ 0 & -\sin d\theta yz & \cos d\theta yz \end{Bmatrix} \begin{Bmatrix} WX(t) \\ WY(t) \\ WZ(t) \end{Bmatrix}$$

the X axis and x axis coincide with each other

When the three-axis acceleration sensor 72 (or three-axis geomagnetism sensor 74) is used as a sensor, a plurality of detected raw signals that vary as time elapses, such as Wx(t), Wy(t) and Wz(t), are collected from one sensor or a plurality of sensors. If the detected raw signals are processed (as a result of processing of, e.g., reducing noise components on the Wy(t) side instead of collecting noise components on the Wz(t) side as a result of uneven distribution of noise components) using characteristics of the detected raw signals (extraction of predetermined original information such as θyz contained therein), the advantage that the noise components of a given detected signal (e.g., Wy(t)) that has been processed can be reduced, is brought about. The present embodiment is not limited to the noise reduction. The detected raw signals can be processed to extract a specific signal component from the detected raw signals (e.g., extraction of gravity acceleration value G using equation (1)).

As one example of extracting predetermined original information from the detected raw signals, an example of extracting a predetermined criterion (direction) using equations (1) to (3) by extracting predetermined frequency components only using the low-pass filtering process 138 shown in FIG. 3 has already been described. However, the present embodiment is not limited to this example but may include an example of extracting "all types of information" contained in the detected raw signals. For example, noise components (rolling components 208) contained in both the detected raw signals WY(t) and WZ(t) can be caused to correspond to "predetermined information contained in the detected raw signals", as will be described with reference to FIG. 26.

The detected raw signals collected simultaneously from sensors of different types such as the three-axis acceleration sensor 72 and a three-axis angular velocity sensor 212 can be processed. For example, "predetermined original information contained in the detected raw signals" in the embodiment shown in FIG. 28 (the details thereof will be described later) corresponds to "rotation direction 218 of steering wheel 214", "acceleration/deceleration direction of a bus, a truck or an automobile 210", "the change in moving direction of a bus, a truck or an automobile 210" or the like.

As a method for extracting these original information, for example, a specific sensor attachment direction (the direction of a predetermined coordinate axis set in a specific sensor) can be distinguished and a specific signal component (e.g., detection of signal characteristics such as an absolute value of detected acceleration increasing at the start of acceleration/deceleration and converging to zero as the speed approaches a constant speed) can be used.

Figure 5:
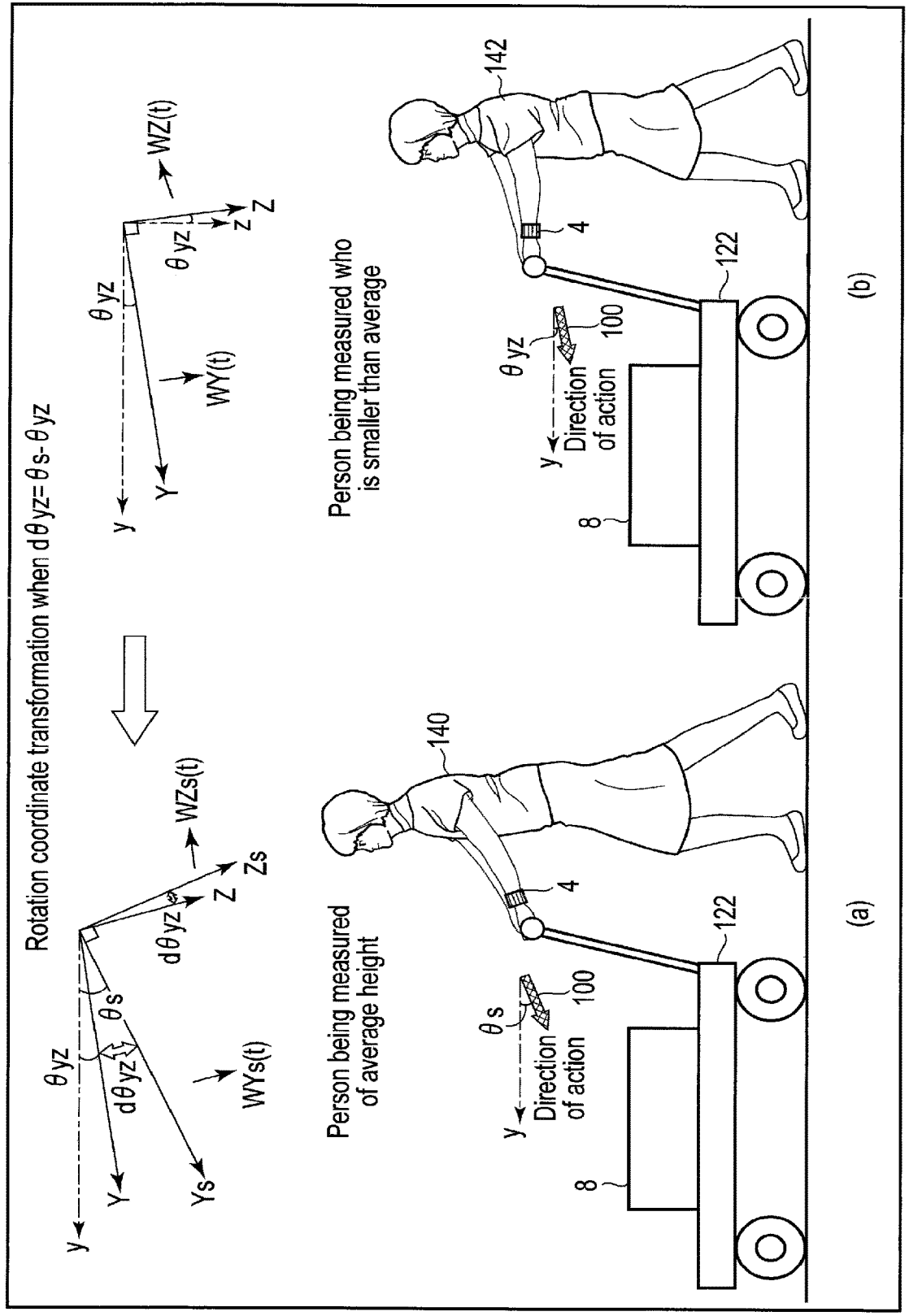
FIG. 5 is an illustration of a situation where a person being measured who is smaller in stature than average.
Figure 6:
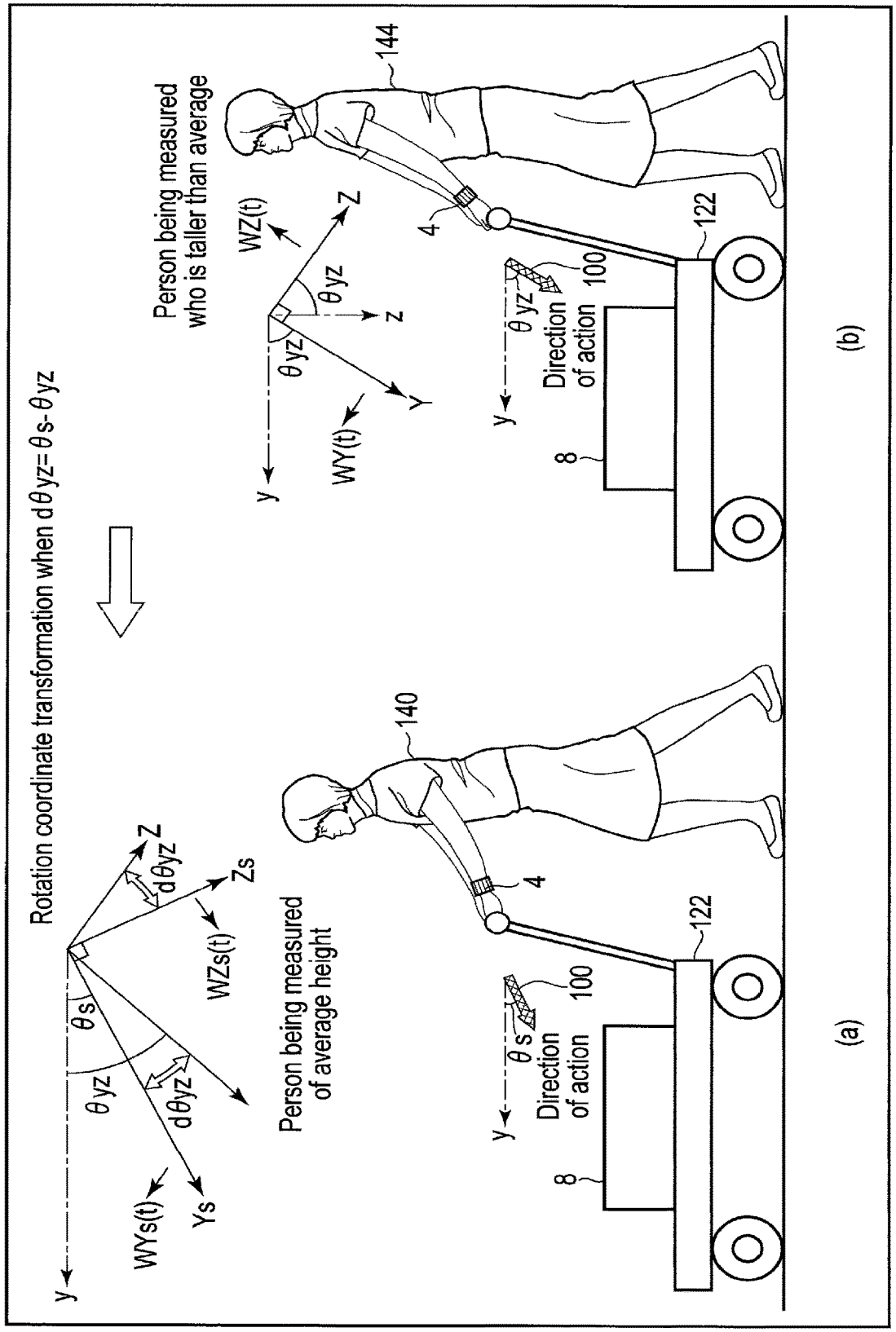
FIG. 6 is an illustration of a situation where a person being measured who is taller in stature than average.

The following is a description of how to handle the dolly 122 for a person being measured 140 of average height, a person being measured 142 who is smaller than average or a person being measured 144 who is taller than average. As shown in FIG. 5, angle θyz formed when the person being measured 142 pushes the dolly 122 is smaller than angle θs formed when the person being measured 140 pushes the dolly 122 (θyz<θs). On the other hand, as shown in FIG. 6, angle θyz formed when the person being measured 144 pushes the dolly 122 is larger than angle θs (θyz>θs).

As an application example of the present embodiment described with reference to FIGS. 5 and 6, a feedback method (a kind of learning function) regarding a threshold value used in a process of estimating behavior of the person being measured 142 who is smaller than average or the person being measured 144 who is taller than average, will be described. When the person being measured 144 who is taller than average pushes the dolly 122 ((a) in FIG. 7), the value of angle θyz formed between the direction of action 100 and the direction (y axis) in which the dolly 122 moves increases. In this case, the force by which the person being measured 144 presses the dolly 122 on the floor surface increases. Accordingly, the kinetic friction force and static friction force of the dolly 122 increase and the dolly 122 becomes difficult to move.

Figure 7:
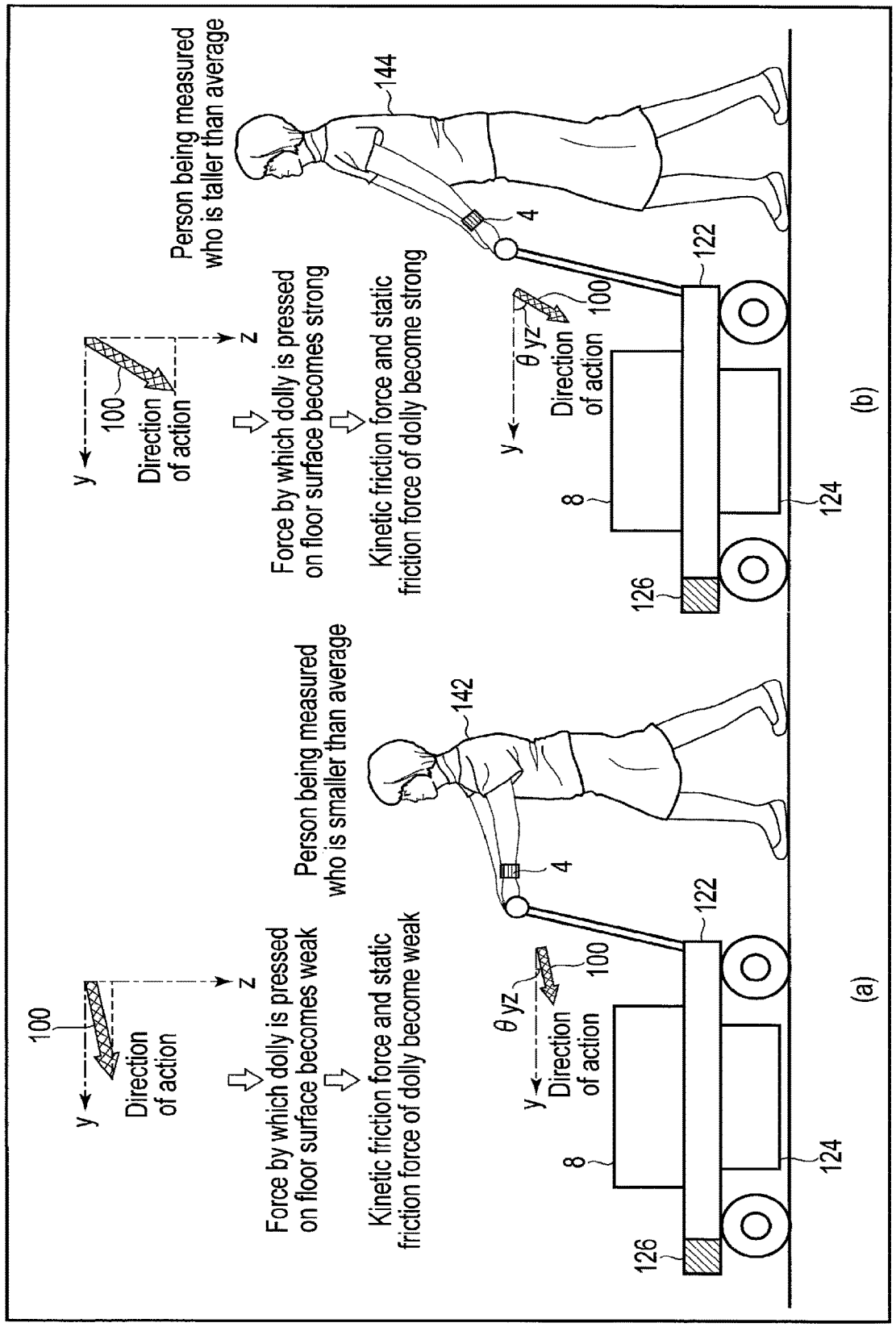
FIG. 7 is an illustration of variations in the kinetic friction force and static friction force of a dolly which depend upon the direction of action.

When the person being measured 142 who is smaller than average pushes the dolly 122 ((b) in FIG. 7), the value of angle θyz formed between the direction of action 100 and the direction (y-axis direction) in which the dolly 122 moves decreases. Thus, the force by which the person being measured 142 presses the dolly 122 on the floor surface becomes relatively weak. Accordingly, the kinetic friction force and static friction force of the dolly become weak and the dolly 122 becomes easy to move. The variations in kinetic friction force and static friction force therefore affect the behavior estimation of the person being measured 2.

Figure 8:
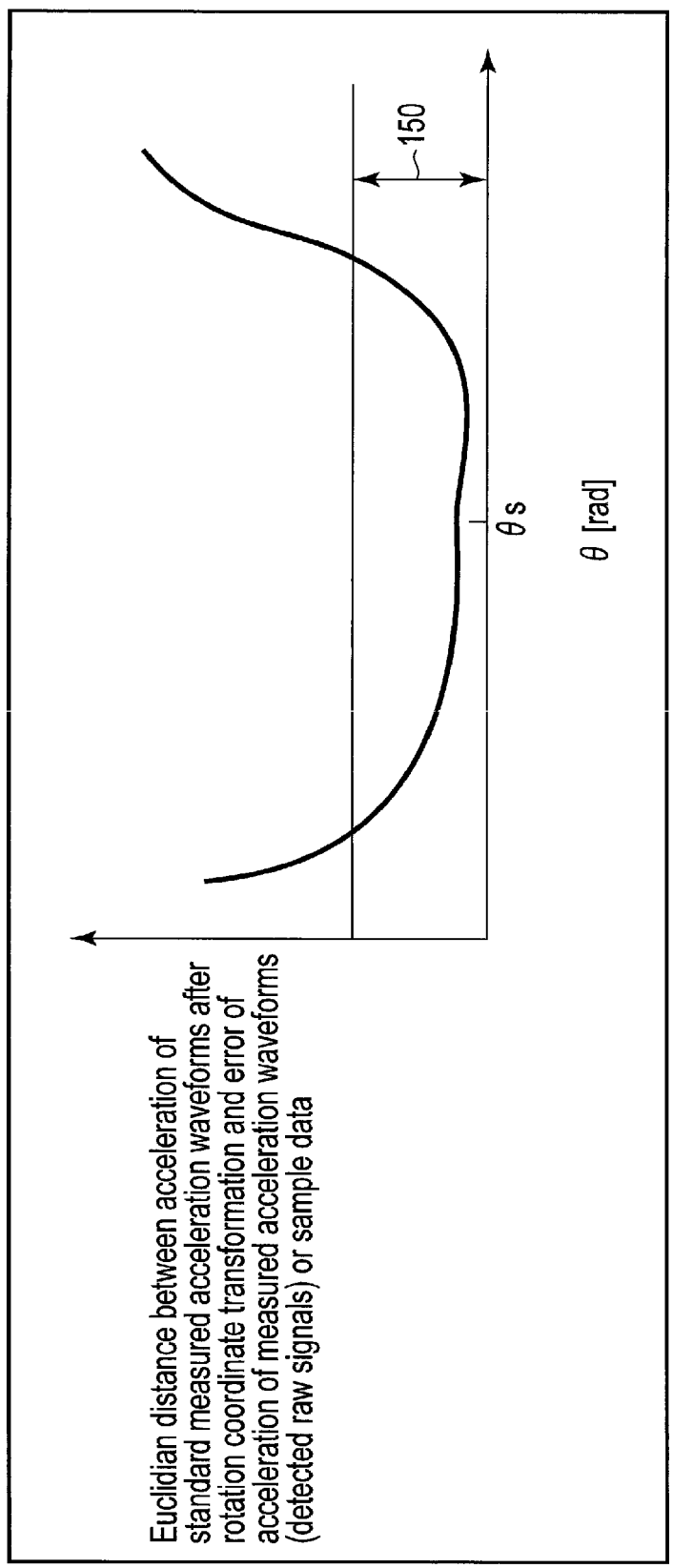
FIG. 8 is an illustration of a person-being-measured behavior estimating method.

Here, angle θs formed between the direction of action 100 in which the person being measured 140 of average height pushes the dolly 122 and the direction (y-axis direction) in which the dolly 122 moves is considered to be a criterion. FIG. 8 shows the relationship in Euclidian distance between the transformed standard measured acceleration with respect to angle θyz formed when the person being measured 2 pushes the dolly 122 based on angle θs and the amount of error among the measured acceleration waveforms (detected raw signals) or the standard measured acceleration waveforms (sample data).

In θyz≈θs, the characteristics shown in FIG. 8 are represented by a value that is considerably smaller than a determination threshold value 150 during behavior estimation of a person being measured. However, it is understood that as angle θyz greatly deviates from θs, the characteristics becomes larger than the determination threshold value 150 during behavior estimation of a person being measured and the accuracy of the behavior estimation lowers. To prevent the accuracy from lowering, in the present embodiment, when angle θyz greatly deviates from θs, the determination threshold value 150 during the behavior estimation is automatically corrected (the determination threshold value 150 is largely reset). This brings about the advantage that the behavior of the person being measured 2 can be estimated with high accuracy even though angle θyz greatly deviates from θs.

The above-described equation (4) is a transformation equation in the case where the X axis and x axis coincide with each other. In other words, FIG. 4 based on which the above equation (4) is derived, shows that the y axis and z axis are rotated by θyz and transformed into the Y axis and Z axis with the X axis and x axis coinciding with each other (coordinate transformation of vertical rotation••3D transformation)

Figure 9:
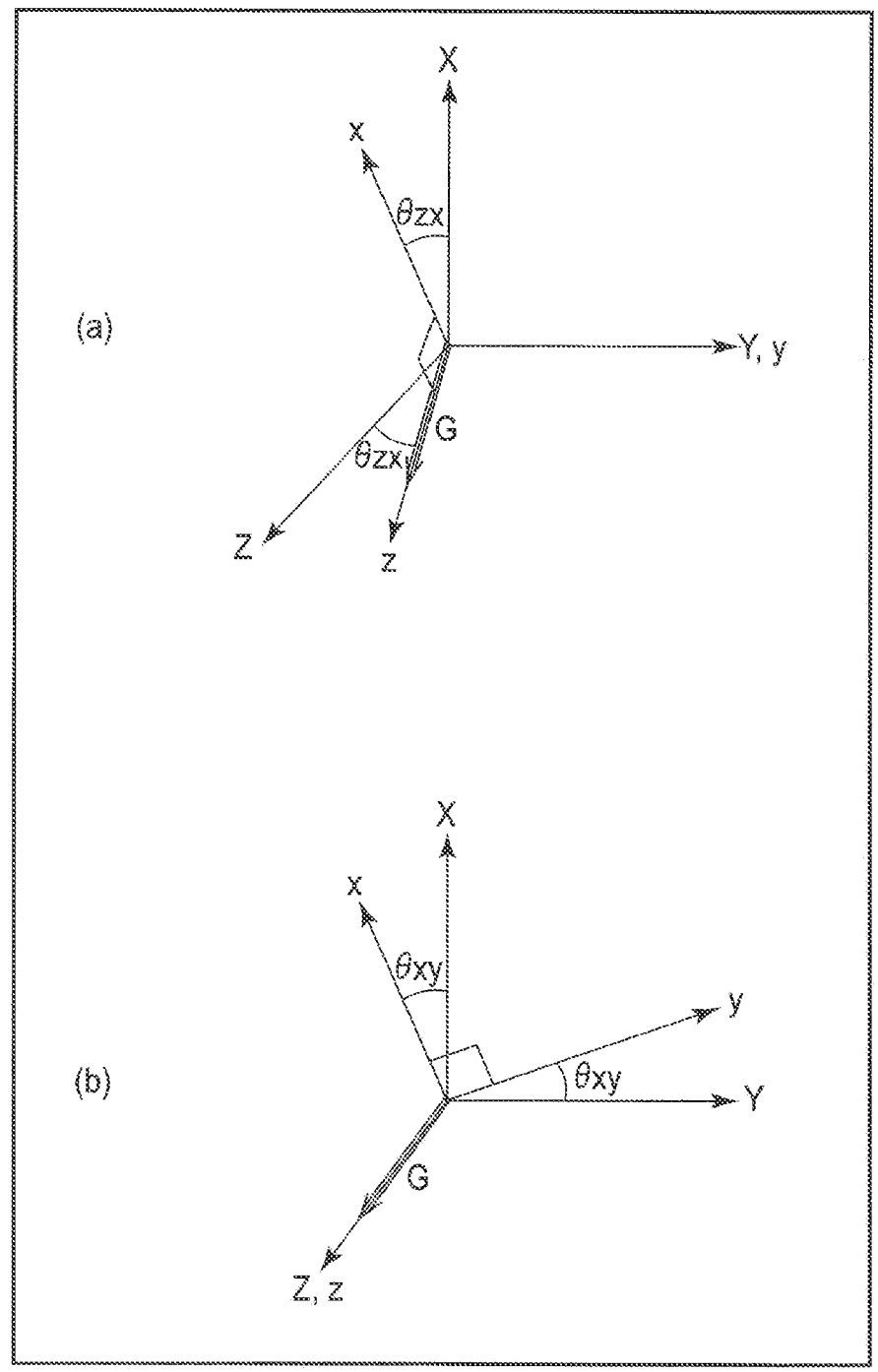
FIG. 9 is an illustration of a coordinate transformation method among a plurality of detected signals in a three-dimensional direction.

In contrast, (a) in FIG. 9 shows that the z axis and x axis are rotated by θzx and transformed into the Z axis and X axis with the Y axis and y axis coinciding with each other (coordinate transformation of horizontal rotation••rotation transformation). Similarly, (b) in FIG. 9 shows that the x axis and y axis are rotated by θxy and transformed into the X axis and Y axis with the Z axis and z axis coinciding with each other.

Like the equation (4) derived based on FIG. 4, the following general transformation equation is derived using FIG. 4 and (a) and (b) of FIG. 9.

$$\begin{Bmatrix} WX(t) \\ WY(t) \\ WZ(t) \end{Bmatrix} = \begin{Bmatrix} \cos\theta xz & \sin\theta xy & 0 \\ -\sin\theta xy & \cos\theta xy & 0 \\ 0 & 0 & 1 \end{Bmatrix} \quad \text{Equation (6)}$$

$$\begin{Bmatrix} \cos\theta zx & 0 & -\sin\theta zx \\ 0 & 1 & 0 \\ \sin\theta zx & 0 & \cos\theta zx \end{Bmatrix}$$

$$\begin{Bmatrix} 1 & 0 & 0 \\ 0 & \cos\theta yz & \sin\theta yz \\ 0 & -\sin\theta yz & \cos\theta yz \end{Bmatrix} \begin{Bmatrix} Wx(t) \\ Wy(t) \\ Wz(t) \end{Bmatrix}$$

general transformation equation

A signal processing method to reduce the influence of irregularities of a floor surface 128 will be described in the case where acceleration variation components corresponding to the irregularities of the floor surface 128 to be superimposed on the signal component Wz(t) are considered to be noise components as shown in, for example, (b) of FIG. 17 described below. The noise components are mixed into a detected raw signal "WY(t)|θyz<θs" shown in (c) of FIG. 17 and a detected raw signal "WY(t)|θyz>θs" shown in (e) of FIG. 17. Consider a case where a detected signal of Wy(t) with few noise components can be obtained by performing signal processing using the detected raw signal "WY(t)

|θyz<θs" and detected raw signal "WY(t)|θyz>θs". The above signal processing means extracting the detected signal of Wy(t) obtained by reducing noise components from the detected raw signal "WY(t)|θyz<θs" or "WY(t)|θyz>θs" into which a large number of noise components are mixed. This corresponds to the function of the detected signal extraction (signal processing) 96 after reduction of noise components in FIG. 13.

Then, as a signal processing method to reduce the influence of height of the person being measured 2, a method for transforming the detected raw signals ("measured acceleration waveforms" described later, namely, detected raw signals) WX(t), WY(t) and WZ(t) shown in (c) or (e) of FIG. 17 into detected signals (transformed standard measured acceleration described later) "WY(t)|θyz=θs" (or WYs(t)) when θyz=θs, corresponding to the person being measured 140 of average height, will be described.

Figure 10:
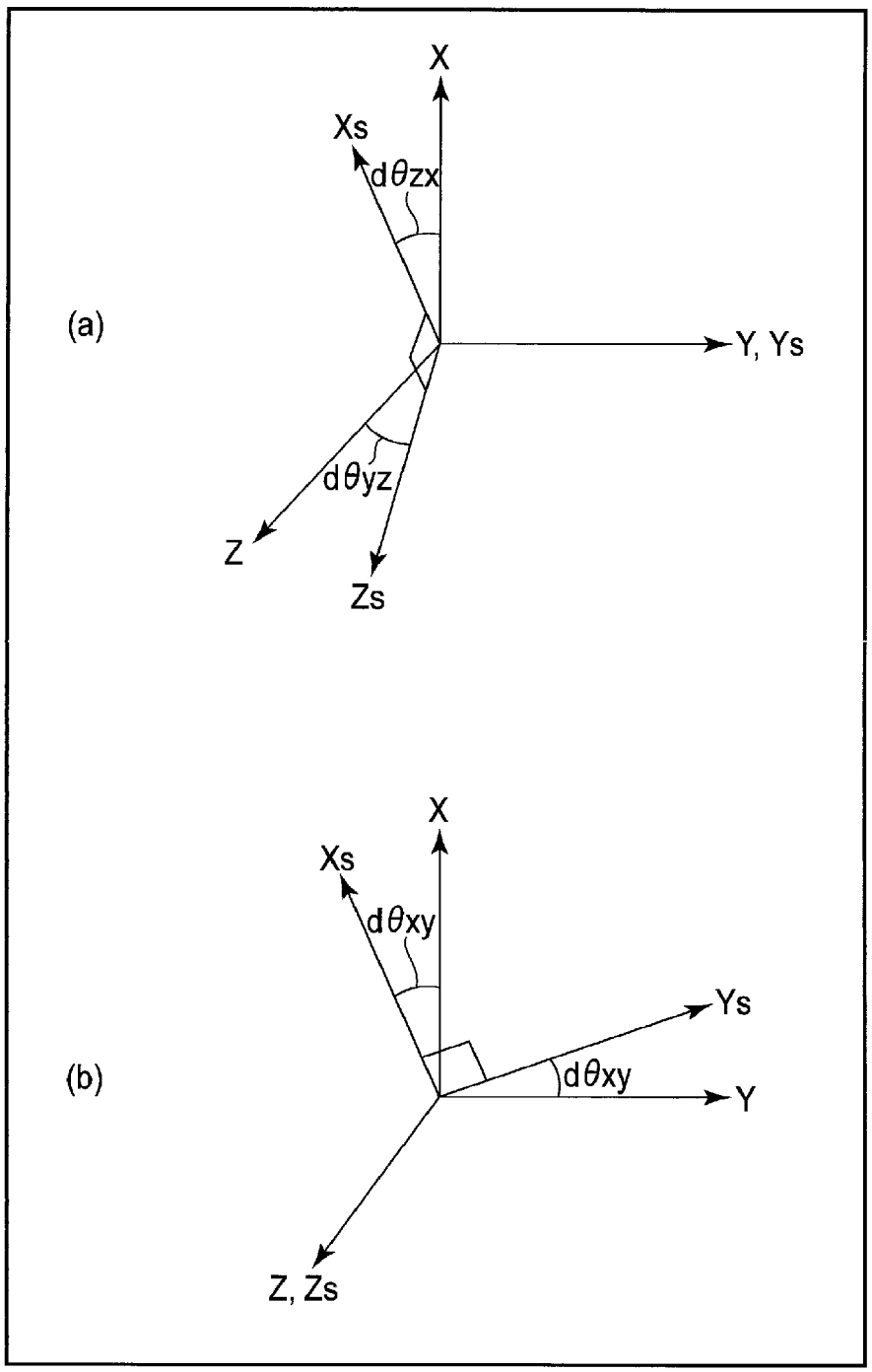
FIG. 10 is an illustration of the relationship between the measured acceleration waveform (detected raw signal) and the transformed standard measured acceleration in the three-dimensional direction.

Here, as shown in (a) of FIG. 10, the angle formed between the Z axis and Zs axis and the angle formed between the X axis and Xs axis when the Y axis and Ys axis coincide with each other are represented by dθzx. Similarly, as shown in (b) of FIG. 10, the angle formed between the X axis and Xs axis and the angle formed between the Y axis and Ys axis when the Z axis and Zs axis coincide with each other are represented by dθxy.

The following general transformation equation to transform the measured acceleration waveforms (detected raw signals) WX(t), WY(t) and WZ(t) when the X axis and Xs axis do not coincide with each other into the standard measured accelerations WXs(t), WYs(t) and WZs(t) is given by expanding the above equation (5) from FIG. 4 and (a) and (b) of FIG. 10.

$$\begin{Bmatrix} WXs(t) \\ WYs(t) \\ WZs(t) \end{Bmatrix} = \begin{Bmatrix} \cos d\theta xz & \sin d\theta xy & 0 \\ -\sin d\theta xy & \cos d\theta xy & 0 \\ 0 & 0 & 1 \end{Bmatrix} \quad \text{Equation (7)}$$
$$\begin{Bmatrix} \cos d\theta zx & 0 & -\sin d\theta zx \\ 0 & 1 & 0 \\ \sin d\theta zx & 0 & \cos d\theta zx \end{Bmatrix}$$
$$\begin{Bmatrix} 1 & 0 & 0 \\ 0 & \cos d\theta yz & \sin d\theta yz \\ 0 & -\sin d\theta yz & \cos d\theta yz \end{Bmatrix} \begin{Bmatrix} WX(t) \\ WY(t) \\ WZ(t) \end{Bmatrix}$$

general transformation equation

The measured acceleration waveforms (detected raw signals) shown in (c) or (e) of FIG. 17 can thus be transformed into the standard measured acceleration "WY(t)|θyz=θs" (or Ws) corresponding to θyz=θs.

As described above, the measured acceleration waveforms (detected raw signals) WX(t), WY(t) and WZ(t) obtained from the activity meter 4 attached to the person being measured 142 who is smaller than average and the person being measured 144 who is taller than average are transformed into WXs(t), WYs(t) and WZs(t) (standard measured acceleration transformed into a corresponding average height). Based upon the transformed detected signals (standard measured acceleration), behavior of the persons being measured 142 and 144 can be estimated. This brings about the advantage of allowing behavior of the persons being measured 140 to 144 to be estimated with high accuracy on a common scale regardless of a difference in height among the persons being measured 140 to 144.

A method of using a rotating coordinate transformation between the coordinate axes shown in FIG. 4 has been so far described as a method of detecting a signal to reduce the influence of height of the person being measured 2 by signal processing. However, the present embodiment is not limited to this method but may use any other signal processing methods if they use the raw signals Wx(t), Wy(t) and Wz(t) detected from the different sensors 72 and 74. As one example, the detected raw signals Wx(t), Wy(t) and Wz(t) can be regarded as a three-dimensional vector to perform vector operation among vector components (e.g., vector synthesis).

The present embodiment is not limited to the above signal processing methods. The raw signals detected from the different sensors 72 and 74 can be processed to perform detected signal generation (signal processing) 96 (FIG. 12 or 13) after reduction of noise components. In other words, in the conversion between the detected signals using the equation (4) calculated with reference to FIG. 4, conversion between signals detected from, e.g., the three-axis acceleration sensor 72 only is performed. However, the present embodiment is not limited to this conversion. For example, signal processing can be performed by combining signals detected from the three-axis geomagnetism sensor 74 with the signals detected from the sensor 72 to reduce noise components of the detected raw signals.

An example of behavior estimation of the person being measured 2 using a detected signal after the rotation transformation (signal processing) will be described below.

Angle θyz of the arm 120 of the person being measured 2 who is pushing the dolly 122 changes over time. Thus, the process of calculating the detected signal after rotation transformation (signal processing) needs to be repeated many times.

Figure 21:
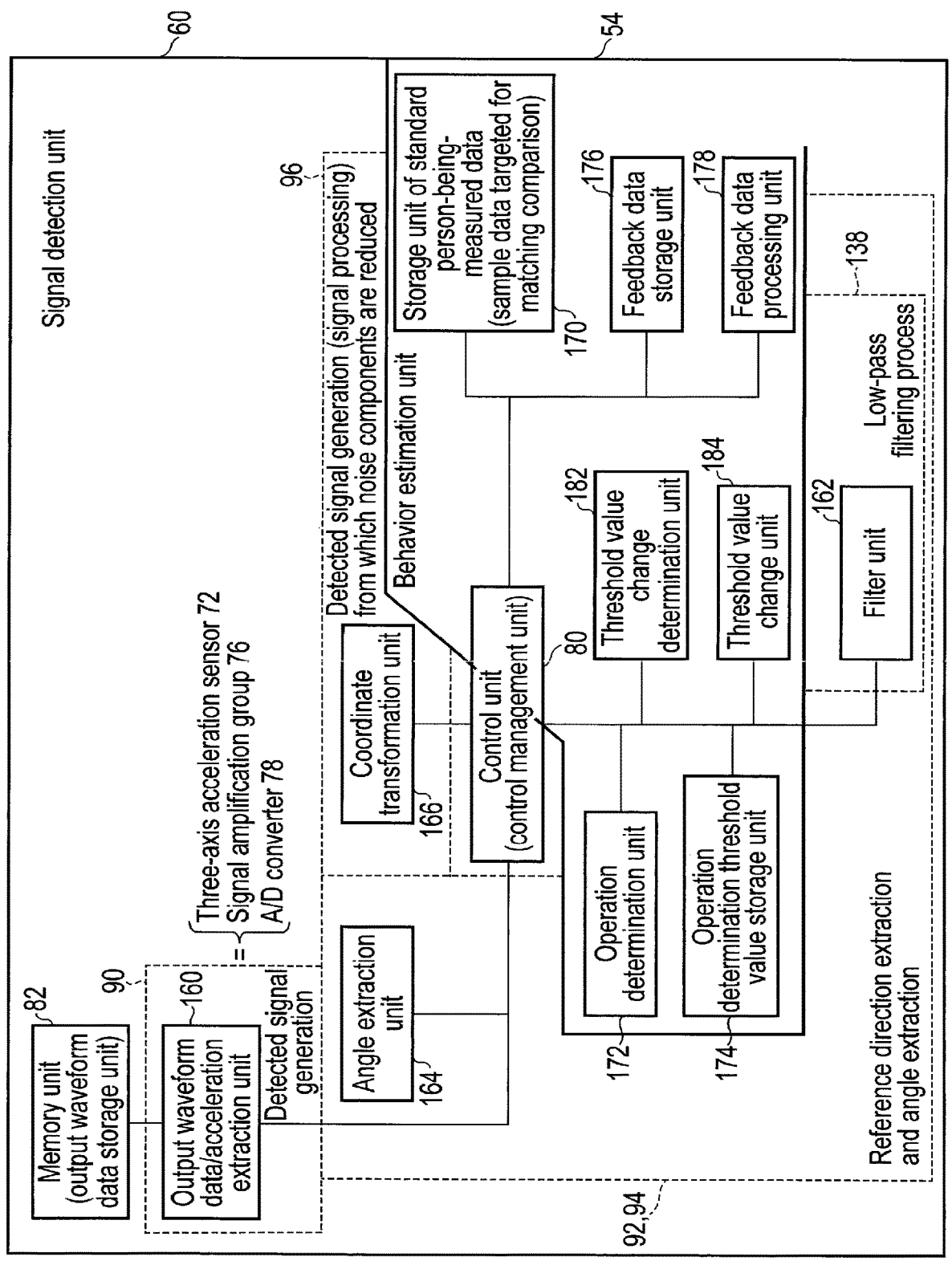
FIG. 21 is an illustration of an example of hardware configuration in a behavior estimating system.

Prior to the description of an example of behavior estimation performed by a behavior estimating system 52 shown in FIG. 21 (or FIG. 12 or 13), the terms to be used here will be defined. One or more of the detected raw signals WX(t), WY(t) and WZ(t) collected from the three-axis acceleration sensor 72 will be referred to as "measured acceleration waveforms (detected raw signals)". The signals detected when θyz=θs (one or more thereof) will be referred to as "standard acceleration". The detected raw signals WX(t)|θyz=θs, WY(t)|θyz=θs, and WZ(t)|θyz=θs (one or more thereof) obtained directly when the person being measured 140 of average height (FIG. 5 or 6) pushes the dolly 122 and collected from the three-axis acceleration sensor 72, corresponds to the "standard acceleration" described above.

When the above standard acceleration (detected raw signal) is stored in the memory unit 82 (FIG. 12) and used as reference data (sample data) during the behavior estimation, it will be referred to as "standard measured acceleration waveform (sample data)". The above standard measured acceleration waveform (sample data) may be sample data collected only once from the only person being measured 140 of average height, an average value of data collected more than once, or an average value of data obtained from a plurality of persons being measured 140 of average height.

As has been described with reference to FIGS. 5 and 6, the detected signals obtained after the standard acceleration transformed using the equation (5) or (7) based on the detected raw signals collected from the person being measured 142 who is smaller than average or the person being measured 144 who is taller than average, will be referred to as "standard measured acceleration after transformation".

In the foregoing process, a process "from collection of the detected raw signals to signal processing (rotation transformation of the detected signals)" will be referred to as "cycle". The number of times the cycle is repeated for one second will be referred to as "cycle frequency" and the time required for one cycle will be referred to as "cycle period". The shorter the cycle period, the more finely and accurately information about the behavior of the person being measured 2 can be collected. Thus, the cycle period corresponds to the "resolution" (information collecting speed) of the cycle processing.

In the present embodiment, statistical processing is performed after data of the transformed standard measured acceleration obtained for each cycle is stored for a predetermined period. The storage period of the data of the transformed standard measured acceleration necessary for the statistical processing will be therefore referred to as "statistical processing storage period".

Furthermore, the results of statistical processing calculated for each statistical processing storage period are collected for a predetermined period to estimate the behavior of the person being measured 2. The unit period (period during which the results of statistical processing are collected) of the behavior estimation will be referred to as "behavior estimation determination period".

In the system (behavior estimating system 52) of the present embodiment, the higher the cycle frequency, the higher the resolution of the cycle processing, which facilitates detection of a rapid change in behavior of the person being measured 2. In the example of (b) of FIG. 1, the behavior (working) of the person being measured 2 changes every minute or every two minutes from the manual operation 20 to dolly movement 20, stopping, and walking 26. When the person being measured 2 is busy, his or her behavior (working) may change more frequently. When the person being measured 2 is busy, if the cycle of collection/signal processing of the detected raw signals is once per minute, the behavior (working) of the person being measured 2 which changes frequently cannot be finely pursued. The cycle period in the present embodiment is therefore set to not longer than 10 seconds at most.

When the person being measured 2 is very busy, his or her behavior (working) may change in seconds. To deal with such a rapid change, it is desirable that the cycle period be not longer than 0.5 seconds in the present embodiment. In the following description, 20 Hz is provisionally set as an example of the cycle frequency.

An example has been described with reference to FIG. 3, in which the value of cutoff frequency fc is set to 50 Hz or 60 Hz when a predetermined criterion is extracted. The value of cutoff frequency fc is somewhat consistent with the foregoing cycle frequency of 20 Hz. If, however, the cutoff frequency fc is set to a low value of 0.5 Hz or the like, it is technically impossible to subject the detected raw signals to the low-pass filtering process 138 for each cycle. In this case, the low-pass filtering process 138 can be performed using the detected raw signals in a plurality of cycles.

As has been described, in the system (signal processing system) of the present embodiment, the raw signals detected from the three-axis acceleration sensor 72 and the three-axis geomagnetism sensor 74 (digital signals obtained by an AD converter 78 through a signal amplifier group 76) are stored temporarily in the memory unit 82, then read out in response to an instruction from a control unit 80 and processed. Therefore, the low-pass filtering process 138 using the detected raw signals between a plurality of cycles is facilitated. However, the present embodiment is not limited to this signal processing. If the signals are properly processed in the memory unit 82, the signal processing can be performed in real time.

The following is a description of the statistical processing storage period described above. For example, statistical processing for data for only one cycle is meaningless. To perform effective statistical processing, it is desirable to store data for at least four or more cycles, preferably ten or more cycles. For example, when the cycle frequency is 20 Hz (cycle period is 50 mS), 0.5 seconds are required as the statistical processing storage period in order to store data for ten cycles.

If the above determination period for behavior estimation is not shorter than the statistical processing storage period as a minimum requirement, the behavior of the person being measured 2 can be estimated. To estimate the behavior more accurately, however, the determination period of the behavior estimation needs to be four or more times longer than the statistical processing storage period (preferably eight or more times). For the above reason, four seconds can be set as the determination period of the behavior estimation.

From the above descriptions, the relationship among the periods is as expressed by "determination period of behavior estimation"≥"statistical processing storage period"≥"cycle period". If the behavior of the person being measured 2 is estimated for each determination period of behavior estimation (e.g., every four seconds), service providing to the person being measured 2 is greatly delayed. Therefore, in the system (behavior estimating system 52) according to the present embodiment, the behavior estimation process is continued while shifting every cycle period. Similarly, the statistical processing storage period is sequentially set while shifting every cycle period.

As a method for estimating activity of the person being measured 2 using the detected signals (standard measured acceleration) which have been processed, one of the following determinations or a combination thereof is made in the present embodiment.

(A) Determination of irregularities and dispersion among the detected signals before and after rotation transformation (signal processing);

(B) Determination of similarities between the transformed standard measured acceleration and sample data; and (C) Determination of expansion/contraction matching between the transformed standard measured acceleration and sample data.

The above behavior estimation methods will be described.

(A) Determination of irregularities and dispersion among the detected signals before and after rotation transformation (signal processing)

(A1) A difference (magnitude of movement) in dispersion between the measured acceleration waveform (detected raw signal) in the Z-axis direction (gravity component) or the Y-axis direction (dolly moving direction) for each statistical processing storage period described above and the transformed standard measured acceleration (or dispersion characteristics among data in the statistical processing storage period when a difference value between the measured acceleration waveform (detected raw signal) for each cycle and the transformed standard measured acceleration is regarded as one data) is statistically processed. It is then determined whether the statistically processed dispersion value falls within a predetermined threshold value.

(A2) A difference in random value (irregularities) between the measured acceleration waveform (detected raw signal) in the Z-axis direction (gravity component) or the Y-axis direction (dolly moving direction) for each statistical processing storage period and the transformed standard measured acceleration is used for behavior estimation. It is then determined whether the calculated random value falls within a predetermined threshold value.

The random value means the number of variations of the sign of the above difference value within the statistical processing storage period. Assume that the difference value between the measured acceleration waveform (detected raw signal) in the k-th cycle and the transformed standard measured acceleration is $\Delta(k)$. When "$\Delta(k)<\Delta(k+1)$", $D(k)=+1$ is assigned. When "$\Delta(k)>\Delta(k+1)$", $D(k)=-1$ is set. When "$\Delta(k)=\Delta(k+1)$", $D(k)=0$ is set. The total value of $D(k)$ in the statistical processing storage period is defined as a random value. Consider the case where the sequence of $\{D(1), D(2), D(3), D(4), D(5), D(6), D(7), D(8), D(9)\}$ is $\{+1, +1, +1, -1, -1, +1, +1, +1, +1\}$. In this sequence, the sign changes from +1 to −1 once and the sign changes from −1 to +1 once. Since the sign change is made two times in total, the random value is "2".

If the frequency (similarity) that satisfies the above (A1) and (A2) at the same time within a determination period of behavior estimation is 80% or more, it is determined as matching. Assume that the cycle period is 50 mS, the statistical processing storage period is 0.5 seconds, and the determination period of behavior estimation is four seconds. As described above, in the present embodiment, the statistical processing storage period is set sequentially while shifting every cycle period. The statistical processing storage period can thus be set only eighty times (4000÷50) during the above determination period (four seconds) of behavior estimation. If, therefore, (A1) and (A2) are satisfied at the same time with the frequency of 80% or more (64 times or more) in the statistical processing results of eighty times, it is determined that the person being measured 2 is moving the dolly 20.

(B) Determination of similarities between the transformed standard measured acceleration and sample data (B1) A difference (magnitude of movement) in dispersion between the transformed standard measured acceleration in the Z-axis direction (gravity component) or the Y-axis direction (dolly moving direction) for each statistical processing storage period and the standard measured acceleration waveform (sample data) (or dispersion characteristics among data in the statistical processing storage period when a difference value between the transformed standard measured acceleration for each cycle and the standard measured acceleration waveform (sample data) is regarded as one data) is statistically processed. It is then determined whether the statistically processed dispersion value falls within a predetermined threshold value.

(B2) A difference in random value (irregularities) between the transformed standard measured acceleration in the Z-axis direction (gravity component) or the Y-axis direction (dolly moving direction) for each statistical processing storage period and the standard measured acceleration waveform (sample data) is used for behavior estimation. It is then determined whether the calculated random value falls within a predetermined threshold value.

If the frequency (similarity) that satisfies the above (B1) and (B2) at the same time within a determination period of behavior estimation is 80% or more, it is determined as matching.

(C) Determination of expansion/contraction matching between the transformed standard measured acceleration and sample data An extension/contraction matching technique is applied between the transformed standard measured acceleration in the Z-axis direction (gravity component) or the Y-axis direction (dolly moving direction) for each statistical processing storage period and the standard measured acceleration waveform (sample data). It is then determined whether the Euclidian distance (described in detail later) obtained for each statistical processing storage period falls within a predetermined threshold value. If the frequency (similarity) with which the Euclidian distance falls within the threshold value in the determination period of behavior estimation is 80% or more, it is determined as matching.

The foregoing extension/contraction matching technique is a general term regarding a pattern matching technique to calculate a similarity between the pattern of sample data (standard measured acceleration waveforms) and the pattern of detected signals (transformed standard measured acceleration), taking into consideration partial extension/contraction on a time axis between these patterns.

In the system (behavior estimating system 52) according to the present embodiment, the values (detected values) of detected raw signals WX(t), WY(t) and WZ(t) (at least one of these signals or a predetermined frequency component and a predetermined element component in a signal) vary with time. Since there is a difference in behavior speed (working speed) among persons being measured 2, the speed varying with time varies from person being measured 2 to person being measured 2. Thus, the varying speed of detected raw signals for use in behavior estimation of human beings and animals and state estimation to estimate the state of a predetermined object varies from person being measured to person being measured. Therefore, the use of the extension/contraction matching technique in the estimation process in the system (behavior estimating system 52) according to the present embodiment brings about the advantage of absorbing the variations in varying speed of detected raw signals (adapting to the extension/contraction of detected raw signals in a direction in which time elapses) and thus improving estimation accuracy.

The present embodiment will now be described by way of a specific example of the positioning of the embodiment. First, a method for planning an estimation process and business improvement 10 or providing service using detected raw signals obtained while the person being measured 2 shown in FIG. 1 is moving 22 the dolly, will be described. The present embodiment is not limited to these works but can be applied to works such as manual operation 20, stopping 24 and walking 26 shown in (b) of FIG. 1.

Figure 11:
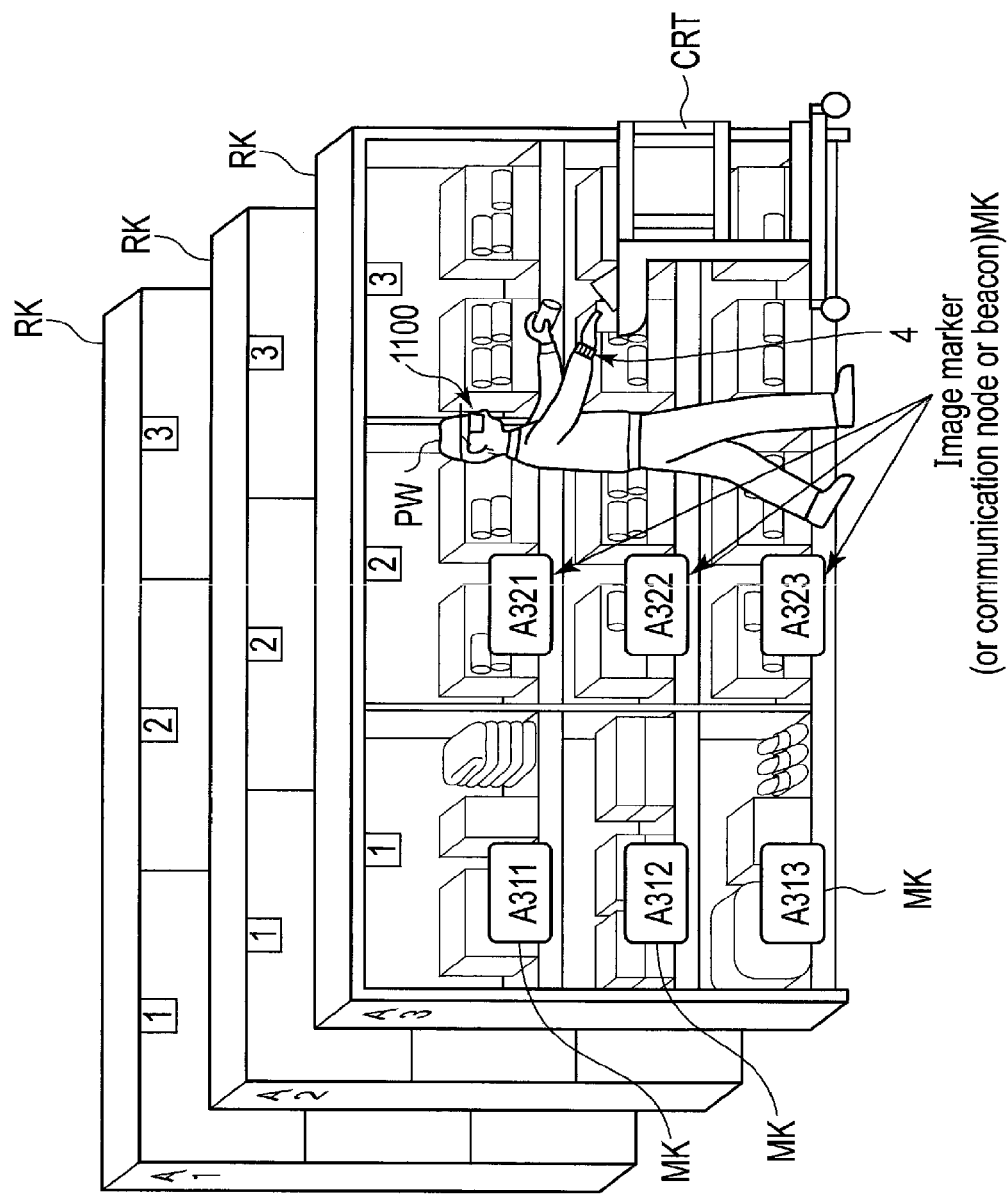
FIG. 11 is an illustration of an example of application to a warehouse management system (WMS) of the present embodiment.

As a situation of use of the present embodiment shown in FIG. 1, an example of application to a warehouse management system (WMS) is shown in FIG. 11. The WMS is roughly divided into mechanisms to solve two different problems corresponding to "inventory control" and "working support". As an example of the inventory control, there are grasping of best before dates of stocks, grasping of stock position of each article in a warehouse, etc.

As an example of an application situation of the working support is shown in FIG. 11. An image marker MK is set for each of articles stored for each of racks (shelves) RK arranged in the warehouse to indicate the contents of each article. As an example of the image marker MK, there are a one-dimensional or 2-dimensional direction code or a mark (icon, etc.) which allows the contents of an article to be easily distinguished at first sight. The present embodiment is not limited to the code or mark. The image marker MK may be a communication node incorporating a wireless communication function for each image marker MK and an image marker MK having placement information (position information) using a beacon.

A personal worker (PW) (or person being measured 2) chooses and extracts (picks) a designated one of the articles stored in each of the racks (shelves) RK and puts it in a cart (basket) CRT (or puts it on the dolly 122 if it is a large article 8 to be carried).

Then, the personal worker (PW) (or person being measured 2) collects raw signals detected from the activity meter 4 attached to the PW (1). The collected detected raw signals are stored temporarily in the memory unit (unit for storing waveform data output from the sensor). The detected raw signals are read out to perform the foregoing steps (2) to (6). The results of the steps lead to business improvement (improvement in working activity process and procedure) of each individual personal worker PW (or person being measured 2). The present embodiment is not limited to these steps. The personal worker PW (or person being measured 2) can be provided with service (7) such as an instruction about the next activity using a glasses-type wearable terminal (drive device) 1100 (refer to a detailed description using FIG. 38 et seq).

An example of use in WNS with reference to FIG. 1 has been described as an application example of the present embodiment. The present embodiment is not limited to the example but can be applied to a social infrastructure market, a personal market, a health care market, a production/management market (design/manufacturing/inspection site) and the like.

As for the social infrastructure market, for example, the present embodiment can be applied to construction environment such as transportation, bridges and buildings, a supply market of public consumer goods such as electricity, water and gas, a financial industry markets related to banking, securities, non-life insurance, etc. As for the personal market, it can be applied to a medical practice and a nursing care field.

The following is a description of each configuration of the behavior estimating system 52. The hardware configuration of the signal processing system according to the present embodiment shown in FIG. 12 includes the activity meter 4, a sensor device 6, an edge device 42 and a server 40. The sensor device 6 is fixed to a predetermined object (e.g., dolly 122) other than human beings, as will be described later with reference to FIG. 16. Wired or wireless communication line is configured between the activity meter 4 and edge device 42, between the sensor device 6 and edge 42 device and between the edge device and server 40 to allow information communications therebetween.

The edge device 42 and the server 40 cooperatively perform estimation result processing and service providing control described later. The edge device 42 also collects and organizes results (contents of transmission information 30) of processing performed by the activity meter 4 and a signal processing unit 60 in the interior of the sensor device 6.

The functional configuration of the signal processing system shown in FIG. 12 includes the behavior estimating system 52, a service control unit 58, a position detecting signal generation unit 46 and a control unit 48. The activity estimating system 52 is configured by the activity meter 4, the sensor device 6 and part of the edge device 42.

FIG. 12 mainly shows the configuration of the activity meter 4. The hardware configuration 62 and functional configuration 64 of the sensor device 6 basically coincide with the configuration of the activity meter 4.

The activity meter 4 (and the sensor device 6) includes a fixing member 50 and the signal detection unit 60. The fixing member 50 has a function of fixing the signal detection unit 60 to part of the body of the person being measured 2 when the activity meter 4 is attached to the person being measured 2. Specifically, the fixing member 50 has a structure of a wristband and can be attached directly to the arm or leg of the person being measured 2 as shown in (a) of FIG. 1. The activity meter 4 is not limited to this structure. For example, the activity meter 4 can be stuck on the human body using an adhesion layer and using part of clothing to be attached to the human body, such as hats, glasses and shoes or part of clothes. As the fixing member 50 to fix the sensor device 6 to the article 8 to be carried, an adhesive layer and part of a string that is used for packaging of the adhesive layer and the article 8 to be carried.

In the embodiment shown in FIG. 12 particular, the whole signal detection unit 60 is built into the activity meter 4 (or the sensor device 6). The hardware configuration 62 of the signal detection unit 60 includes a power generation unit (environmental vibration type or photoelectric conversion type) 68, a power storage unit (battery) 66, the three-axis acceleration sensor 72, the three-axis geomagnetism sensor 74, a signal amplifier group 76, an A/D converter (analog to digital converter) 78, the control unit 80, the memory unit 82 and a communication control unit 84.

As a type of the power generation unit 68, an environment electric type as described later can be used and a photoelectric conversion type such as a solar cell can be used. The power generated by the power generation unit 68 is stored in the power storage unit 66. Using the power stored in the power storage unit 66, the circuits of the signal detection unit 60 are operated.

The three-axis acceleration sensor 72 can obtain acceleration signal waveforms (WX(t), WY(t), WZ(t)) in three axis directions (X-axis, Y-axis and Z-axis directions) which are orthogonal to each other, and the three-axis geomagnetism sensor 74 can detect a direction of the geomagnetism. In one example of the present embodiment, the three axis directions defined in the geomagnetism sensor 74 completely coincide with the three-axis directions (X-axis, Y-axis and Z-axis directions) of the three-axis acceleration sensor 72. In other words, in the interior of the signal detection unit 60 of the activity meter 4 and in the signal detection unit 60 of the sensor device 6, the three axis (X axis, Y-axis and Z-axis) directions which are orthogonal to each other are set in advance.

For convenience of description, the activity meter 4 will be described by way of an example of a three-axis sensor. However, the present embodiment is not limited to the three-axis sensor, but for example, a one-axis sensor or a two-axis sensor can be used, or a three-or-more-axis sensor (e.g., a three-axis acceleration sensor function and a multi-axis angular velocity sensor function are included in the same sensor) can be used.

The three-axis-direction detected raw signals (WX(t), WY(t), WZ(t)) obtained from the three-axis acceleration sensor 72 and geomagnetism sensor 74 are each amplified by the signal amplifier group 76 and then converted to digital signals by the A/D converter (analog to digital converter) 78. The digital signals are stored temporarily in the memory unit 82. The signal detection unit 60 includes the control unit 80 to perform signal processing using the detected raw signals (WX(t), WY(t), WZ(t)) stored in the memory unit 82. The results of the signal processing are transmitted to the edge device 42 as transmission information 30 via the communication control unit 84.

The functional configuration 64 of the signal detection unit 60 will be described below. In detected raw signal generation 90, a process of extracting detected raw signals from the three-axis acceleration sensor 72 and the three-axis geomagnetism sensor 74 and converting the detected raw signals into digital signals by the A/D converter 78 through the signal amplifier group 76, is performed.

The control unit 80 performs reference direction extraction 92 and angle extraction 94 based on results obtained in the detected raw signal generation 90 and detected signal generation (signal processing) 96 after reduction of noise components, using the memory unit 82.

The reference direction extraction 92 means a function of extracting a predetermined reference (direction) using a result of the detected raw signal generation 90. As an example of the function, a gravity direction (e.g., z-axis direction) can be extracted using a detected raw signal waveform to be acquired from the three-axis acceleration sensor 72. Also, a geomagnetic direction (e.g., y-axis direction) can be detected using the raw signals detected from the three-axis geomagnetism sensor 74.

The process of calculating angle θ between a predetermined reference (directions of z axis and y axis corresponding to the predetermined reference) and the coordinate axis (X axis, Y axis and Z axis) preset in the activity meter 4 and sensor device 6, corresponds to the angle extraction 94.

Furthermore, the detected signal generation (signal processing) 96 after reduction of noise components, means a function of processing the detected raw signals (WX(t), WY(t), WZ(t)) using a result of the angle extraction 94 to generate detected raw signals (Wx(t), Wy(t), Wz(t)) after reduction of noise components. The reduced noise components of at least one of the resulting detected raw signals (Wx(t), Wy(t), Wz(t)) are less than those of the detected raw signals (WX(t), WY(t), WZ(t)).

Then, the result is transmitted from the activity meter 4 to the edge device 42 via the communication control unit 84. The transmission information 30 to be transmitted at this time includes extracted angle information 32 and detected signal information 34 whose noise components are reduced.

The system according to the present embodiment shown in FIG. 12 includes the communication control unit 84 together with the activity meter 4 and the sensor device 6, each having a wireless communication function. Using the wireless communication function, the position of a person being measured can be detected in the same manner as a Global Positioning System (GPS).

The position detecting signal generation units 46 controlled by the control unit for position detecting signal generation of the edge device 42 are distributed in different locations of (A) to (D). Transmission time information is continuously transmitted wirelessly from the locations of (A) to (D). A difference in time at which the communication control unit 84 receives time information from each of the locations of (A) to (D) is detected to make it possible to detect a place on which the activity meter 4 (or sensor device 6) is disposed in real time.

The combination of the position information and the detected signals (Wx(t), Wy(t), Wz(t)) whose noise components are reduced, obtained from the three-axis acceleration sensor 72 and the three-axis geomagnetism sensor 74, as described above, brings about the advantage that the position can be detected with high accuracy.

The behavior estimation engine 56 of a behavior estimation unit 54 of the edge device 42 performs behavior estimation based on the transmission information 30 transmitted from the sensor devices 4 and 6 (or state estimation and request estimation of the person being measured 2). Then, based on a result of the estimation, service providing and business improvement 10 are proposed in the service control unit 58.

Specifically, when the result (behavior estimation result 16) obtained from the behavior estimation engine 56 is transmitted to the server 40, the contents of a service instruction 11 is returned from the server 40. Based on the contents of the service instruction 11, a drive device 44 is operated from the edge device 42 using wireless communication, and service providing is performed to the person being measured 2 or other users.

The drive device 44 includes an electric motor or a light-emitting device, a display device, a speaker, etc., to drive the electric motor, perform emission and display, output voice, and the like in accordance with an operation from the edge device 42.

FIG. 13 shows a system according to another embodiment regarding the signal processing system shown in FIG. 12. In the system (signal processing system) according to the embodiment shown in FIG. 13, only the detected raw signal generation 90 and the position detection 98 are performed in the activity meter 4 (or in the sensor device 6) in the functional configuration 64 of the position detection unit 60.

On the edge device 42 side, the foregoing reference direction extraction 92, angle extraction 94 and detected signal extraction after noise component reduction (signal Processing) 96, which are included in the functional configuration 64 of the signal detection unit 60, are performed.

Adapting to the function sharing (function dispersion between the activity meter 4/sensor device 6 and the edge device 42), only detected position information 38 and detected raw signal information 36 is transmitted from the activity meter 4 or the sensor device 6 to the edge device 42 as the transmission information 31.

As a description corresponding to the above function sharing, a communication control unit 86 and a control unit 81 included in part of the hard configuration 62 of the signal detection unit 60, and the memory unit 83 are specified particularly in the edge device 42. Though not shown explicitly in FIG. 12, in the signal processing system shown in FIG. 12, too, the edge device 42 includes the communication control unit 86, control unit 81 and memory unit 83.

More specifically, in the system (signal processing system) according to the embodiment shown in FIG. 13, the detected position information 38 and the detected signal information 36 transmitted from the activity meter 4 (or the sensor device 6) are stored temporally in the memory unit 83 through the communication control unit 86. Then, the control unit 81 of the edge device 42 performs signal processing using the detected raw signals (WX(t), WY(t), WZ(t)) stored in the memory unit 83. The detected signals (Wx(t), Wy(t), Wz(t)) whose noise components are reduced, obtained by the signal processing are also stored in the memory unit 83.

Processing the detected raw signals (WX(t), WY(t) and WZ(t)) collected from the three-axis acceleration sensor 12 and the three-axis geomagnetism sensor 74 in the edge device 42, the functions of the activity meter 4 and the sensor device 6 can be simplified. This brings about the advantage that not only the activity meter 4 or the sensor device 6 alone, but also the entire signal processing system can be made inexpensively.

Then, the behavior estimation engine 56 that is built into the behavior estimation unit 54 of the edge device 42 performs a state estimation process or a behavior estimation process of the person being measured 2 and a request estimation process (or the person being measured 2 or the other users) using the detected signals (Wx(t), Wy(t), Wz(t)) whose noise components are reduced, which are stored in the memory unit 83.

The contents of the hardware configuration 62 (communication control unit 86, control unit 81 and memory unit 83) belonging to the signal detection unit 60 set in the edge device 42 also serve as the hardware configuration 63 that performs the process of the behavior estimation unit 54.

Then, the behavior estimation result 16 obtained from the behavior estimation engine 56 of the behavior estimation unit 54 of the edge device is transmitted to the server 40. Then, the service 40 uses the result to examine the contents of service providing. After that, the service 40 performs service instruction 11 to the edge device 42.

The contents other than those described above coincide with the contents that have already been described with reference to FIG. 12.

As described with reference to FIG. 12, the three-axis (X axis, Y axis and Z axis) directions orthogonal to each other are preset in the interior of the signal detection unit 60 of the activity meter 4 and in the interior of the signal detection unit 60 of the sensor device 6. The relationship between the three-axis directions and predetermined criteria (e.g., the gravity direction along the z axis and the geomagnetism direction along the y axis) will be described in detail with reference to FIGS. 14, 15 and 16.

Figure 14:
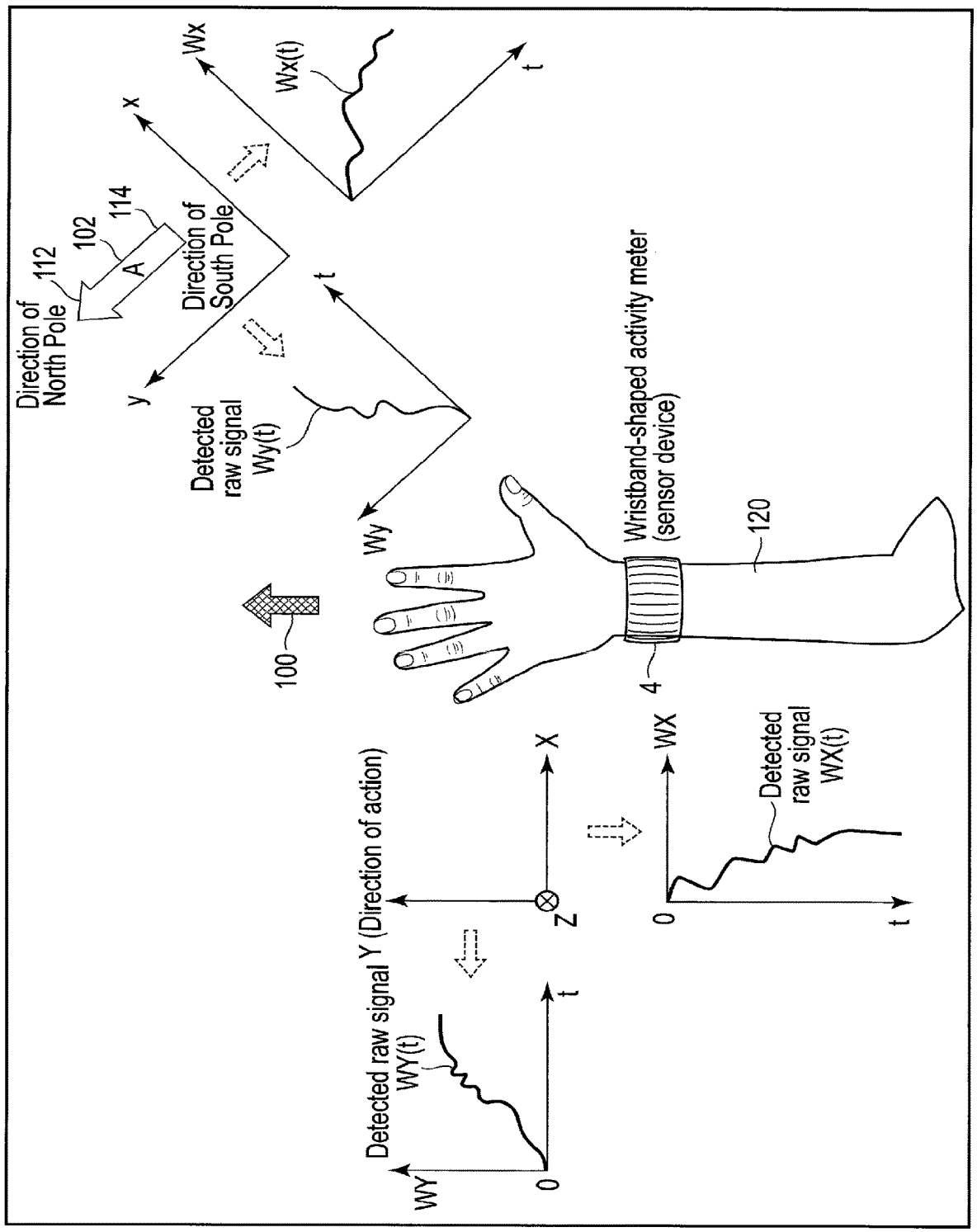
FIG. 14 is an illustration of the relationship between criterion A (geomagnetism direction) and the coordinate axis along an activity meter.

For example, as shown in FIG. 14, the direction toward the middle finger of the person being measured 2 from the arm 120 thereof equipped with the activity meter 4 is set to a Y axis. For convenience of description, the direction of action 100 applied when the person being measured 2 pushes the dolly (the direction in which the person being measured 2 exerts force) is caused to coincide with the Y-axis direction.

The axial direction perpendicular to the back of a hand of the person being measured is set as the Z-axis direction and the direction orthogonal to the Y and Z axes (direction from the little finger of the person being measured 2 toward the thumb thereof) is set as the X axis. In accordance with these coordinate axes, the three-axis acceleration sensor 72 outputs acceleration waveforms (detected raw signals WX(t), WY(t) and WZ(t)) in the X-axis direction, Y-axis direction and Z-axis direction.

At the same time, the three-axis geomagnetism sensor 74 outputs field intensity signals in the X-axis, Y-axis and Z-axis directions (which can be described as WX(t), WY(t) and WZ(t) that mean the detected raw signals or (WX*(t), WY*(t), WZ*(t)) to be distinguished from the acceleration waveforms).

On the other hand, the direction along criterion A (geomagnetism direction) 102 is defined as the y axis (direction from the South Pole 114 to the North Pole 112). The direction from the west to the east is also defined as the x axis. In most cases, the Y and y axes do not coincide with each other, and the waveforms of Wx(t) and Wy(t) are not directly detected as raw signals because the Y and y axes are inclined to each other.

For convenience of description, a case where the X-axis and x-axis coincide with each other will be described with reference to FIG. 15. When the dolly 122 is moved toward the north on the floor surface 128, the movement direction of the dolly 122 coincides with the y-axis direction. If the z axis is defined with the gravity direction as criterion B_104, the y-axis and z-axis are orthogonal to each other.

Figure 15:
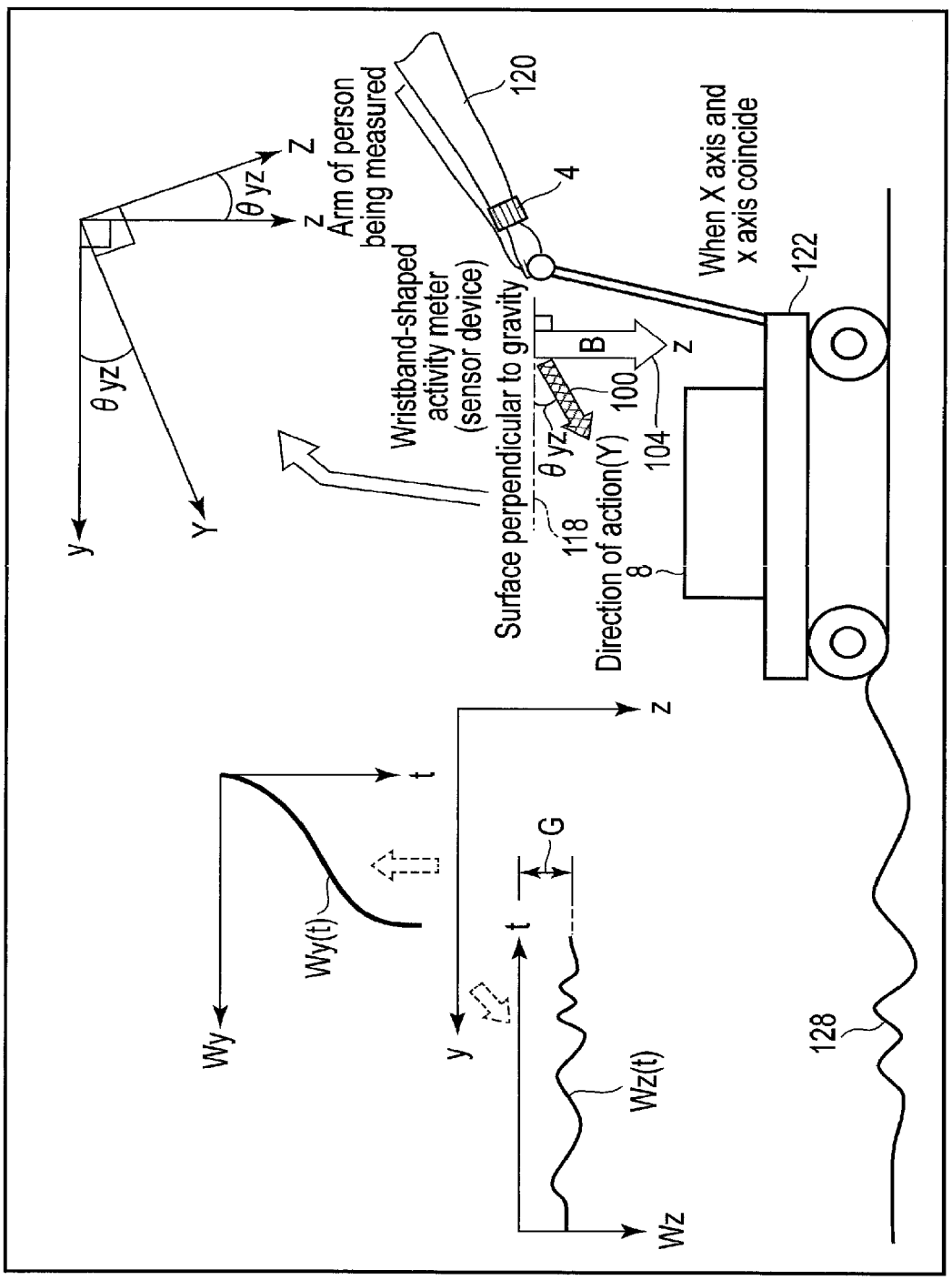
FIG. 15 is an illustration (1) of the relationship between criterion B (gravity direction) and the coordinate axis along an activity meter.

As shown in FIG. 15, the direction in which the person being measured 2 pushes the dolly 122 (action direction 100 of the Y axis) has an inclination of θyz relative to a surface 118 perpendicular to the gravity. Since the Y-axis direction and Z-axis direction are orthogonal to each other as described above, an inclination angle between the z axis and Z axis is also θyz.

The time change of a virtual acceleration waveform Wy(t) to be obtained in the y-axis direction is shown on the right side of FIG. 15. When the person being measured 2 first start to push the dolly 122 in the stationary state (Wy(t)=0), the Wy(t) waveform rises as time elapses in accordance with the start of movement of the dolly 122.

The time change of a virtual acceleration waveform to be obtained in the gravity direction (z-axis direction) is represented by Wz(t). Since constant gravitational acceleration is always applied to the activity meter 4, a DC component corresponding to gravitational acceleration G is always added to Wz(t).

If there is an irregularity in the floor surface 128 on which the dolly 122 moves, an acceleration component (noise component) corresponding to the irregularity is mixed in Wz(t) in response to the movement of the dolly 122.

The Wy(t) waveform or Wy(t) waveform shown on the right side of FIG. 15 cannot be collected directly as a detected raw signal from the three-axis acceleration sensor 72 (or three-axis geomagnetism sensor 74). If, however, the above angle θyz is used, it is possible to calculate Wz(t) and Wy(t) from the detected raw signals WZ(t) and WY(t) that can be collected directly from the three-axis acceleration sensor 72 (or three-axis geomagnetism sensor 74).

In the present embodiment (signal processing system), criterion A (geomagnetism direction) 102 and criterion B (gravity direction) 104 are extracted using raw signals WX(t), WY(t) and WZ(t) detected from different sensors of the sensor device (activity meter) 4 and the sensor device 6. To do this, it is necessary to extract a predetermined criterion (direction) with high accuracy (by reducing noise components mixed in the detected raw signals).

Figure 16:
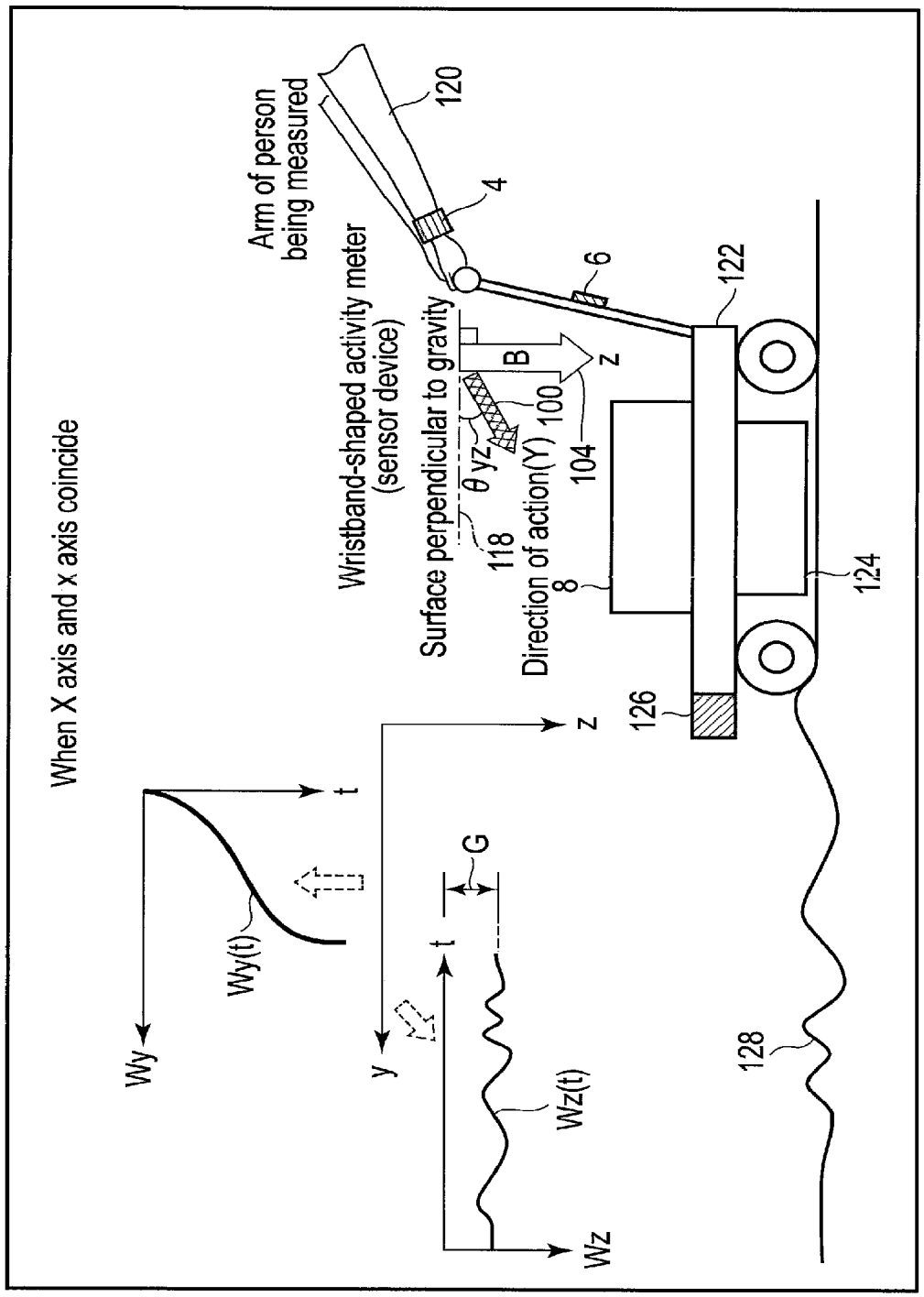
FIG. 16 is an illustration (2) of the relationship between criterion B (gravity direction) and the coordinate axis along the activity meter.

An example of application to FIG. 15 is shown in FIG. 16. In FIG. 15, signal processing/behavior estimation of the person being measured 2 is performed using the raw signals detected from the activity meter 4 attached to the arm 120 of the person being measured 2 to lead to business improvement (improvement in working process) through the behavior history analysis of the person being measured 2 and to provide necessary services. The behavior estimation of the person being measured 2 is not limited to this. For example, the sensor device 6 can be fixed to part of a predetermined object such as the dolly 122 (by pasting or the like), and signal processing/behavior estimation is performed by the detected raw signals alone collected from the sensor device 6 to perform a behavior history analysis/business improvement and provide services. In addition, the raw signals detected from the activity meter 4 and the raw signals detected from the sensor device 6 can be combined. This combination brings about the advantage of increasing the behavior estimation of the person being measured 2 to allow more appropriate business improvement planning and service providing.

It has been described with reference to FIGS. 12 and 13 that in the system of the present embodiment (signal processing system), the edge device 42 operates the drive device 44 to allow service to be provided (to the person being measure 2 or other users). To provide the service, an electric motor (drive device) 124 corresponding to the drive device 44 and a light emitting device or a loudspeaker (drive device) 126 are provided.

The light emitting device emits light or the loudspeaker outputs voice as the electric motor 124 moves based on the service instruction 11 from the server 40, which has determined "the person being measured 2 is moving the dolly 20" as the behavior estimation result 16 in the behavior estimation engine 56 (FIGS. 12 and 13). When the electric motor 124 automatically starts to move during the dolly movement 20 of the person being measured 2, the advantage capable or reducing the burden on the person being measured 2 who is moving the dolly is produced. The light emission of the light emitting device or the voice output from the loudspeaker makes it possible to automatically "call attention" to a third party as the dolly moves. This also brings about the advantage that the dolly can be moved safely (prevention of inadvertent contact with a third party).

A description of a route through which noise components are mixed into the detected raw signals will be given first. As shown in FIG. 12 or 13, in the interior of the signal detection unit 60, faint signals obtained from the sensors 72 and 74 are amplified by the signal amplification group 76 and converted into digital signals through the A/D converter 78.

Below is a description of a method of generating signal components in a predetermined direction from raw signals WZ(t), WY(t) and WX(t) detected from the sensors 72 and 74 using angle θ extracted by the above method.

FIG. 17 shows a change over time in signals detected directly or indirectly when the person being measured 2 pushes the dolly 122 and the dolly 122 starts to move. For the sake of convenience, assume here a way of taking the same coordinate axis as in FIG. 16 (a case where the X and x axes coincide with each other).

When the dolly 122 starts to move, the acceleration waveform Wy(t) in the moving direction (y-axis direction) of the dolly increases as time elapses as shown in (a) of FIG. 17. On the other hand, the acceleration waveform Wz(t) in the gravity direction (z-axis direction) is added to a gravity acceleration component G (DC component) that always exists, and an acceleration change corresponding to the irregularities of the floor surface 128 appears ((b) of FIG. 17).

In addition, as described above with reference to FIG. 15, the Y-axis direction set in advance in the activity meter 4 inclines only angle θyz relative to the surface 118 perpendicular to the gravity. Thus, the noise component of Wz(t) (corresponding to the irregularities of the floor surface 128) is mixed into the detected raw signal WY(t) in accordance with the angle θyz.

When the person being measured 2 of average height pushes the dolly 122, θyz is represented by θs. The detected raw signal "WY(t)|θyz=θs" collected from the Y-axis direction of the acceleration sensor 72 of the activity meter 4 when θyz is equal to θs have a waveform shown in (d) of FIG. 17.

When the person being measured 142 who is smaller than average pushes the dolly 122, θyz is smaller than θs. In this case, the amount of mixing of the noise component of Wz(t) (corresponding to the irregularities of the floor surface 128) into a detected raw signal "WY(t)|θyz<θs" is relatively small, with the result that the waveform shown in (c) of FIG. 17 is obtained.

When the person being measured 144 who is taller than average pushes the dolly 122, θyz is larger than θs. In this case, the amount of mixing of the noise component of Wz(t) (corresponding to the irregularities of the floor surface 128) into a detected raw signal "WY(t)|θyz>θs" is relatively large, with the result that the waveform shown in (e) of FIG. 17 is obtained.

In the present embodiment, some signal processing is applied to the detected raw signal shown in (c) or (e) of FIG. 17 to reduce the influence of the height of the person being measured 2. Performing the behavior estimation (or situation estimation) of the person being measured 2 using a result of the signal processing to reduce the influence of the height of the person being measured 2 as described above, brings about the advantage of increasing the determination accuracy of the behavior estimation (or situation estimation).

As a method to reduce the influence of the height of the person being measured 2, the detected raw signal shown in (c) or (e) of FIG. 17 can be converted into a detected signal "WY(t)|θyz=θs" when θyz is equal to θs to perform behavior estimation (or situation estimation).

The present embodiment is not limited to the foregoing method. For example, the detected raw signal shown in (c) or (e) of FIG. 17 can be converted into a detected raw signal Wy(t) when θyz is equal to 0 to perform behavior estimation (or situation estimation).

In the system (behavior estimating system 52) according to the present embodiment, behavior estimation is performed by matching a waveform (correct waveform) to be a basis of the behavior estimation and the actual waveform, but specifically, any extension/contraction matching technique can be adopted. As an example of the extension/contraction matching technique, a DP matching technique (dynamic programming matching technique) will be described with reference to FIGS. 18 to 20. Note that the system (signal processing system) of the present embodiment is not limited to the matching technique, but any matching technique can be used for the estimation process.

An example of the standard measured acceleration waveform (sample data) which is measured in advance is shown in (a) of FIG. 18. When the person being measured 2 pushes the dolly 122, which is in a stationary state at the beginning, and the dolly 122 starts to move, the acceleration in the moving direction (y-axis direction) of the dolly 122 (y-axis direction) increases from "0" as time elapses. When the acceleration becomes closer to a fixed one, the acceleration to be detected decreases ((a) of FIG. 18).

The horizontal axis memory of FIG. 18 represents a cycle period (e.g., 50 mS). An expedient value of the standard measured acceleration waveform (sample data) collected for each cycle period is explicitly shown in each graph of FIG. 18.

Consider the case where the person being measured 2 of the height different from the average height pushes the dolly 122 slowly. The behavior speed (work speed) at which the person being measured 140 of average height starts to push the dolly 122 to collect the standard measured acceleration waveform (sample data) in advance, is defined as "standard speed". The detected raw signal WY(t) in the Y-axis direction when the behavior speed (work speed) at which the person being measured 2 starts to push the dolly 122 is slower than the "standard speed" is shown in (b) of FIG. 18.

As described with reference to FIG. 2, the low-frequency component (DC component) of Q42L due to gravity is always superimposed on the detected raw signal WY(t) in the Y-axis direction. As compared with the standard measured acceleration waveform (sample data) ((a) of FIG. 18), the person being measured 2 pushes the dolly 122 slowly this time. Therefore, the amount of change in acceleration in (b) of FIG. 18 is smaller than the standard measured acceleration waveform (sample data).

After the gravity component Q42L is subtracted from the detected raw signal WY(t) in (b) of FIG. 18, it is converted into the converted standard measured acceleration using the equation (5) or (7). The resultant amplitude value is standardized so as to coincide with that in (a) of FIG. 18, and the characteristics of the standardized amplitude value are shown in (c) of FIG. 18.

The maximum signal amplitude in (c) of FIG. 18 after the amplitude value is standardized coincides with the standard measured acceleration waveform (sample data) in (a) of FIG. 18. Since, however, the person being measured 2 pushes the dolly 122 slowly, the change in signal in the time axis direction is small (slow).

In the extension/contraction matching technique employed in the system (behavior estimating system 52) according to the present embodiment, a difference in extension/contraction in time axis direction between (a) and (c) of FIG. 18 can automatically be corrected to calculate a degree of matching between them. Since, therefore, pattern matching can be performed while correcting a difference in behavior speed of the person being measured 2 or a difference in processing speed corresponding to a fixed object obtained by the sensor device 6, the advantage that the accurate pattern matching can be determined irrespective of the variations of the behavior speed (processing speed) is brought about.

Figure 19:
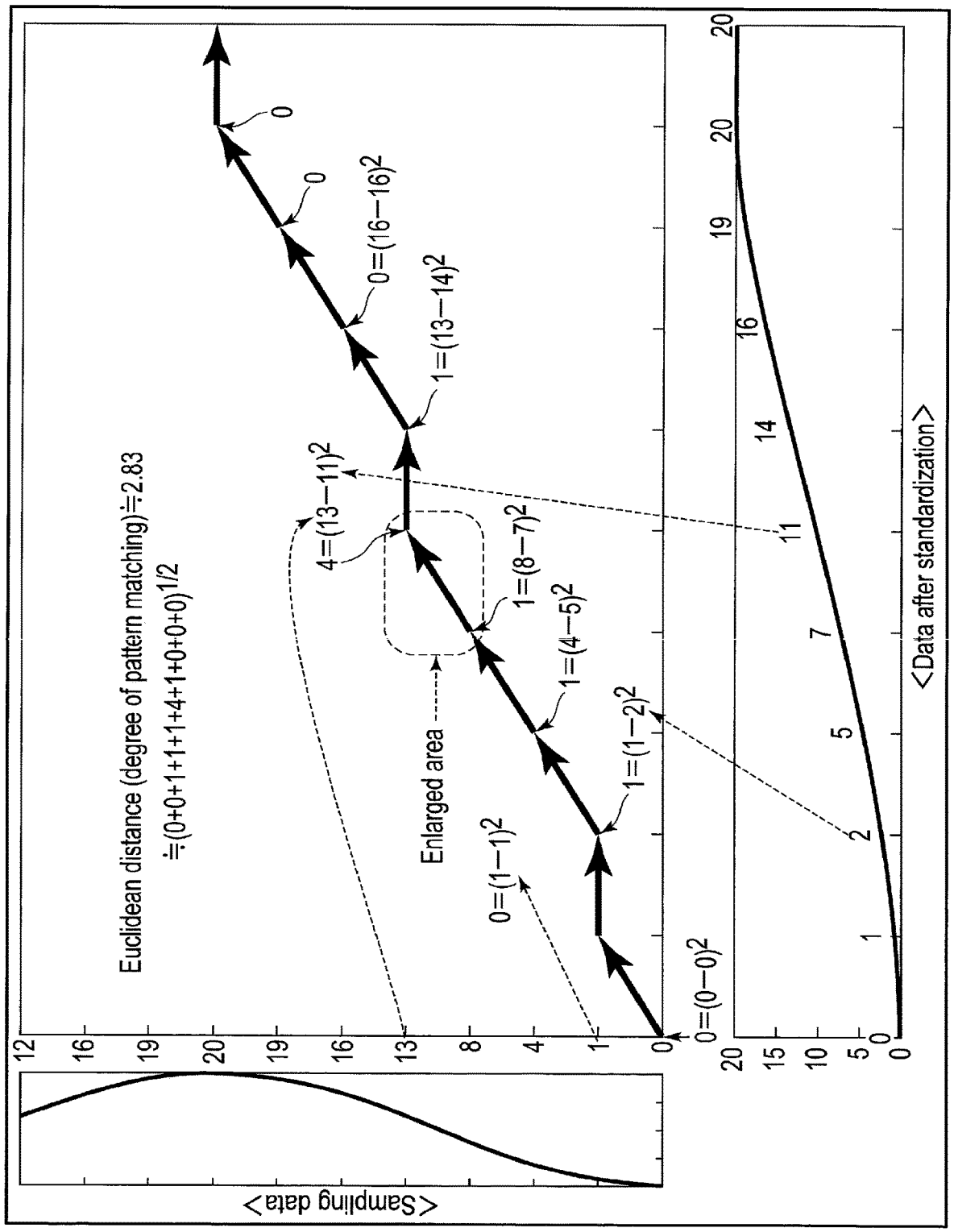
FIG. 19 is an illustration of a pattern matching method in which variations in behavior are taken into consideration.

The waveform of (c) of FIG. 18 is transferred in the horizontal-axis direction of FIG. 19 and the waveform of (a) of FIG. 18 is transferred in the vertical-axis direction of FIG. 19. In FIG. 19, the pattern amplitude in the horizontal-axis direction and the pattern amplitude in the vertical-axis direction coincide with each other. In the DP matching technique (described above) which is a method of comparing similarities of data in series, a connection (arrow) between intersections at which the amplitude values are similar to each other is considered to be the optimal route, and a sequential search is made for the optimal route. This search for the optimal route corresponds to a process of absorbing variations in the behavior speed (processing speed).

Figure 20:
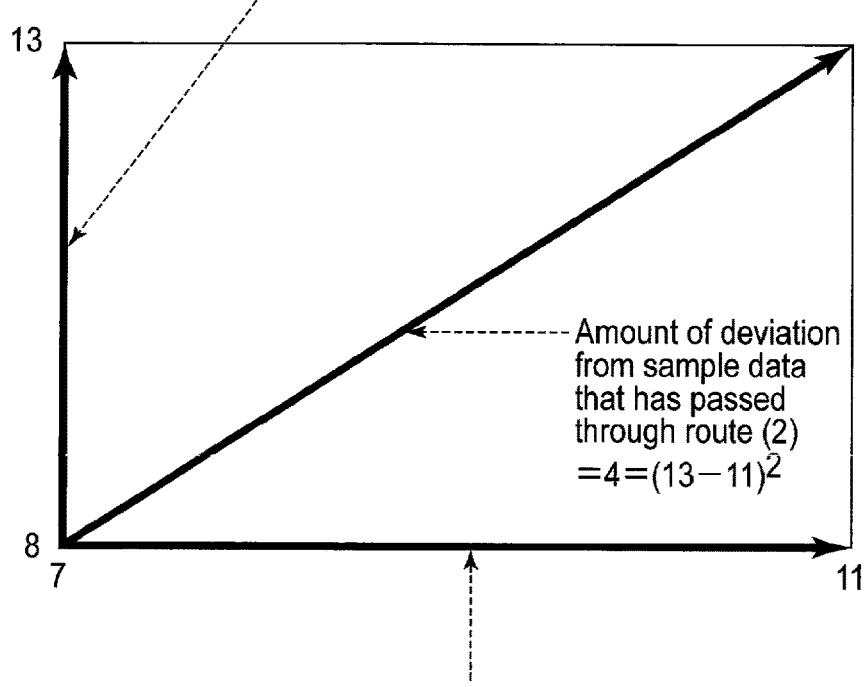
FIG. 20 is an illustration of an optimum route selection method.

A method for searching for the foregoing optimal route will be described below. FIG. 20 is an enlarged view of the "enlarged area" shown in FIG. 19. In the example of FIG. 20, when the elapsed time advances only a cycle period, the amplitude changes from "7" to "11" in the horizontal-axis direction, whereas the amplitude changes from "8" to "13" in the vertical-axis direction. At this time, there are three candidates for the route. Specifically, the route (1) is a movement in the horizontal direction, the route (2) is a movement in the obliquely upward direction, and the route (3) is a movement in the vertical direction.

First, a value of the square of the amount of deviation from the sample data that has passed through the route (1) is calculated. The amplitude value in the vertical-axis direction after it has passed the route (1) remains "8". On the other hand, the amplitude value in the horizontal-axis direction changes from "7" to "11". As a result, the square of the amount of deviation of the amplitude value after it has passed through the route (1) is 9 $(=(8-11)^2)$.

Then, in the movement in the diagonally upward direction in the route (2), the amplitude value in the horizontal-axis direction after it has passed through the route (2) becomes "11" and the amplitude value in the vertical-axis direction becomes "13". As a result, the square of the amount of deviation between the two amplitude values is 4 $(=(13-11)^2)$.

Similarly, when it has passed through the route (3), the amplitude value in the horizontal-axis direction remains "7", but the amplitude value in the vertical-axis direction changes from "8" to "13". As a result, the square of the amount of deviation between data after it has passed is 36 $(=(13-7)^2)$.

In this DP matching technique, a route in which the square value of the amount of deviation after it has passed through the route is the smallest, is selected automatically. In the example shown in FIG. 20, therefore, the route (2) with the smallest square value "4" of the amount of deviation is automatically selected. As the optimal route is automatically selected in this way, matching between patterns in which the extension/contraction varies in the time axis direction can be taken as in the relationship between (a) and (c) of FIG. 18.

The following is a description of a method for calculating an amount of error between the standard measured acceleration and the standard measured acceleration waveform (sample data), which have been transformed during the statistical processing storage period. The square values of the amount of deviation during the optimal route passing, which are calculated for each square (cycle period) shown in FIG. 20, are totaled in the statistical processing storage period. The value of the root of the total value is called "Euclidean distance" indicating the degree of pattern matching. In the example of FIG. 19, the Euclidean distance is 2.83.

When there are two or more behavior estimation candidates for the person being measured 2 (standard measured acceleration waveforms (sample data) of different types are prepared), the Euclidean distance between the transformed standard measured accelerations for each of the different standard measured acceleration waveforms (sample data). It is determined that the behavior of the person being measured 2 is similar to the behavior estimation candidate with the shortest Euclidean distance.

On the other hand, in the case where behavior estimation as to whether the behavior of the person being measured 2 coincides with the dolly movement 22 is performed as shown in (b) of FIG. 1, only the standard measured acceleration waveform (sample data) is prepared in advance. Therefore, in this case, the Euclidean distance between the above standard measured acceleration waveform (sample data) and the transformed standard measured acceleration is calculated to perform behavior estimation (or an estimation process such as state estimation) according to whether the value of the calculated Euclidean distance is a predetermined threshold value or less.

Another embodiment in which the behavior estimating system 52 described with reference to FIGS. 12 and 13 is achieved by another hardware configuration, is shown in FIG. 21. The behavior estimating system 52 includes a signal detection unit 60 and a behavior estimation unit 54. The signal detection unit 60 includes a memory unit (output waveform data storage unit) 82 and some of an output waveform data/acceleration extraction unit 160, an angle extraction unit 164, a coordinate transformation unit 166, a filter unit 162 and a control unit (control management unit) 80.

Also, the behavior estimation unit 54 includes a standard person-being-measured data (sample data targeted for matching comparison) storage unit 170 and some of a feedback data storage unit 176, a feedback data processing unit 178, a threshold value change determination unit 182, a threshold value change unit 184, an operation determination unit 172, an operation determination threshold value storage unit 174 and a control unit (control management unit) 80.

The memory unit (output waveform data storage unit) 82 stores data (detected raw signals) measured by the activity meter 4. The memory unit (output waveform data storage unit) 82 corresponds to the memory unit 82 shown in FIG. 12 or 13.

The output waveform data/acceleration extraction unit 160 fulfills the function of the detected raw signal generation 90 shown in FIG. 12 or 13. A specific hardware configuration regarding the output waveform data/acceleration extraction unit 160 corresponds to the three-axis acceleration sensor 72, signal amplification group 76 and A/D converter 78 shown in FIG. 12 or 13.

On the other hand, the function of the filter unit 162 coincides with that of the low-pass filtering process 138 described with reference to FIG. 12. In other words, the filter unit 162 extracts gravitational acceleration components Q41L, Q42L and Q43L from the acceleration values output from the output waveform data/acceleration extraction unit 160. As the contents of the low-pass filtering process, prior art low-pass filtering characteristics can be used. The present embodiment is not limited to the low-pass filtering characteristics. For example, a filtering method to acquire the average value can be used. The function of a combination of the angle extraction unit 164 and the filter unit 162 shown in FIG. 21 corresponds to the reference direction extraction 92 and the angle extraction 94 shown in FIG. 12 or 13. In other words, the angle extraction unit 164 calculates angle θyz of the arm 120 to push the dolly 122 of the person being measured 2 (see FIG. 16). For this angle extraction, as described above, the angle θyz is calculated using a trigonometric function and the gravitational components contained in the acceleration values measured by the wristband-shaped activity meter (sensor device) 4 attached to the arm 120 of the person being measured.

The coordinate transformation unit 166 also fulfills the function of the detected signal generation (signal processing) 96 from which noise components are reduced in FIG. 12 or 13. In other words, the measured acceleration waveforms (detected raw signals) WX(t), WY(t) and WZ(t) obtained from the three-axis acceleration sensor 72 are rotationally transformed into standard measured acceleration (signal processing) using equation (5) or (7). In this case, angle dθyz calculated from the angle extraction unit 164 using a gravity value is utilized.

The storage unit 170 of the standard person-being-measured data (sample data targeted for matching comparison) stores the standard measured acceleration waveforms (sample data).

The feedback data storage unit 176 stores data output from the feedback data processing unit, which will be described later.

The error characteristics (or the Euclidean distance characteristics for the standard measured acceleration waveforms (sample data)) between the transformed standard measured acceleration and measured acceleration waveform (detected raw signal) with respect to angle θ(θyz) of the arm 120 of the person being measured 2 have been described with reference to FIG. 8. The characteristics are stored in the feedback data storage unit 176.

The operation determination unit 172 determines whether the person being measured 2 performed the dolly movement 20 at a measurement target time. The characteristics shown in FIG. 8 are used for the determination, and information of the determination threshold value 150 during the behavior estimation of the person being measured is used for the criterion of the determination.

The information of the determination threshold value 150 during the behavior estimation of the person being measured is stored in the operation determination threshold value storage unit 174.

As described with reference to FIG. 8, the Euclidean distance that is compared with an amount of error between the transformed standard measured acceleration and measured acceleration waveform (detected raw signal) with respect to angle θyz of the arm 120 of the person being measured 2 or the standard measured acceleration waveform (sample data) is calculated as appropriate in real time for each cycle. The threshold value change determination unit 182 monitors in real time (for each cycle) whether the above amount of error or Euclidean distance exceeds the determination threshold value 150 during the behavior estimation of the person being measured. If the above amount of error or Euclidean distance exceeds the determination threshold value 150, information is transmitted to the threshold value change determination unit 182 to change the determination threshold value 150.

Then, the threshold value change unit 184 controls a change of the determination threshold value 150 during the behavior estimation of the person being measured, based on the information transmitted from the threshold value change determination unit 182.

As an example of signal processing to be performed in the system (signal processing system) according to the present embodiment, a method for extracting angle θyz of the arm 120 of the person being measured 2 to push the dolly 122 using the detected raw signals WX(t), WY(t) and WZ(t) collected from the three-axis acceleration sensor 72 built in the wristband-shaped activity meter (sensor device) 4 and rotationally transforming it into a detected signal to be obtained when θyz becomes equal to θs, has been described.

At the beginning of this specification of the present embodiment, the basic contents of the present embodiment were itemized as (1) to (7). The following is a description of an example of a method for specifically implementing the contents by the behavior estimating system 52 shown in FIG. 21.

As described above as a method for using results of behavior estimation of the person being measured 2, (7) service can be provided and (6) business (working process) improvement can be proposed. To (7) provide service, real-time property is required for the above behavior estimation.

On the other hand, when (6) business (working process) improvement is proposed, no real-time property is required but the following batch process can be performed. First, a method for performing the behavior estimation with the batch process will be described. As an example of the behavior of the person being measured 2, a description of pushing the dolly 122 by a person being measured with the activity meter 4 attached to the arm 120, will be given.

Then, the processes performed up to the behavior estimation of the person being measured 2 or a series of processes leading to (6) the business improvement (improvement of working process) can be carried out collectively (batch process) by reading data from the memory unit (output waveform data storage unit) 82 (at a later date) after the date from the collection date of behavior data of the person being measured 2.

During the above batch process, the control unit (control management unit) 80 reads the detected raw signals WX(t), WY(t) and WZ(t) from the memory unit (output waveform data storage unit) 82 and transfers them to the angle extraction unit 164.

The angle extraction unit 164 has a function of the low-pass filtering process 138 described with reference to FIG. 3 to calculate values of Q41L, Q42L and Q43L. Then, it calculates θyz and the like using the equations (1) to (3) to obtain dθyz and the like from FIG. 2.

The coordinate transformation unit 166 rotationally transforms the detected raw signals WX(t), WY(t) and WZ(t) (signal processing) using the equation (5) derived from FIG. 4 or the equation (7) derived from FIGS. 4, 9 and 10 to calculate the transformed standard measured accelerations WXs(t), WYs(t) and WZs(t).

As a method for estimating the behavior of the person being measured 2, the methods (A) to (C) (or a combination of the methods) have already been described. Here, an example of using, for the behavior estimation, determination of dispersion and irregularities of the detected signals before and after the (A) rotation transformation (signal processing), will be described.

The operation determination unit 172 shown in FIG. 21 compares a preset predetermined threshold value with an error between the measured acceleration waveforms (detected raw signals) WX(t), WY(t) and WZ(t) and the standard measured accelerations WXs(t), WYs(t) and WZs(t) obtained after the rotation coordinate transformation. When the amount of error falls within the predetermined threshold value, the operation determination unit 172 determines that the person being measured 2 is moving the dolly 122. When it exceeds the predetermined threshold value, the unit 172 determines that the person being measured 2 is not moving the dolly 122.

Simultaneously with the above, the feedback data processing unit 178 extracts the relationship in the amount of error between the measured acceleration waveforms (detected raw signals) WX(t), WY(t) and WZ(t) and the standard measured accelerations WXs(t), WYs(t) and WZs(t) obtained after the rotation coordinate transformation, for each angle $\theta(\theta yz)$ that is formed between the surface 118 perpendicular to the gravity and the action direction (Y-axis direction) 100. A result of the extraction is stored in the feedback data storage unit 176.

Since the foregoing process is a batch process, continuous data of the person being measured 2 for two or three hours, which was measured the day before, or data for one day can collectively be recorded at a time in the feedback data storage unit 176.

After that (at a later data after the date when the extraction result is recorded in the feedback data storage unit 176), the feedback data processing unit 178 statistically analyzes the data recorded in the feedback data storage unit 176 to create a characteristic graph shown in FIG. 8.

In FIG. 8, the determination threshold value 150 at the time of behavior estimation of the person being measured is a constant value irrespective of angle θ. However, the determination threshold value 150 is not limited to the constant value. The determination threshold value 150 can be reset as appropriate according to angle θ.

If the determination threshold value 150 is reset in accordance with angle θ, the threshold value change unit 184 sets the changed threshold value. The changed threshold value corresponding to the reset angle θ is stored in the operation determination threshold value storage unit 174 as appropriate. The threshold value change determination unit 182 determines whether the threshold value change unit 184 needs to reset the threshold value. When the threshold value needs to be reset, its information is transmitted from the threshold value change determination unit 182 to the threshold value change unit 184.

Another embodiment regarding a flow of the process to be performed by the behavior estimating system 52 shown in FIG. 21 will be described with reference to FIGS. 22A to 22C.

When the behavior estimating system 52 starts a process in Step S, the person being measured 140 of average height measures acceleration waveform data obtained when he or she moved the dolly 122 and stores it in the storage unit 170 of the standard person-being-measured data (sample data targeted for matching comparison) as a standard measured acceleration waveform (sample data) in Step A1.

After that, in Step A2, the output waveform data/acceleration extraction unit 160 acquires a detected raw signal (measured acceleration waveform (detected raw signal)) from the person being measured 2.

In Step B1, the filter unit 162 extracts the decomposed components (G41L and G42L) of the gravitational acceleration (see FIG. 3). In Step B2, the angle extraction unit 164 calculates inclination angle $\theta(\theta yz)$ of the arm 120 of the person being measured 2 from Q41L and Q42L obtained above. For this calculation, the equation (1), (2) or (3) derived from FIG. 2 is used. As a method for calculating angle $\theta(\theta yz)$, one of "setting 1: a method for calculating $\theta(\theta yz)$ using the equation (1)", "setting 2: a method for calculating $\theta(\theta yz)$ using the equation (2)" and "setting 3: a method for calculating $\theta(\theta yz)$ using the equation (3)" can be used. The angle calculating method is not limited to the above, but the following can be used: "setting 4: a method using the average value between $\theta(\theta yz)$ values obtained from the equations (1) and (2)" and "setting 5: a method using the average value among $\theta(\theta yz)$ values obtained from the equations (1), (2) and (3).

In Step B3, the coordinate transformation unit 166 rotationally transforms the measured acceleration waveforms (detected raw signals) WX(t), WY(t) and WZ(t) into the transformed standard measured accelerations (signal processing). For the rotation transformation (signal processing), the foregoing equation (5) or (7) is used.

As has already been described, in the system (behavior estimating system 52) according to the present embodiment, there is a relationship of "determination period of behavior estimation" ≥ "statistical processing storage Period" Z "cycle period". One process flow from Step A2 to Step B3 in FIG. 22A means a process of one cycle. Thus, in order to estimate the behavior of the person being measured 2 in the behavior estimating system 52, it is necessary to repeat the cycle at least the number of times corresponding to the "determination period of behavior estimation" at the beginning (for example, when "determination period of behavior estimation" is four seconds and the "cycle period" is 50 mS, it is necessary to repeat the process flow from Step A2 to Step B3 at least eighty times at the beginning).

In Step B5, in response to the above, it is determined whether the above cycle has been repeated only a predetermined number of times. If the number of times does not reach the predetermined number of times, the process flow is advanced (incremented) by one cycle in the output waveform data/acceleration extraction unit 160 to start the next process flow (cycle) from Step A2 to Step B3 (Step B10). On the other hand, if the behavior estimation process can be performed after the cycle is repeated a predetermined number of times, the process flow proceeds to Step B4.

As an example of the behavior estimation process of the person being measured 2 to be performed in Step B4 (in the case of (A) below), the operation determination unit 172 determines whether an error between the measured acceleration waveform (detected raw signal) and the transformed standard measured acceleration satisfies conditions for the threshold value. However, as a specific behavior estimation processing method performed in the system (behavior estimating system 52) according to the present embodiment, one of the following methods (described above) or a combination thereof can be adopted:

(A) Determination of dispersion and irregularity between the detected signals before and after the rotation transformation (signal processing);
(B) Determination of similarity between the transformed standard measured acceleration and the sample data; and
(C) Determination of extraction/contraction matching estimation of scaling between the transformed standard measured acceleration and the sample data.

If the error does not satisfy the condition for the threshold value as a result of the above determination of the behavior estimation, the operation determination unit 172 determines that the person being measured 2 is not moving the dolly 122 at the target time (Step B7).

On the other hand, when the value of the error satisfies the condition for the threshold value as a result of the determination in Step B6, the operation determination unit 172 determines that the dolly is moving at the target time (Step B8). Though not shown, when the behavior of the person being measured 2 is estimated as the dolly movement 20, the edge device 42 and the server 40 propose the business improvement 10 in cooperation with each other if necessary, based on the service providing and the behavior history of the person being measured 2 (FIG. 1 and FIGS. 11 to 13).

The process from Step A2 to Step B7/B8 is repeated until the behavior estimation process or the service providing process is completed. In other words, it is determined in Step B9 whether the process is completed in a section corresponding to the measured data, and when the behavior estimation process or the service providing process is completed, a series of processes is terminated (Step E). When the behavior estimation process or the service providing process is not completed, the flow returns to Step A2 via Step B10.

Figure 22A:
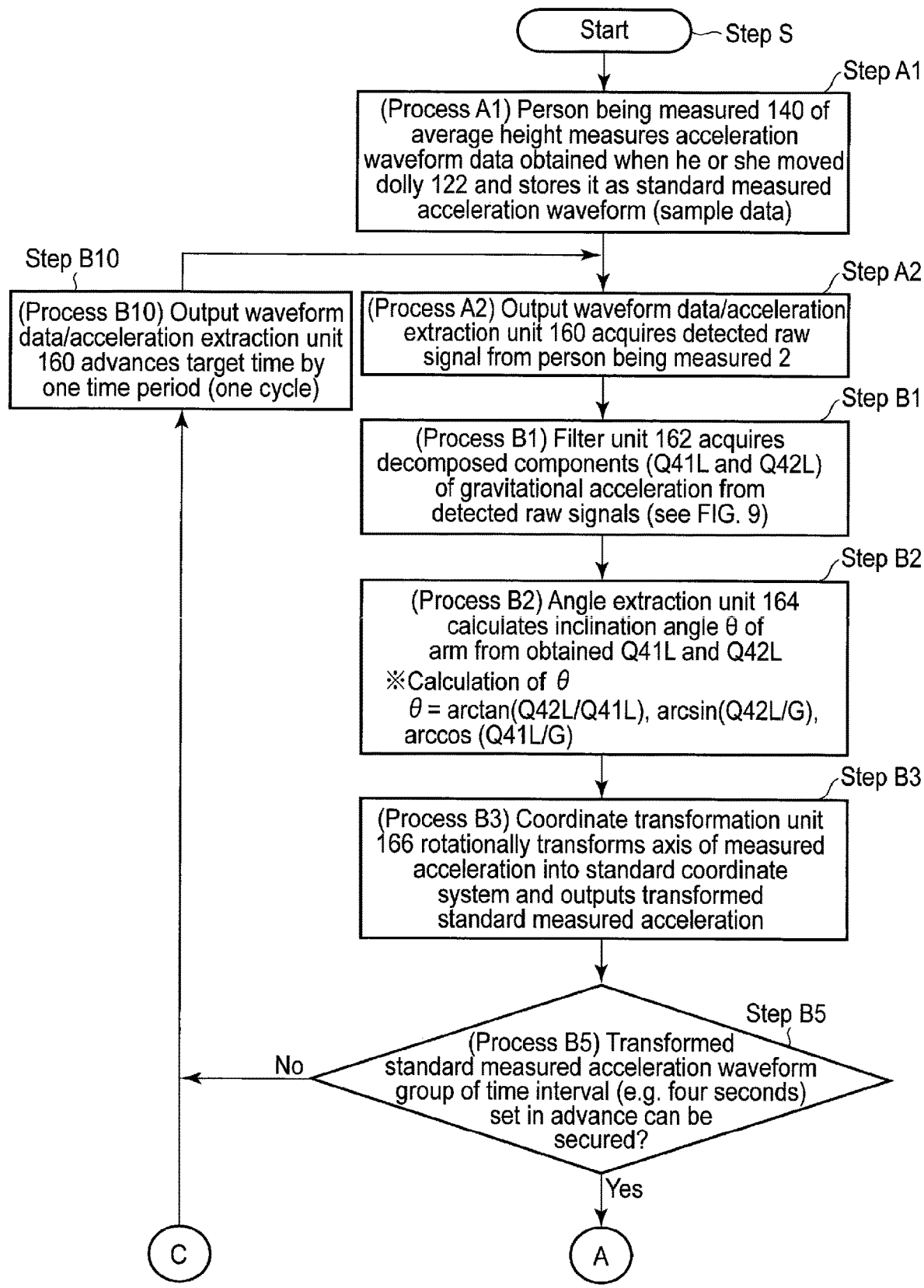
FIG. 22A is an illustration (1) of a processing flow in the system according to the present embodiment.
Figure 22B:
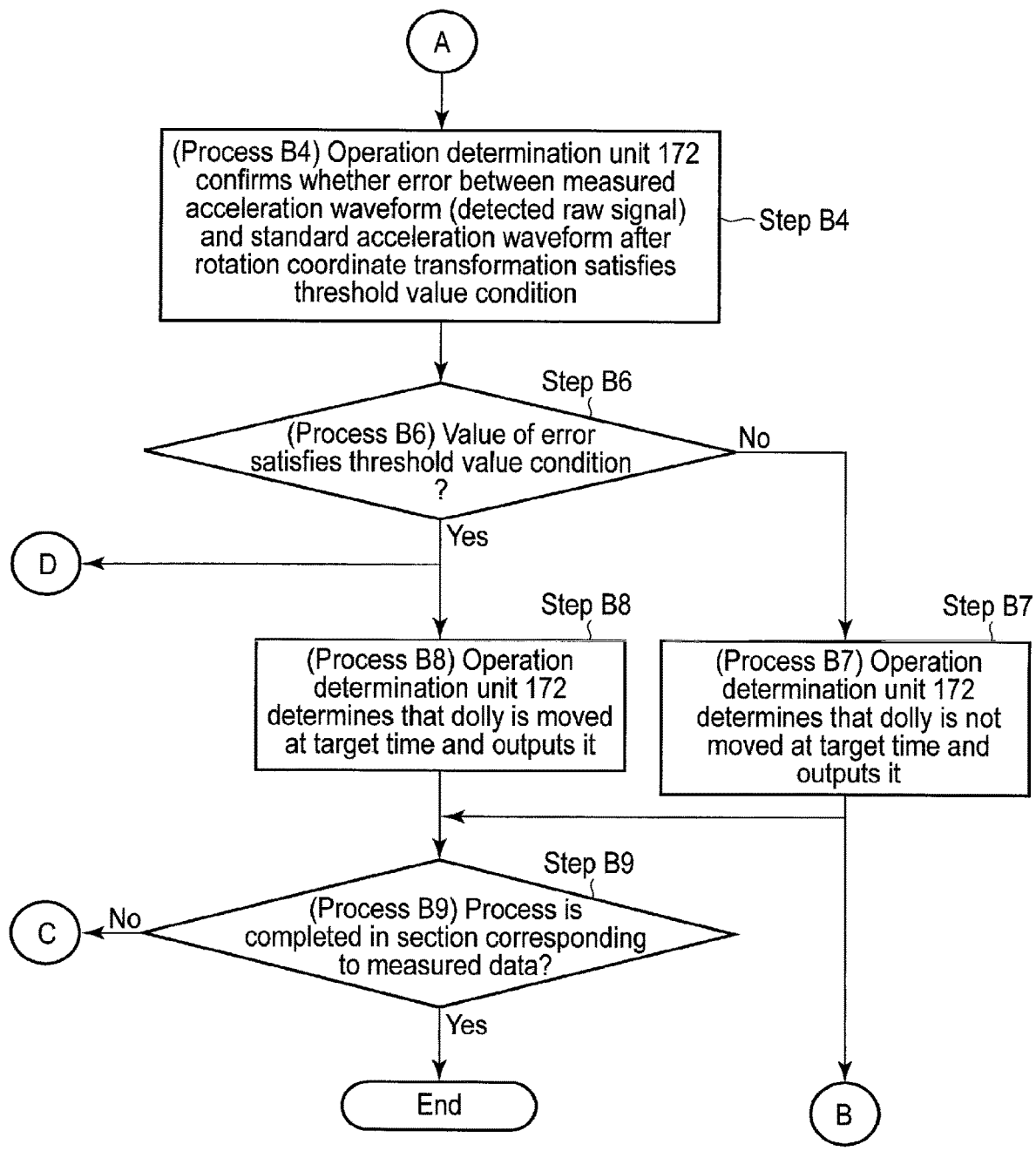
FIG. 22B is an illustration (2) of the processing flow in the system according to the present embodiment.
Figure 22C:
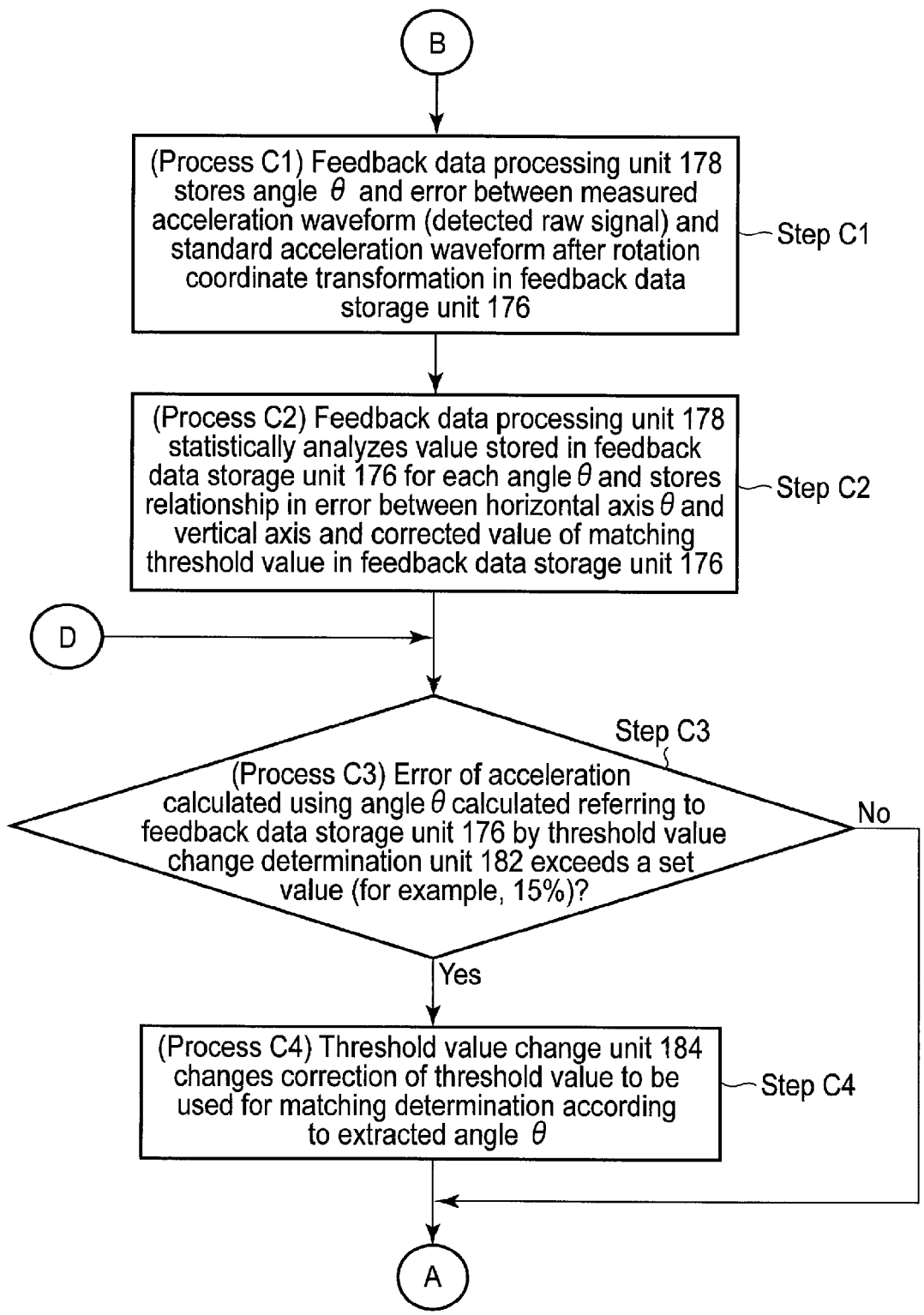
FIG. 22C is an illustration (3) of the processing flow in the system according to the present embodiment.

Furthermore, in association with the series of processes, the determination threshold value 150 is changed as appropriate during the behavior estimation of the person being measured as described with reference to FIG. 8 (FIG. 22C).

Performing the above series of processes in FIG. 22B, the feedback data processing unit 178 calculates the characteristics of an amount of error (Euclidean distance calculated as compared with the standard measured acceleration waveform (sample data)) between the measured acceleration waveform (detected raw signal) and the transformed standard measured acceleration for the angle $\theta(\theta yz)$ of the arm 120 of the person being measured 2 shown in FIG. 8. The result is then recorded in the feedback data storage unit 176 (Step C1).

Then, the feedback data processing unit 178 reads the above characteristic data from the feedback data storage unit 176 to perform a statistical process for each angle $\theta(\theta yz)$ and calculate a corrected value of the determination value 150 (matching threshold value) during the behavior estimation of the person being measured from the result. The calculated corrected value is stored in the feedback data storage unit 176 (Step C2).

The threshold value change determination unit 182 reads the result out of the feedback data storage unit 176 and determines whether the angle error for each angle $\theta(\theta yz)$ exceeds a set value (for example, 15%) (Step C3). If it does not exceed the set value, any special process is not performed but the process after Step B4 is continued.

If it exceeds the set value (determination result in Step C3), the threshold value change unit 184 changes the correction of the threshold value (determination threshold value 150 during the behavior estimation of the person being measured) to be used for matching determination according to the extracted angle $\theta(\theta yz)$ (Step C4).

The foregoing descriptions given with reference to FIGS. 22A to 22C are based upon an example of behavior estimation at the time of the dolly movement 20 of the person being measured 2. However, the system (behavior estimating system 52) according to the present embodiment is not limited to the dolly 20 of the person being measured 2, but can be applied to the behavior estimation for any other behavior. Furthermore, the system of the present embodiment is not limited to the specific person being measured 2. For example, as shown in FIG. 16, state estimation (estimation of the state of a predetermined object) can be performed using a signal detected from the sensor device 6 fixed to a predetermined object ((a) in FIG. 25) such as a portion of the dolly 122 and the article 8 to be carried.

Figure 23:
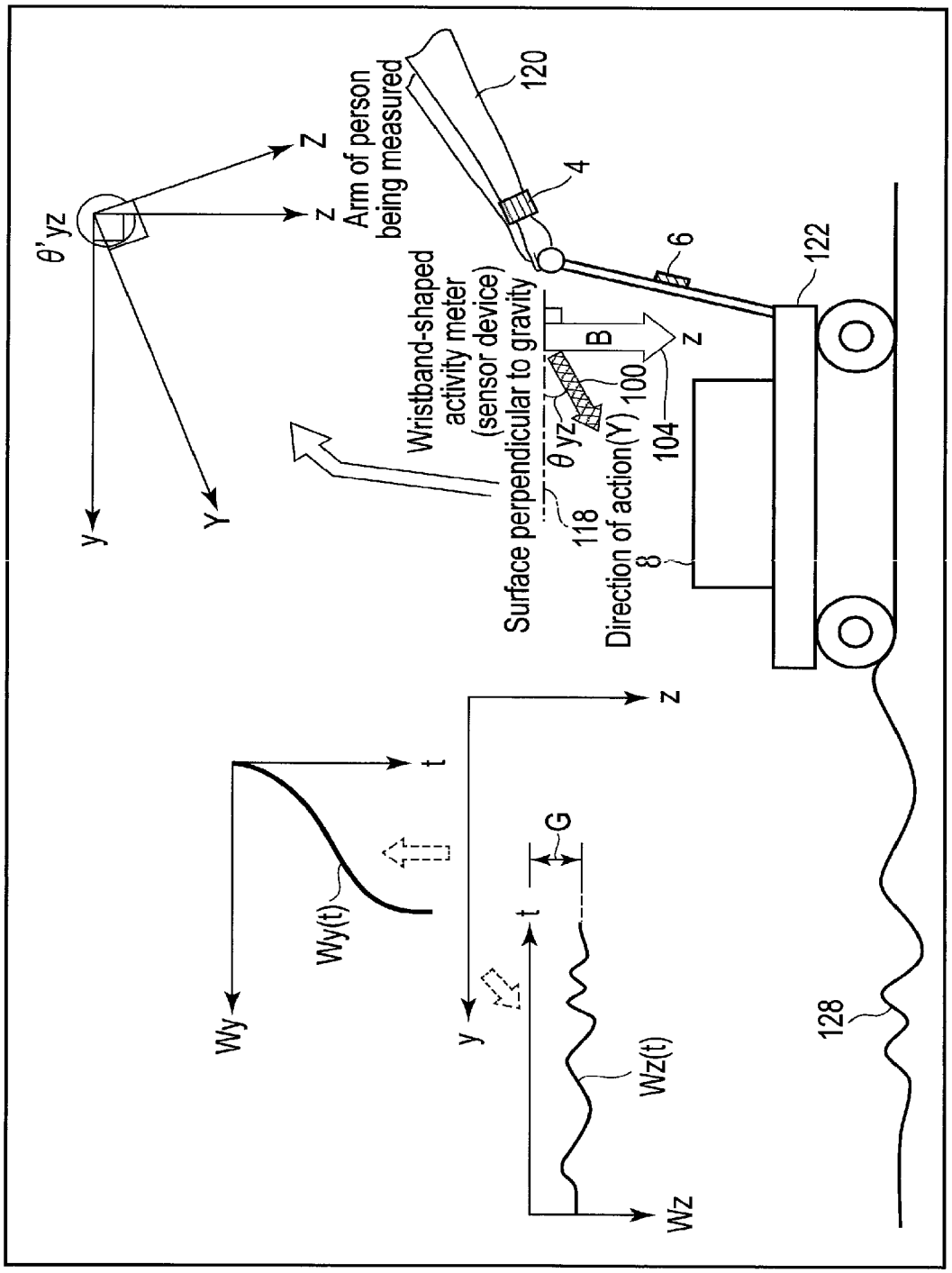
FIG. 23 is an illustration of how to form an angle different from that in FIG. 15.
Figure 24:
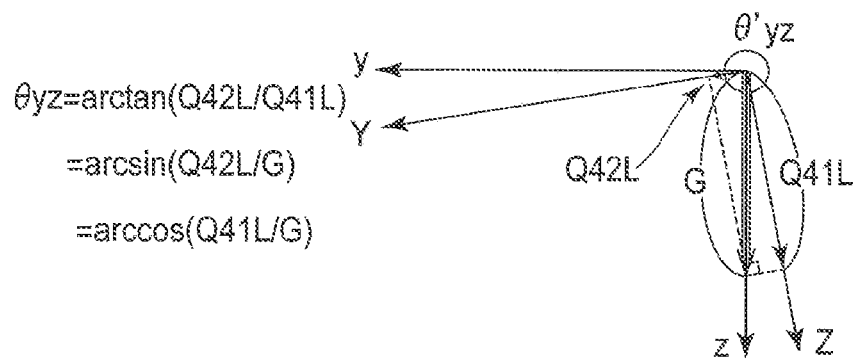
FIG. 24 is an illustration of how to form an angle different from that in FIG. 2.

In order to form the angle $\theta yz$ in FIGS. 2 and 15, the coordinate axes (Y and Z axes) preset in the interior of the wristband-shaped activity meter (sensor device) 4 are defined as a reference line. As the rotation angle from the reference line (Y and Z axes), the angle $\theta yz$ is set in the counterclockwise direction. However, the angle $\theta yz$ is not limited to the direction. Angle $\theta yz'$ can be set in the clockwise direction as shown in FIGS. 23 and 24. Similarly, the angle $\theta yz$ can be set in the counterclockwise direction with the z and y axes along the gravity direction and the floor direction as a reference line.

An application example other than the embodiment focused on the dolly movement 20 described so far, will be described below. An example a state estimation method in which the person being measured 2 carries the article 8 directly by hands without using the dolly 122, is shown in (a) of FIG. 25.

Figure 25:
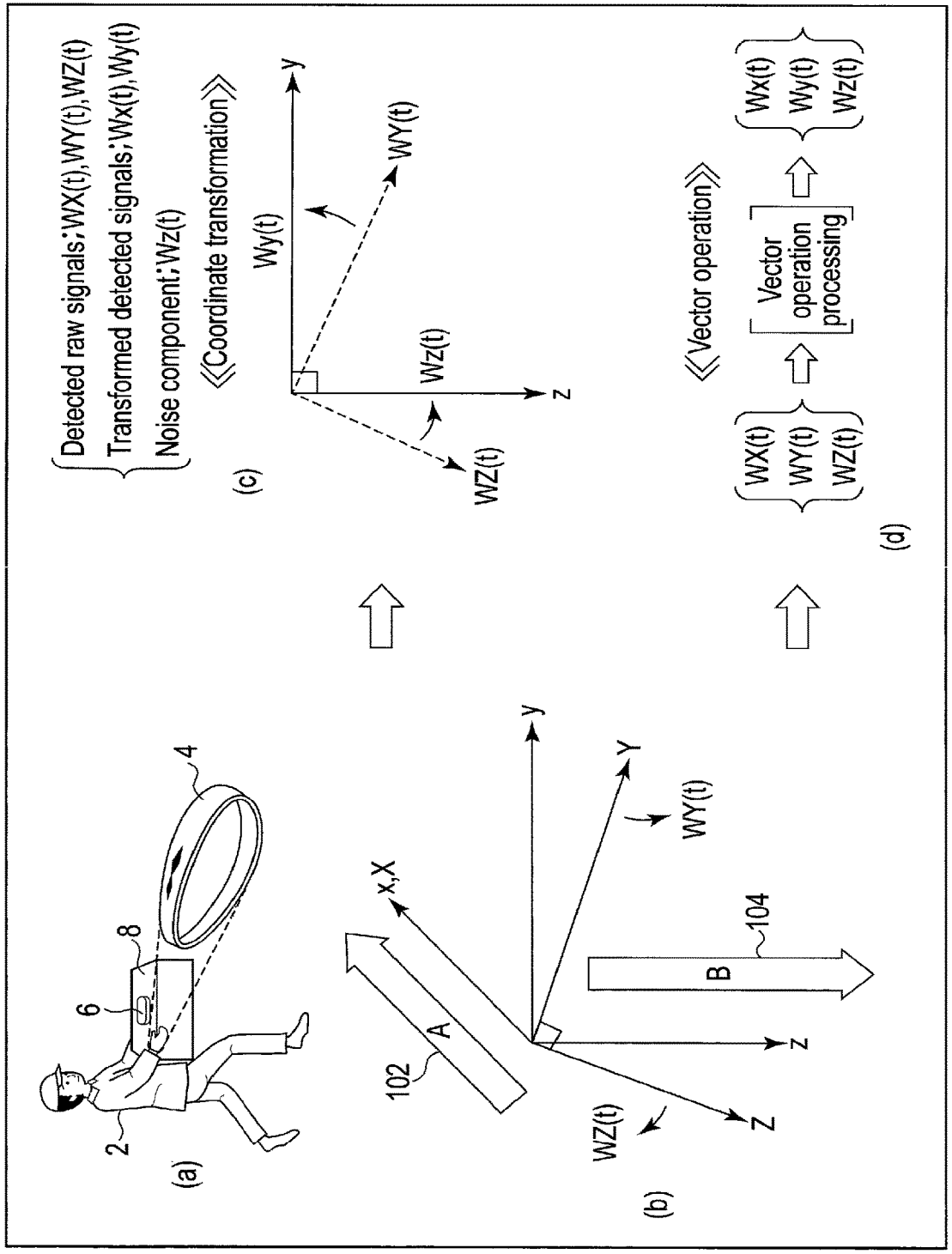
FIG. 25 is an illustration of a signal processing method in which a worker carries a thing with hands.

In FIG. 25, too, a coordinate axis direction similar to those in FIGS. 14 to 16 is defined. In other words, in the wristband-shaped activity meter (sensor device) 4 attached to the person being measured 2, the direction from the arm 120 of the person being measured to the fingers thereof is defined as a Y axis, the direction orthogonal to the Y axis and from the left little finger to the thumb is defined as an X axis, and the axis direction perpendicular to the back of the hand is defined as a Z axis.

Furthermore, the direction of criterion B (gravity) 104 is defined as a z axis and the direction of criterion A (geomagnetism direction) 102 is defined as a y axis. The criterion B (gravity) 104 and criterion A (geomagnetism direction) 102 are extracted from the detected raw signals collected from the three-axis acceleration sensor 72 and the three-axis geomagnetism sensor 74 which are built in the wristband-shaped activity meter (sensor device) 4 through the same method as described above. For brevity of description here, the x-axis direction and the X-axis are provisionally caused to coincide with each other.

When the person being measured 2 walks empty-handed without carrying any specific article, the Y-axis direction is closer to the z-axis direction. As compared with this, when the person being measured 2 walks with a specific article 8 to be carried, the Y axis is directed to the vertical direction of the z axis. If, therefore, the relationship between the x axis of the Y axis and the y and z axes is simply checked, it can be estimated whether the person being measured 2 walks empty-handed or with a specific article 8 to be carried. In this application example, therefore, the Y-axis direction is checked first.

When the Y axis is directed to a direction different from the z-axis direction, it is possible to estimate an approximate moving state of the person being measured 2 only from the detected raw signal WY(t) in the Y-axis direction obtained from the three-axis acceleration sensor 72.

However, when the person being measured 2 moves (walks) with the article 8 as shown in (a) of FIG. 25, the article 8 slightly moves vertically. Therefore, the movement components of the vertical movement of the article 8 are mixed as disturbance noise into the detected raw signals WX(t) and WY(t) collected from the three-axis acceleration sensor 72.

The disturbance noise component Wz(t) caused by the vertical movement of the article 8 to be carried appears most significantly in the detected raw signal WX(t) collected from the three-axis acceleration sensor 72. It is thus possible to reduce the disturbance noise components mixed into WX(t) and WY(t) using the disturbance noise component Wz(t) appearing in WX(t).

In the system (signal processing system) according to the present embodiment, a plurality of detected raw signals that change over time are collected from one or more sensors, and the detected raw signals (or some of them) are processed to reduce noise and extract a specific signal component. As an example of the extraction of this specific signal component, a method for extracting a predetermined criterion from predetermined frequency components Q41L, Q42L and Q43L, which are obtained after the low-pass filtering process 138 shown in FIG. 3, using the equations (1) to (3), has been described. However, the present embodiment is not limited to this example. In the present embodiment, the specific signal component can be extracted using any other processing methods. As an example of signal processing to be performed at this time, the process using the equation (4) or (6) shown in (c) of FIG. 25 can be performed. However, the present embodiment is not limited to this signal processing. For example, another optional signal processing method such as vector operation shown in (d) of FIG. 25 can be adopted.

The detected signal generation (signal processing) 96 (FIG. 12 or 13) after reduction of disturbance noise component Wz(t) due to the vertical movement of the article 8 to be carried, brings about the advantage capable of high-accuracy behavior estimation. When the drive device 44 is driven to provide service to a user based upon the behavior estimation result 16, the service can be provided more accurately.

As a further application example, high-accuracy detection/behavior estimation/service can be provided by combining the detected raw signals obtained from the sensors. As a method for combining the detected raw signals obtained from the sensors, the detected raw signals collected from the three-axis acceleration sensor 72 shown in FIG. 12 or 13 can be combined with the position detection function 98. In other words, the relative position of the wristband-shaped activity meter (sensor device) 4 can be estimated by subjecting the detected raw signals collected from the three-axis acceleration sensor 72 to signal processing (signal operation). Feeding the result of the position detection function 98 described above back to this estimation result improves the accuracy of position detection of the wristband-shaped activity meter (sensor device) 4.

Figure 26:
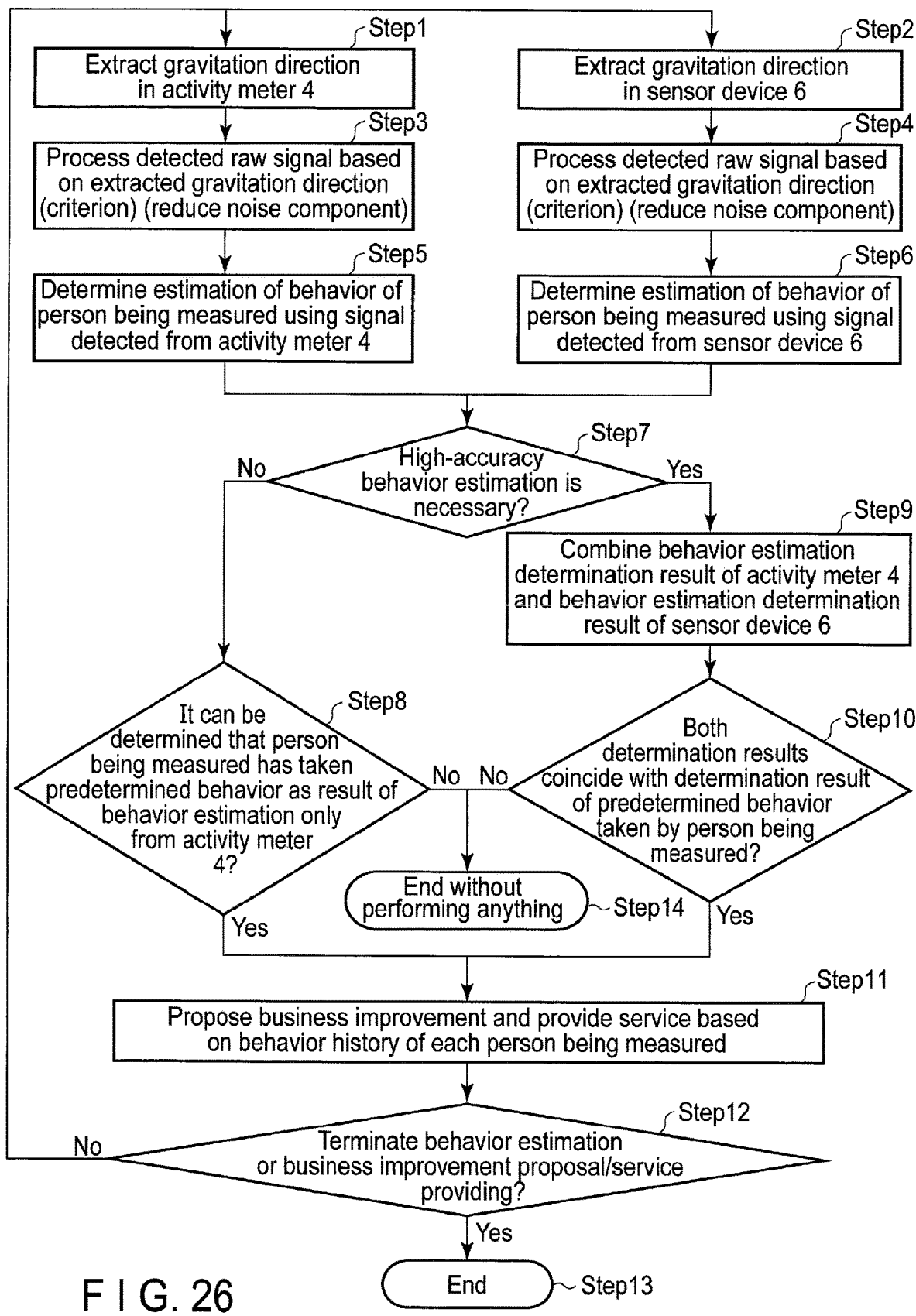
FIG. 26 is an illustration of an application example using detected signals from different sensors.

As another application example, a method for improving the detection accuracy by combining the detected raw signals collected from the wristband-shaped activity meter (sensor device) 4 shown in (a) of FIG. 1 and the detected raw signals collected from the sensor device 6 fixed to a predetermined object such as the dolly 122 is shown in FIG. 26. As has been described, the sensor device 6 also includes the three-axis acceleration sensor 72 and the three-axis geomagnetism sensor 74 and has the position detection function 98 using the communication control unit 84.

Thus, a gravity direction (criterion B) 104 is extracted in the wristband-shaped activity meter (sensor device) 4 (Step 1) and the sensor device 6 (Step 2) at the same time. The sensor device 6 may be fixed to part of the dolly 122 as shown in FIG. 16 and may be fixed directly to the article 8 itself along FIG. 25.

Then, based upon the angle θyz of each extracted gravity direction (criterion B) 104, the detected raw signals are processed in the wristband-shaped activity meter (sensor device) 4 (Step 3) and the sensor device 6 (Step 4) at the same time to reduce noise components.

After that, based upon a result of the above reduction of noise components, the behavior estimation engine 56 of the edge device 42 determines behavior estimation for the wristband-shaped activity meter (sensor device) 4 (Step 5) and the sensor device 6 (Step 6).

In Step 7, it is determined whether high-accuracy behavior estimation is necessary. If high-accuracy behavior estimation is not necessary, only the behavior estimation results based on data obtained from only the wristband-shaped activity meter (sensor device) 4 are used (Step 8) to propose business improvement and provide service based on the behavior history of the person being measured 2 (Step 11) or terminate the process (Step 14).

If high-accuracy behavior estimation is necessary to the contrary as a result of the determination in Step 7, a behavior estimation determination result from the wristband-shaped activity meter (sensor device) 4 and that from the sensor device 6 are combined (Step 9).

Based on the determination result in Step 9, the business improvement proposal and service providing (Step 11) based on the activity history of each person being measured 2 or process termination (Step 14) is selected.

Similar to Step B9 in FIG. 22B, the process from Step 1/Step 2 to Step 11 corresponding to one cycle period is repeated until the behavior estimation process or service providing process is completed. The determination as to whether to repeat the process is made in Step 12. When the behavior estimation process or business improvement proposal/service providing process is completed in Step 12, a series of processes is terminated (Step 13).

As described above, the estimated behavior results from only the detected raw signals obtained from the wristband-shaped activity meter (sensor device) 4 and the behavior estimation results obtained from only the detected raw signals obtained from the sensor device 6 are combined with each other. This combination brings about the advantage capable of high-accuracy behavior estimation and high-quality service providing.

The method for collecting the detected raw signals during the behavior of the person being measured 2 to estimate the behavior of the person being measured 2 has been described so far. However, the present embodiment is not limited to this method. In the system (behavior estimating system) according to the present embodiment, the state of a target object can be estimated from the detected raw signals collected from a predetermined object (other than human beings and animals) and its corresponding service can be provided.

Figure 27:
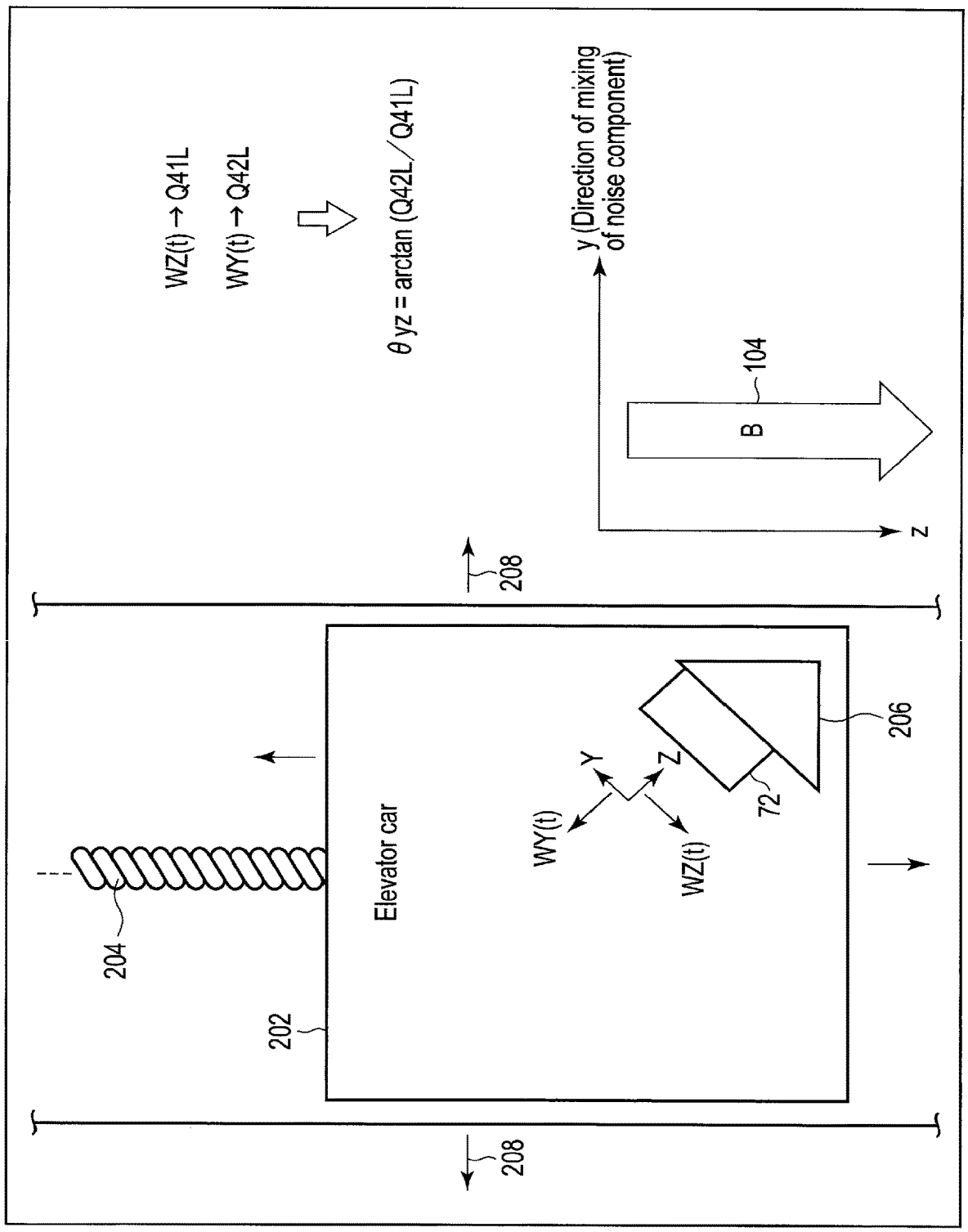
FIG. 27 is an illustration of an example of a method for processing detected raw signals from an elevator moving up and down.

An application example (FIG. 27) of estimating the state of an elevator car 202 itself (and service providing as needed) using the raw signals WY(t) and WZ(t) detected from the sensor (e.g., three-axis acceleration sensor 72) fixed to the elevator car 202, will be described.

If the three-axis acceleration sensor 72 is inclined and fixed to a fixing base 206 of the elevator car 202, the direction of the Z axis set in the three-axis acceleration sensor 72 is inclined to the z axis along the criterion B (Gravity) 104. Then, the rolling components 208 in the y-axis direction, generated when the elevator car 202 moves vertically in the z-axis direction, are mixed as noise components into the detected raw signals WZ(t) and WY(t).

In this case, too, the components Q41L and Q42L are extracted through the low-pass filtering process 138 (FIG. 3) to allow an inclination angle θyz for attaching the three-axis acceleration sensor 72 to be calculated using the equation (1).

Furthermore, using a result of the above, the signals are separated into Wy(t) corresponding to the rolling component 208 and Wz(t) (from which the mixed rolling component 208 is reduced) representing only the vertical movement of the elevator car 202.

Using the calculation result Wz(t), the estimation engine 56 of the edge device 42 determines whether the elevator car 202 moves vertically as scheduled. If an unexpected detected signal Wz(t) is obtained during the vertical movement, the elevator is regarded as malfunctioning, and service for repairing the elevator is provided.

Simultaneously with the above, the estimation engine 56 of the edge device 42 monitors the state of the rolling 208 generated during the vertical movement of the elevator car 202 from the detected signal Wy(t). If abnormal rolling is found during the vertical movement of the elevator car 202, service for repairing the elevator is provided.

Using the system (behavior estimating system 52) according to the present embodiment as described above brings about the advantage that different detected signals Wz(t) and Wy(t) can be monitored simultaneously and accurately.

Figure 28:
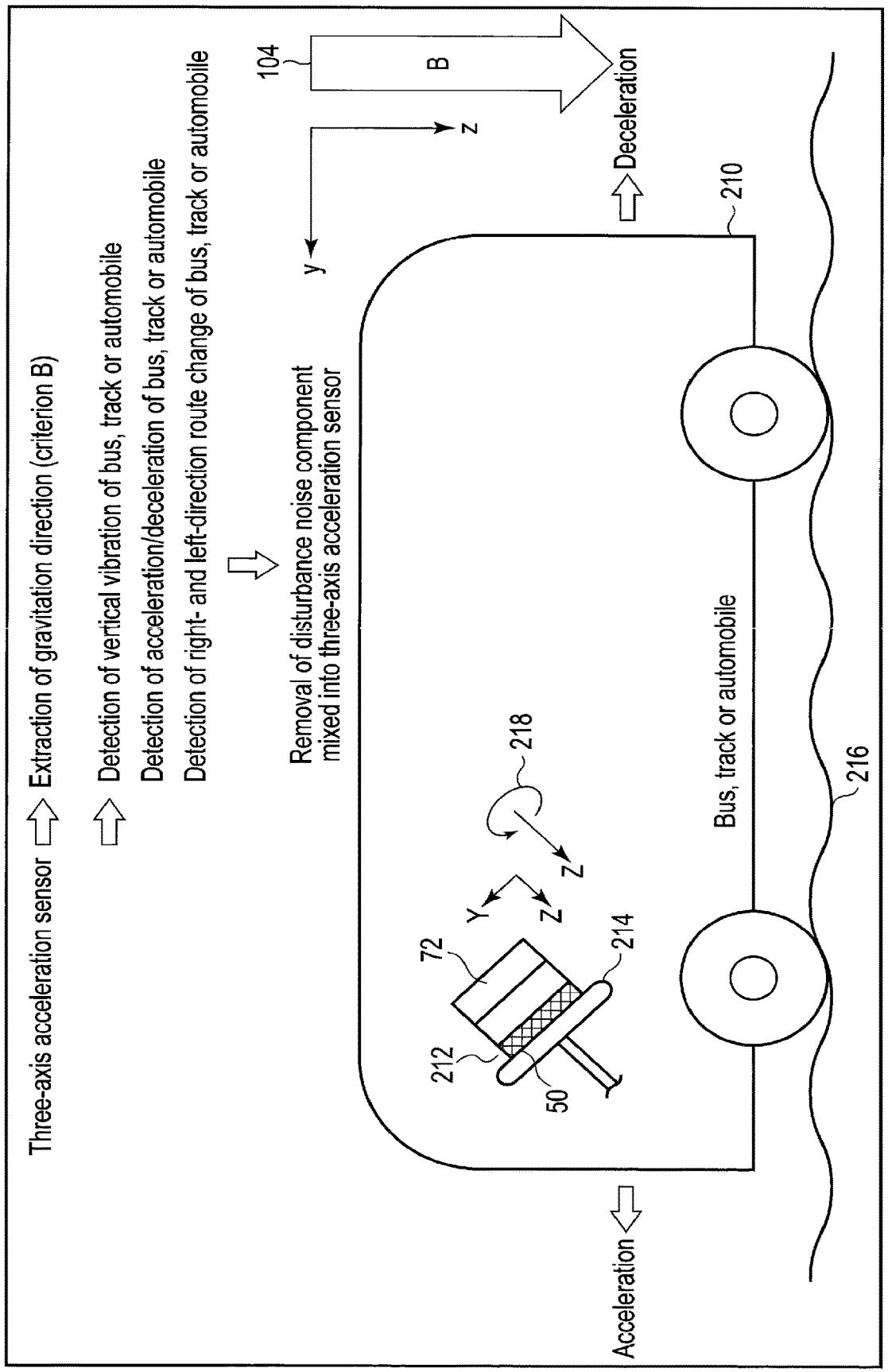
FIG. 28 is an illustration of an application example in which an acceleration sensor and an angular velocity sensor are combined.

The foregoing descriptions have been so far made with an emphasis on the acceleration sensor as a sensor. However, the sensor is not limited to the acceleration sensor. In the present embodiment, an angular velocity sensor can be used. FIG. 28 shows an application example in which the present embodiment is applied to a bus, a truck or an automobile 210. Criterion B (gravity direction) 104 is extracted from the detected raw signals WX(t), WY(t) and WZ(t) collected from the three-axis acceleration sensor 72 fixed in the bus, truck or automobile 210. Based on the criterion B, acceleration components Wx(t), Wy(t) and Wz(t) in the z-axis, y-axis and x-axis directions are extracted by rotation coordinate transformation or vector synthesis to make it possible to detect the states of vertical vibration, acceleration and deceleration, and right- and left-direction course change of the bus, truck and automobile 210. In the application example shown in FIG. 28, the acceleration/deceleration direction of the bus, truck or automobile 210 indicates the y-axis direction, and the z-axis direction coincides with the gravity direction 104 corresponding to the criterion B. Though not shown, the direction in which the bus, truck or automobile 210 turns sideways (direction of course change) is directed to the x-axis direction.

The present embodiment is not limited to the above. The three-axis angular velocity sensor 212 can be fixed to the steering wheel 214 of the bus, truck or automobile 210 by means of the fixing member 50 (e.g., adhesive) to extract a history of the wheel operation during the driving. In this case, however, the vertical vibration, acceleration and deceleration, and right- and left-direction course change of the bus, truck and automobile 210 are mixed as disturbance noise into the rotation direction 218 of the steering wheel detected by the three-axis angular velocity sensor 212.

To prevent the disturbance noise, disturbance noise components can be reduced by processing the raw signals detected from the above three-axis angular velocity sensor 212 using the raw signals detected from the three-axis acceleration sensor 72. Removing the disturbance noise components from the three-axis angular velocity sensor 212 using the raw signals detected from the three-axis acceleration sensor 72 brings about the advantage capable of detecting the operation history of the steering wheel 214 with accuracy, estimating the behavior of the driver and providing the driver or passengers with appropriate service.

In the descriptions given so far, the fixed physical quantity such as the geomagnetism direction and gravity direction is taken as an example of criteria 102 and 104. However, the criteria are not limited to the physical quantity. In the system (signal processing system) according to the present embodiment, for example, a prescribed route direction (e.g., the direction of a slope) may be set to criterion C (prescribed route) 106. This application example will be described with reference to FIG. 29B.

Figure 29A:
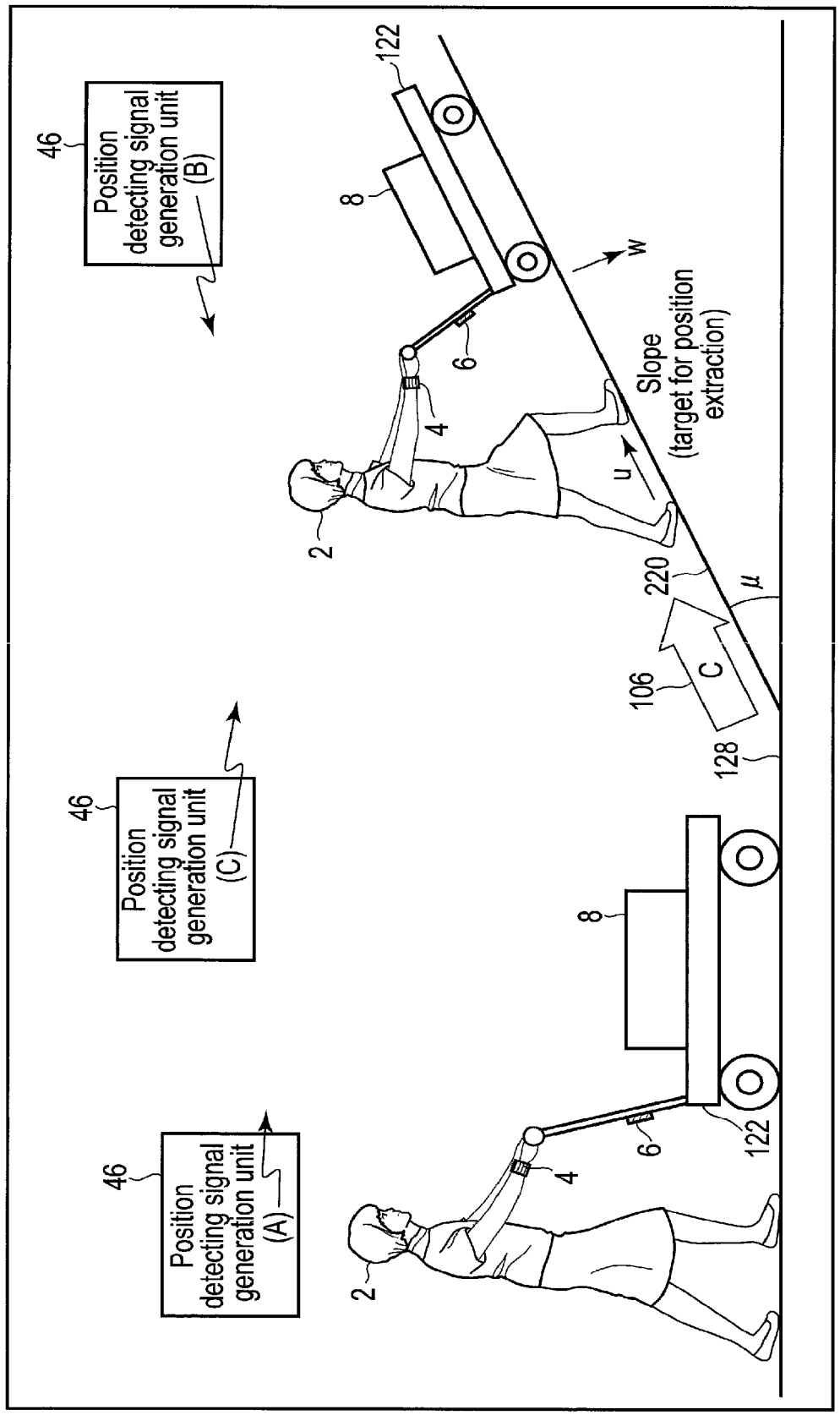
FIG. 29A is an illustration (1) of another embodiment of the criterion extraction method.

In the embodiments described so far, the floor surface 128 needs to be in a direction perpendicular to the gravity direction as a prerequisite condition on which the criterion B (gravity) 104 can be used. However, when the person being measured 2 moves along a slope 220 with a predetermined inclination of angle μ with respect to the plane perpendicular to the gravity direction 104 as shown in FIG. 29A, if the direction along this slope is set as a new criterion C (prescribed route) 106, the behavior of the person being measured 2 can be estimated with efficiency.

While the direction (the direction in which the person being measured 2 moves) along the slope with an inclination of angle μ with respect to the floor surface 128 having a plane perpendicular to the gravity direction 104 is set as a new criterion C (prescribed route) 106, the direction will be defined as a u axis and a direction orthogonal to the direction (a direction along the slope 220) will be defined as a w axis.

As a method for setting the direction along the slope 220 to the criterion C (prescribed route) 106, the movement routes of a plurality of persons being measured 2 are accumulated, and based on a result of the statistical processing, (the direction of) the criterion C (prescribed route) 106 is defined/extracted in the present embodiment.

The position detecting signal generation unit 46 (A) to (C) is provided within a range in which the person being measured 2 moves in advance as described with reference to FIGS. 12 and 13. The position detecting signal generation unit 46 (A) to (C) continues to transmit time information at the time of transmission using wireless communication. The communication control unit 84 of the wristband-shaped activity meter (sensor device) 4 receives the time information at the time of transmission, detects a time lag between the transmission and reception, and detects position information of the communication control unit 84 using trigonometry.

When the person being measured 2 climbs the slope 220, history information about a change in position of the wristband-shaped activity meter (sensor device) 4 is accumulated (in the memory unit 82 of FIGS. 12 and 13). From the accumulated history information, the criterion C (prescribed route) 106 can be extracted.

Figure 29B:
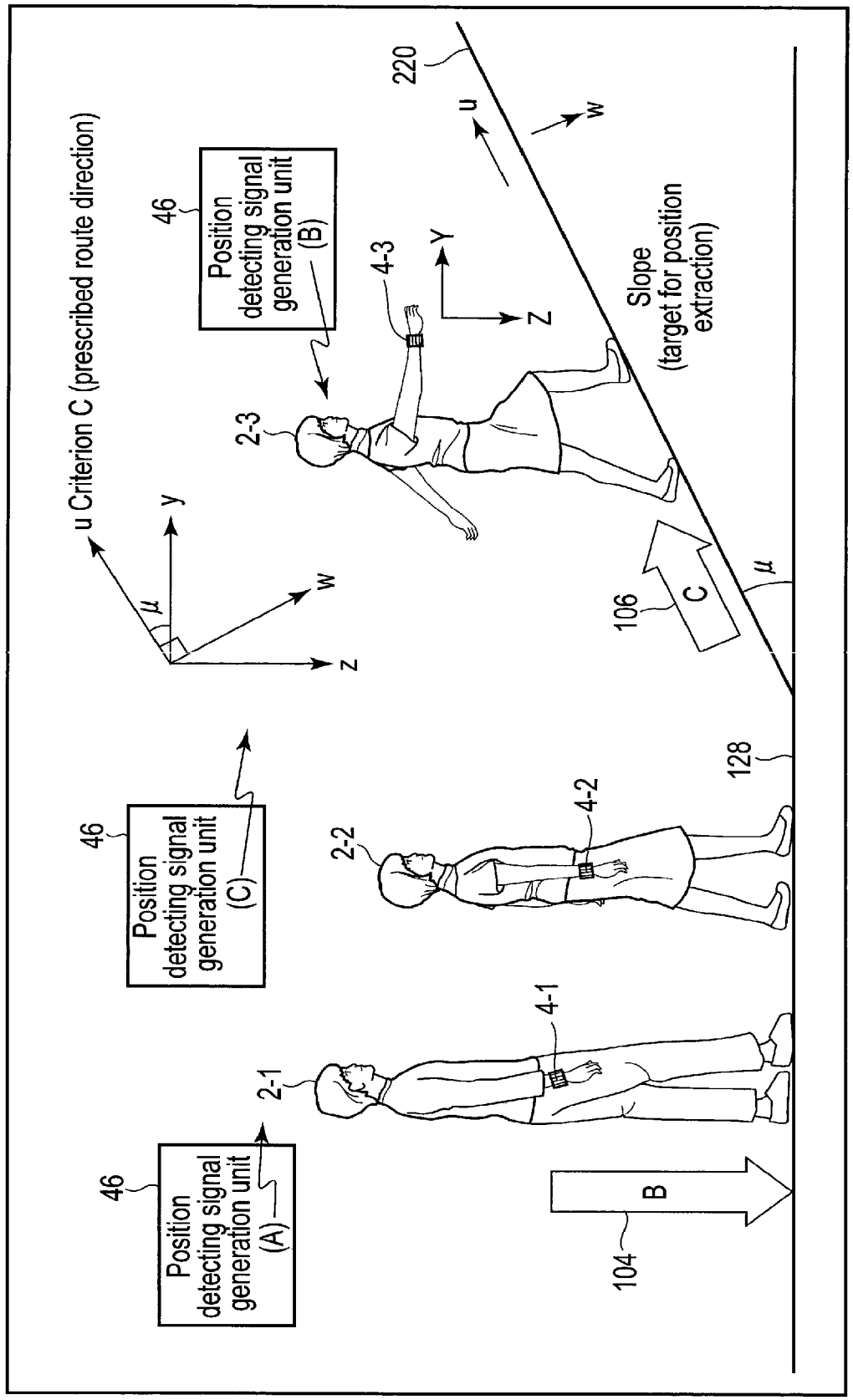
FIG. 29B is an illustration (2) of another embodiment of the criterion extraction method.

In FIG. 29A, the history information on the movement route obtained when the person being measured 2 climbs the slope 220 and pushes the dolly 122 is used. However, the present embodiment is not limited to the history information. As shown in FIG. 29B, a movement route history obtained when the persons being measured 2-1 to 2-3 each equipped with the wristband-shaped activity meter (sensor device) 4 move empty-handed on the slope 220, may also be used.

Figure 29C:
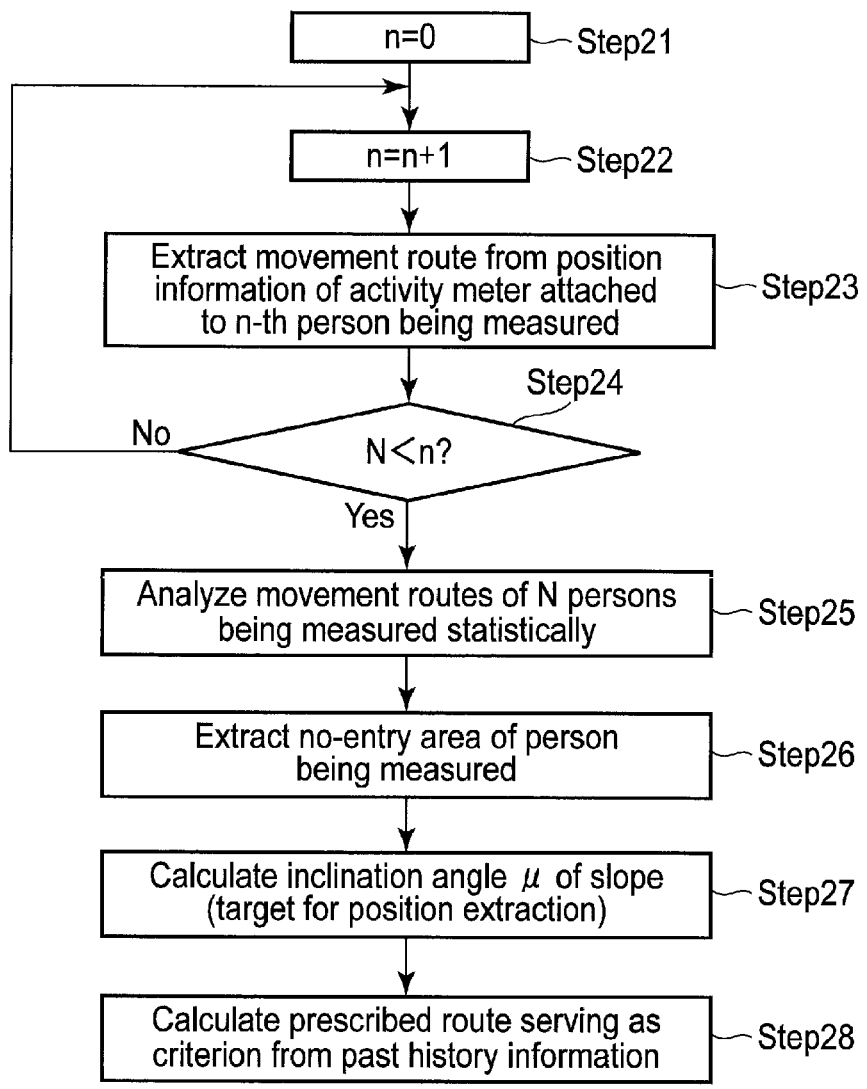
FIG. 29C is an illustration (3) of another embodiment of the criterion extraction method.

A method for extracting the direction of criterion C (prescribed route) 106 will be described with reference to FIG. 29C. In FIG. 29C, criterion C (prescribed route) 106 is extracted utilizing a history of a change in position during the movement of N persons being measured 2.

First, "n=0" is set as the initial value (Step 21), and the movement route of the n-th person being measured 2 is extracted from the history information of a change in position of the activity meter 4 attached to the n-th person being measured (Step 23). In each cycle of this process, the value of n is incremented by one in Step 22. Then, the extraction of the movement route history is repeated until the value of n exceeds the value of N (Step 24) to sequentially accumulate the movement routes of N persons being measured (history information of a change in position).

After the collection of a series of data is completed, the movement routes of N persons being measured are analyzed statistically (Step 25). Using the results, a no-entry area of the persons being measured is extracted in Step 26. As shown in FIGS. 29A and 29B, the person being measured 2 who climbs the slope 220 cannot pass under the slope (position lower than the floor surface 128). Thus, the underside of the slope 220 (in the ground of the slope) shown in FIGS. 29A and 29B corresponds to the no-entry area. Using no-entry area information of the person being measured so calculated, the inclination angle μ of the slope 220 is calculated (Step 27).

Thus, the prescribed route (criterion C (prescribed route) 106) serving as a criterion, which the person being measured 2 has passed, is calculated from the past history information (Step 28).

The present embodiment and its application examples described so far are directed to a method for utilizing detected raw signals collected from the sensors related to the acceleration, angular velocity and magnetic field. However, they are not limited to this method. The raw signals detected from any type of sensor can be used. Another application example of using photoelectric conversion signals detected from an optical sensor is shown in FIG. 30.

As a criterion example based on the photoelectric signal of the optical sensor, a sunlight direction can be set to criterion D_108. For example, in the outdoors on a clear sky day, criterion D (sunlight direction) 108 can be extracted using sunlight from the sun 230.

Figure 30:
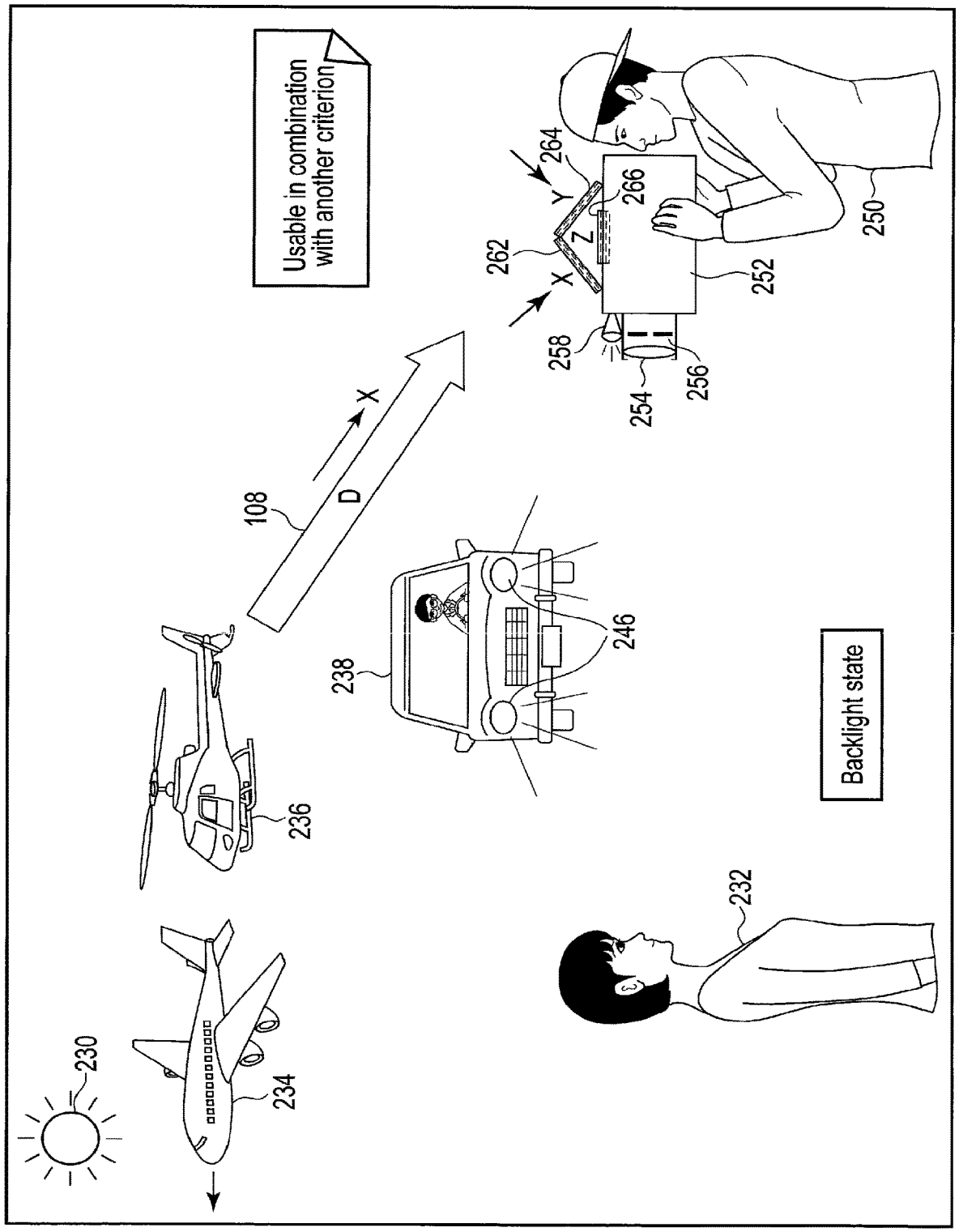
FIG. 30 is an illustration of an application example using a predetermined reference regarding a photoelectric signal.

As an example of providing service to a user using the criterion D (sunlight direction) 108, a method for detecting a backlight state automatically is shown in FIG. 30. In other words, it is automatically detected whether the photography of a subject 232 using a photography camera 252 is in a backlight state to optimize the photography state of the subject 232.

When the sunlight direction (criterion D) 108 is extracted in the outdoors on a clear sky day, an airplane (noise source) 234 and a helicopter (noise source) 236 flying in the sky are noise sources that block the sunlight from the sun 230. As a noise source on the ground, light emitting objects such as car lights (noise sources) 246 that are mounted on automobiles 238 are present everywhere on the ground. These noise sources may adversely influence the extraction of the criterion D (sunlight direction) 108.

Even though sunlight is temporarily blocked under the influence of the airplane (noise source) 234 and helicopter (noise source) 236 flying in the sky, the blocked state does not continue for a long period of time. If, therefore, low-frequency components are extracted from the detected light of sunlight emitted from the sun 230 (e.g., utilization of the low-pass filtering function 138 in FIG. 3), the adverse influence from the airplane (noise source) 234 and helicopter (noise source) 236 can be eliminated.

As shown in FIG. 30, the light-receiving surfaces of the optical sensors (solar cell panels 262, 264 and 266) placed in the photography camera 252 are non-parallel to one another. It is thus possible to calculate the sunlight direction (criterion D) 108 using a difference in the number of photoelectric signals detected by the optical sensors (solar cell panels) 262, 264 and 266. The optical sensors (solar cell panels 262, 264 and 266) can independently be placed in positions away from the photography camera 252.

Since the sun 230 is present in the sky when the photography time of the subject 232 is around noon, the criterion D (sunlight direction) 108 is substantially perpendicular (sky direction) to the ground. In contrast, the light emitted from light-emitting sources on the ground, such as car lights (noise sources) 246 that are mounted on the automobiles 238 are irradiated at an angle close to the extension direction of the ground.

Noise components can be removed by using a difference in angle between the light emitted from the light source on the ground and the sunlight direction (criterion D) 108. Specifically, the criterion D (sunlight direction) 108 is calculated with accuracy using, e.g., the low-pass filtering process 138 in FIG. 3 (extraction of components whose frequency is not higher than cutoff frequency fc), and the detected raw signals WX(t), WY(t) and WZ(t) collected from the optical sensors (solar cell panels) 262, 264 and 266, respectively are processed using the criterion D, thus calculating the intensity of the sunlight whose noise components are reduced.

As a means for providing service to a photographer 250 when backlight is detected, an aperture 256 (a type of drive device for exposure adjustment) and a light 258 (drive device) of the photography camera 252 can be controlled to take measures against the backlight.

An example of this series of processing method will be described in detail with reference to FIG. 31. The start process in Step 31 corresponds to the pre-processing start immediately before the photographer 250 takes a picture of the subject 232 with the photography camera 252.

Prior to the actual picture taking, in Step 32, the detected raw signals collected from the optical sensors (solar cell panels) 262, 264 and 266 having light-receiving surfaces perpendicular to the X-axis, Y-axis and Z-axis directions which are orthogonal to one another are subjected to a low-pass filtering process (signal components whose frequency is not higher than cutoff frequency fc are extracted to reduce the influence of light blocked by the airplane 234 and helicopter 236 which are noise sources).

Then, the sunlight direction (criterion D) 108 is extracted (Step 33) based upon a result of the above. In the extraction of the sunlight direction (criterion D) 108 (Step 33), the equation (1) obtained from FIG. 2 is used.

In Step 34, the extracted sunlight direction (criterion D) 108 is compared with the direction to which the photography camera 252 is directed to determine whether the subject 232 is in the backlight state. If the subject 232 is not in the backlight state, the camera starts to take a picture in the state as shown in Step 34.

If the subject 232 is in the backlight state, the following measures are taken in accordance with the intensity of the sunlight as an example of service to be provided to the photographer 250.

As shown in FIG. 30, there are a number of light emitting sources (noise sources) on the ground. To calculate the intensity of the sunlight, therefore, it is necessary to take measures to reduce noise from the light intensity detected in Steps 35 to 37.

The light intensity (detected raw signals WX(t), WY(t) and WZ(t)) detected from the optical sensors (solar cell panels) 262, 264 and 266 are subjected to low-pass filtering process 138 to extract predetermined frequency components Q41L, Q42L and Q43L. Based on this result, the angle θyz of the criterion D (sunlight direction) 108 can be calculated and the irradiated light intensity can be calculated by arithmetic processing using the equation (4) or (6) (Step 35).

Since the position of the sun 230 can be predicted from the picture-taking time information, the angle between the ground and the criterion D (sunlight direction) 108 can also be predicted. From the prediction result, the direction of the light emitting source (noise source) on the ground can be estimated, and noise components mixed from the light emitting source (noise source) can be calculated (Step 36) as in the arithmetic processing using the equation (4) or (6).

Since the criterion D (sunlight direction) 108 is not always perpendicular to the ground, the noise components from the light emitting source (noise source) on the ground are mixed into the irradiated light of the sunlight direction (criterion D) components calculated in Step 35. Signal processing (arithmetic processing between signals) is performed using the noise components calculated in Step 36 to allow noise to be reduced further (Step 37).

The backlight correction method that is a method for providing service to the photographer 250 in the example of FIG. 30 includes two methods of adjustment of the aperture 256 and emission of the light 258 to select the service providing method appropriately according to the intensity of sunlight (amount of sunlight). The selection of the service providing method according to the amount of sunlight is performed in Step 38.

More specifically, when the amount of sunlight is small (the backlight state is not so strong), the size of the aperture 256 (drive device) with an exposure amount adjustment function is changed (Step 39). Thus, the light-receiving amount of the photography camera 252 is automatically controlled to correct the exposure light. As another method for correcting an exposure amount in this case, the gain of a signal detected from an imaging device (not shown) which is built in the photography camera 252 can automatically be changed.

On the other hand, since the backlight state is strong when the amount of sunlight is very large, the exposure light is not corrected sufficiently within the adjustment range of the aperture 256 (exposure amount adjustment using the drive device). In this case, picture taking is started (Step 41) while the light (drive device) 258 attached to the photography camera 252 is lit to irradiate the subject 232 and take measures against the backlight as shown in Step 40. When the picture taking is completed, an end process (Step 42) is performed.

A method for reducing noise from the detected signals and providing service using only the photoelectric signals obtained from the optical sensors (solar cell panels) 262, 264 and 266 has been described with reference to FIGS. 30 and 31. However, the present embodiment is not limited to this method, but the photoelectric signals can be combined with other types of signals detected from other sensors or combined with another criterion. This brings about the advantages capable of improving the accuracy of the detected signals and the accuracy of the service to be provided.

A specific example of the above will be described below. The sunlight direction (criterion D) 108 varies depending upon picture-taking time and picture-taking locations. As has already been described with reference to FIG. 12 or 13, the three-axis geomagnetism sensor 74 in the behavior estimating system 52 can detect the direction of the earth's axis. Also, the picture-taking time can be confirmed accurately using time information transmitted from the position detecting signal generation unit 46. It is thus possible to calculate the sunlight direction (criterion D) 108 from the earth's axis direction and the picture-taking time information. With this information, the sunlight direction (criterion D) 108 calculated from the optical sensors (solar cell panels) 262, 264 and 266 can be corrected to calculate the sunlight direction (criterion D) 108 with high accuracy and obtain an amount of sunlight with higher accuracy. As a result, a more accurate service can be provided to the photographer 250.

As an application example of the present embodiment, a method (noise reduction method) for improving the accuracy of an audio signal detected by combining directional microphones 282, 284 and 286 will be described with reference to FIG. 32. Consider the case where only the audio signal output from a specific speaker 270 set in a fixed position is detected with high accuracy using the directional microphone 282.

There are a large number of disturbance audio noise sources 272 and 274 around the specific speaker 270 set in the fixed position, and the disturbance noise components generated therefrom are mixed into the directional microphone 282. In this case, a fixed speaker direction 110 is set to criterion E (Y-axis direction), and the directional microphone 282 to direct a signal is directed to the Y-axis direction. Then, the disturbance audio noise components mixed from the directions other than the criterion E (direction of the fixed speaker) are detected by the directional microphones 284 and 286 that are directed to the X-axis direction and the Z-axis direction, respectively.

Then, the signal processing using the detected raw signals collected from the directional microphones 284 and 286 is performed to reduce the noise components mixed into the directional microphone 282.

If the value of cutoff frequency fc in the low-pass filtering process 138 shown in FIG. 3 is set to 50 Hz, 60 Hz or 0.5 Hz to filter the audio signals (detected raw signals), the following disadvantages will occur.

Figure 33:
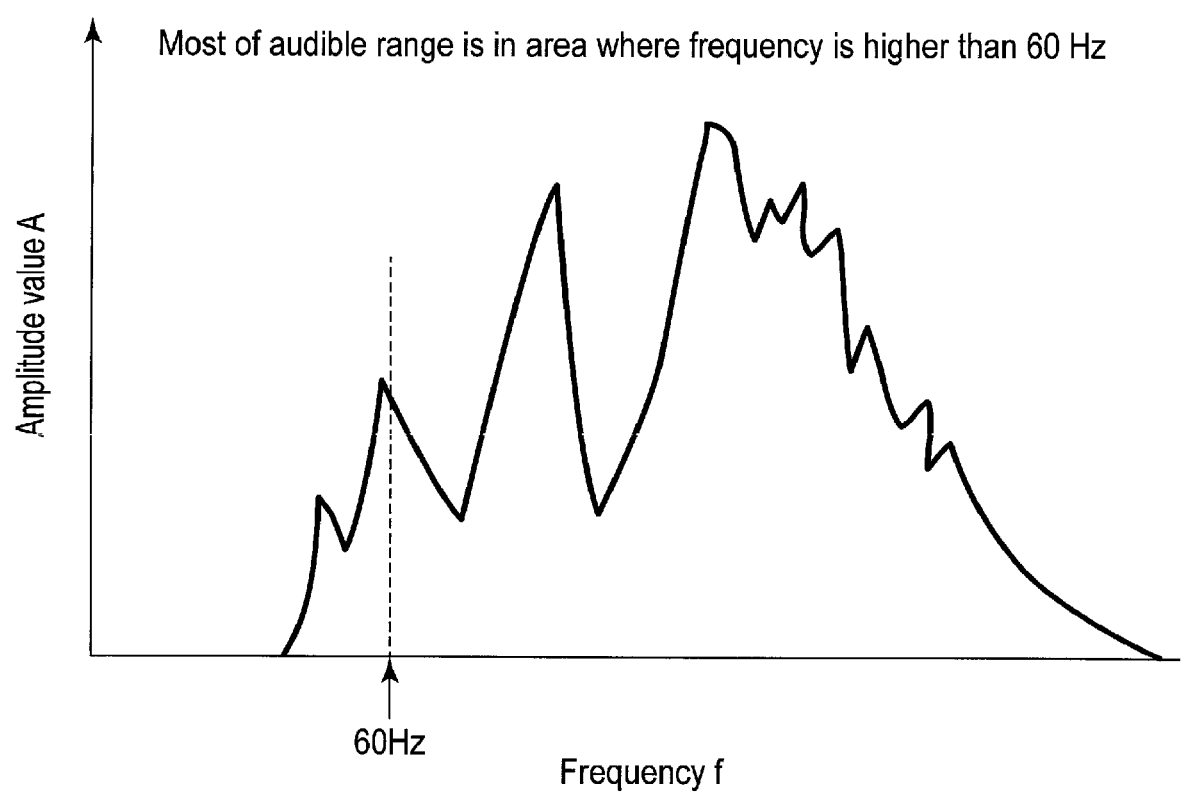
FIG. 33 is an illustration of frequency spectral characteristics of a general audio signal.

The audible range of human beings in the frequency characteristics of audio signals contains a number of frequency components the frequency of which is higher than 60 Hz, as shown in FIG. 33. If, therefore, the audio signals (detected raw signals collected from the directional microphone 282) are directly subjected to the low-pass filtering process 138 (FIG. 3) to extract only the low-frequency components of 60 Hz or lower, there is a risk that important audio signal components will be erased.

Figure 34:
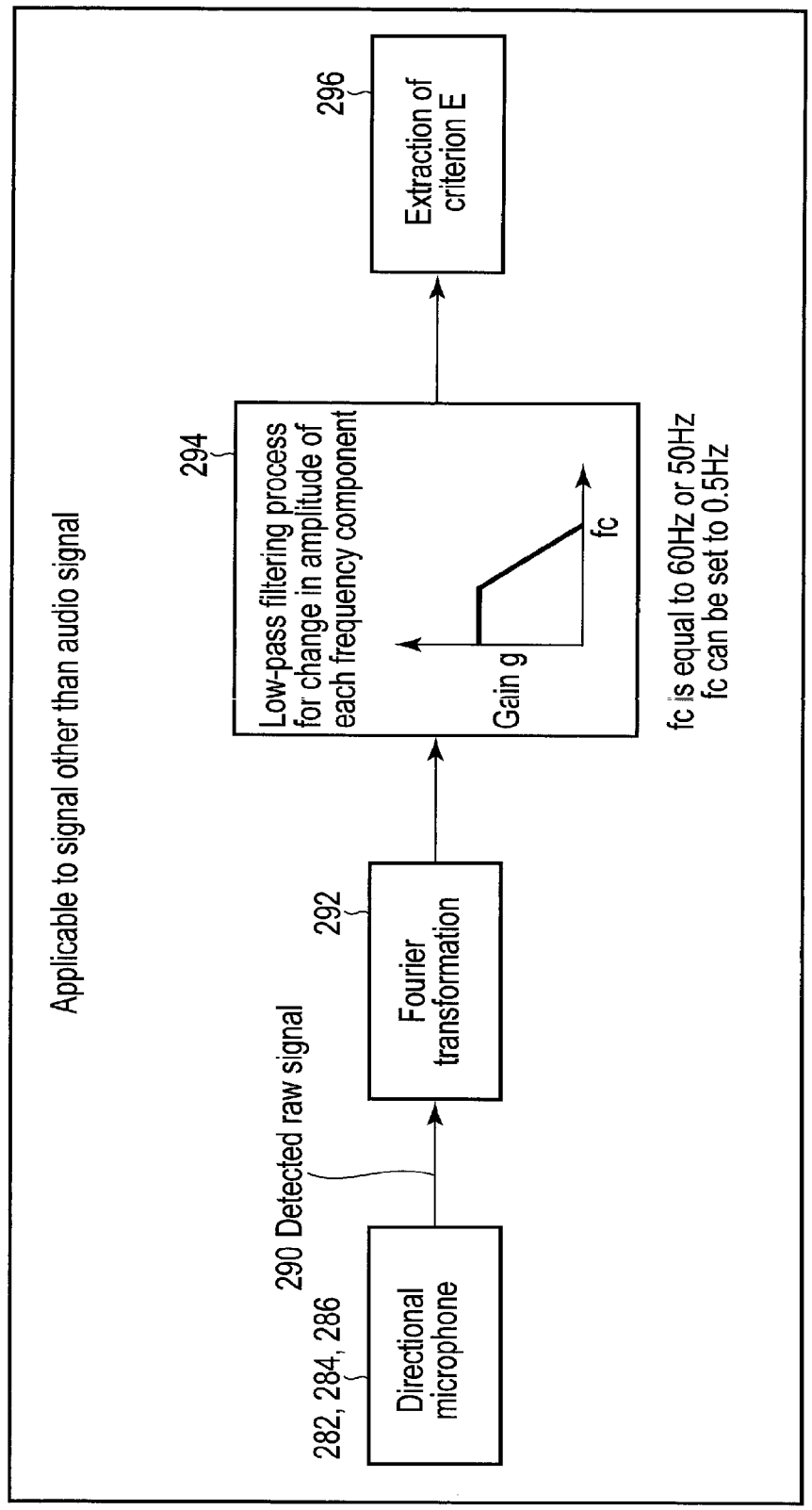
FIG. 34 is an illustration of an example of a method for extracting a criterion from audio signals.

As a means for solving the above problem, an audio signal (detected raw signal 290) can be Fourier transformed 292 and a low-pass filtering process 294 can be performed for the amplitude of each of the Fourier transformed frequency components, as shown in FIG. 34. As described in FIG. 12 or 13, the detected raw signals collected from the directional microphone 282 (signals converted into digital signals by the A/D converter 78) are stored temporarily in the memory unit 82 and processed. Thus, the low-pass filtering process can easily be performed for the amplitude of each of the Fourier transformed frequency components (Fourier coefficients).

However, the present embodiment is not limited to the above. The memory unit 82 can properly be utilized in the order described as follows: "The detected raw signals are Fourier transformed every predetermined period", "the Fourier coefficients are stored in sequence in the memory unit 82", "the result of the low-pass filtering process for each of the Fourier coefficients is stored again in the memory unit 82" and "the signals are processed using information stored in the memory Unit 82".

Therefore, as an example of the processing method of the Fourier transformation 292 described with reference to FIG. 34, the audio signals (detected raw signals 290) stored appropriately in the memory unit 82 can be read in sequence to store a new additional audio signal (detected raw signal 290) in the memory unit 82 and process the audio signals (detected raw signals 290) stored in the memory unit 82 in parallel at the same time.

A method for inserting the Fourier transformation 292 has been described with reference to FIG. 34, taking an audio signal as an example. However, the present embodiment is not limited to the audio signal, but the Fourier transformation 292 can be performed for all of the detected raw signals 290 and the low-pass filtering process can be performed with respect to a change in amplitude of the frequency component.

Figure 35:
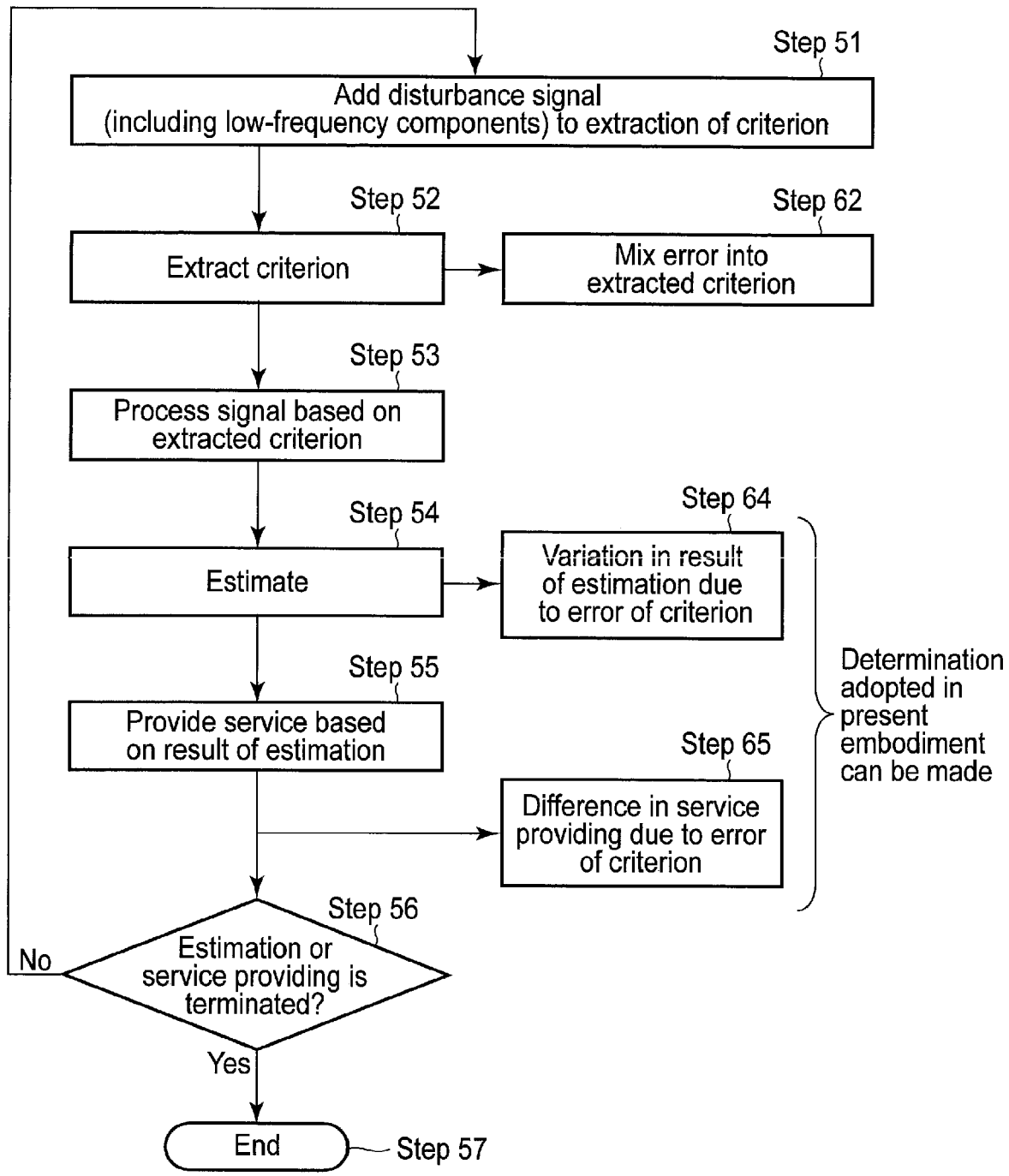
FIG. 35 is an illustration of a tendency to the contents of processing in the present embodiment.

The tendency toward the processes performed according to the present embodiment and using its application examples described so far, will be described with reference to FIGS. 35 to 37. In the present embodiment and its application examples, predetermined information is extracted using the raw signals detected from different sensors. As one type of the extracted predetermined information, a predetermined criterion can be used. Consider a case where a disturbance signal (including the low-frequency components) is added to the extraction of a criterion in Step 51 prior to the extraction of the predetermined criterion. If the predetermined criterion is extracted in this state (Step 52), an error is easily mixed into the extracted criterion (Step 62).

If, furthermore, service is provided using the result of the estimation process in Step 54 (Step 55), a difference in the contents of service providing, which is caused by the mixture of an error into the criterion, is likely to occur (Step 65).

In the present embodiment and its application examples, the above cycle is repeated until the estimation process or service providing process is completed, as shown in Step 56.

Determining the states of a variation in results of estimation (Step 64) and a difference in contents of service providing (Step 65) caused by the error of criterion generated when the above cycle is repeated with a disturbance signal containing low-frequency components added (Step 51), it is possible to determine whether the technologies of the present embodiment and its application examples have been adopted.

An example of a method for adding a disturbance signal containing low-frequency components to the raw signals detected from different sensors (Step 51) will be described below.

As a method for adding a disturbance signal containing low-frequency components to the raw signals (acceleration waveforms) detected from the three-axis acceleration sensor 72, for example, an apparent gravitational acceleration can be given.

Figure 36A:
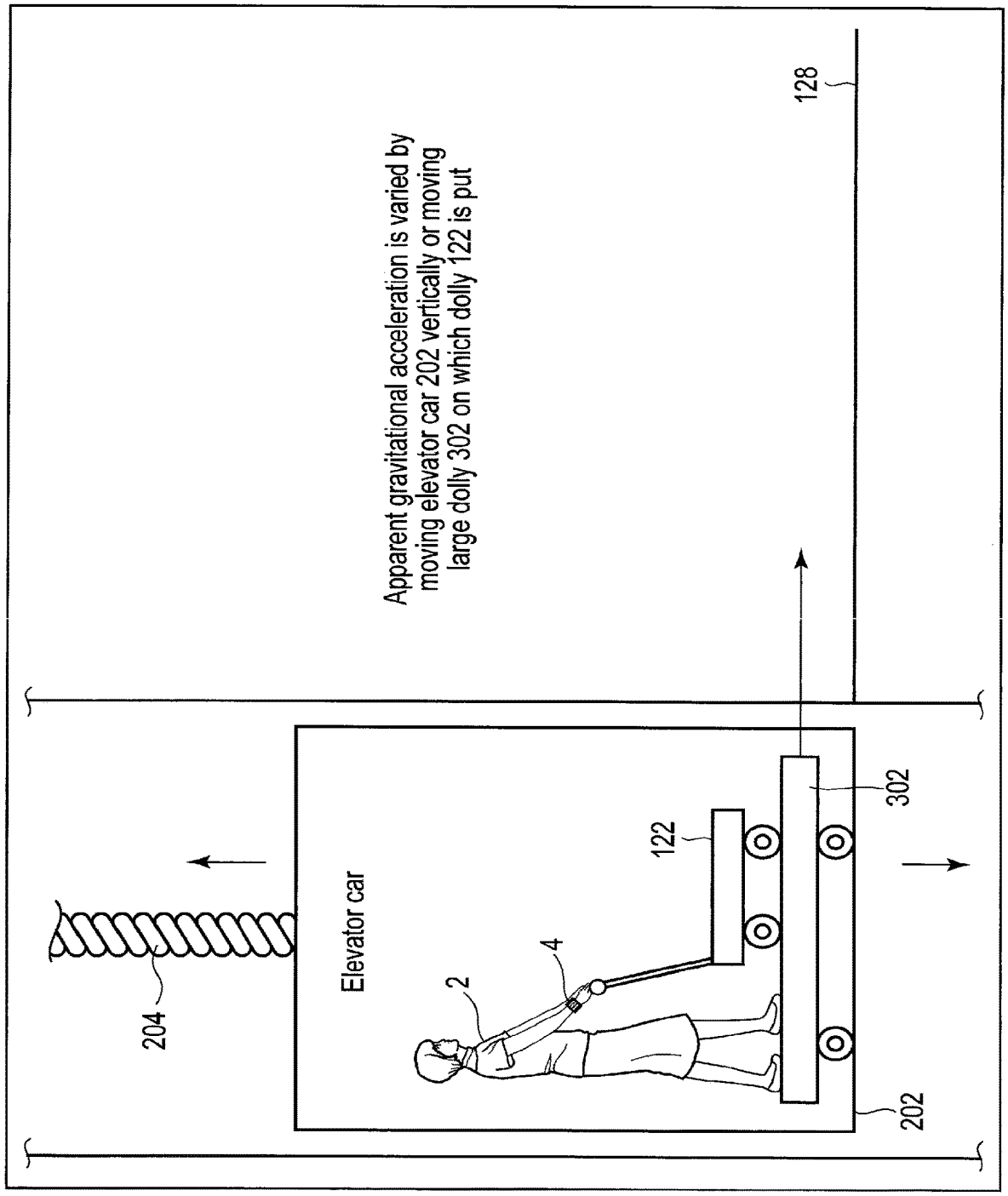
FIG. 36A is an illustration (1) of a method for mixing a disturbance signal into the extracted criterion.
Figure 36C:
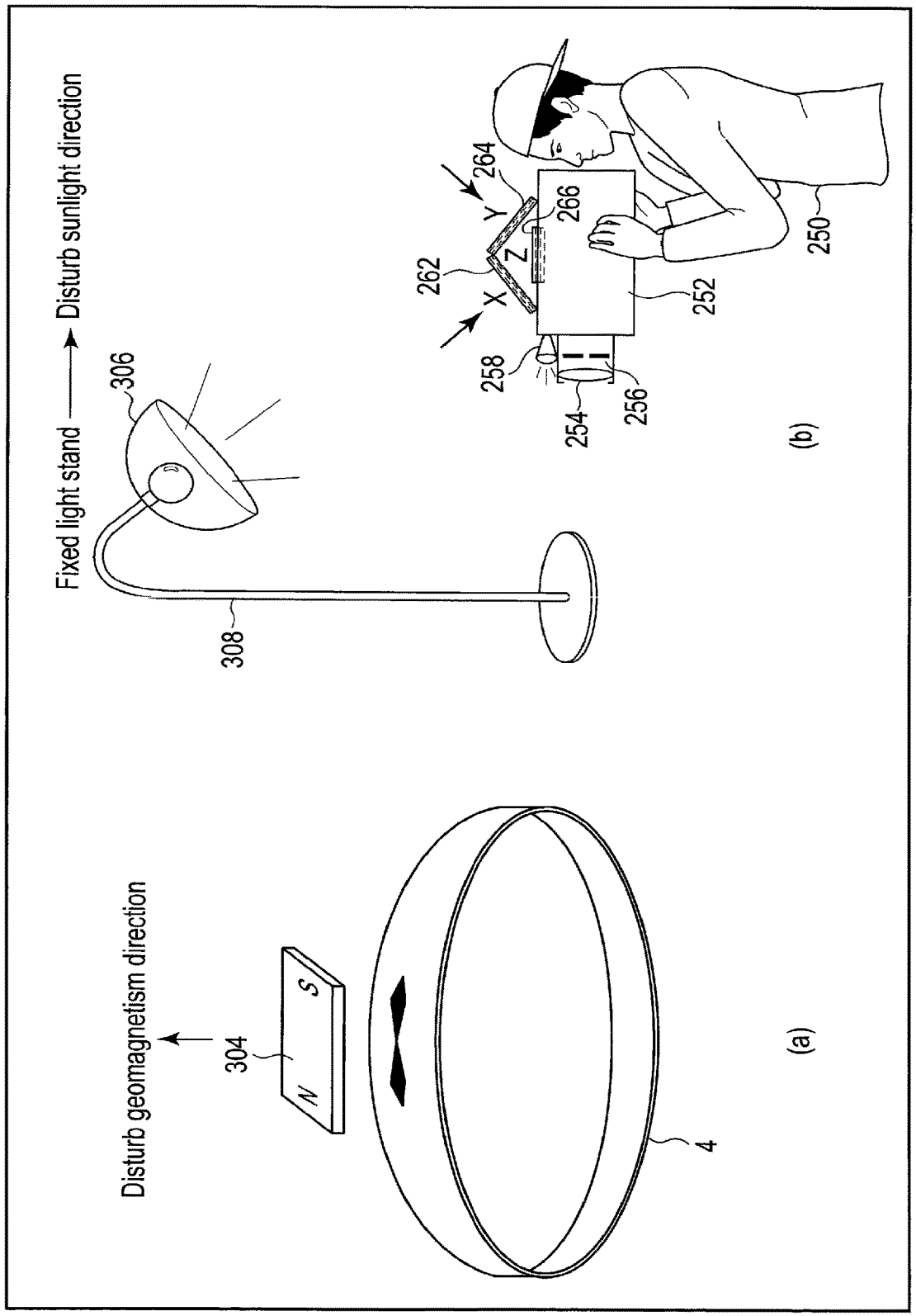
FIG. 36C is an illustration (3) of the method for mixing a disturbance signal into the extracted criterion.
Figure 37:
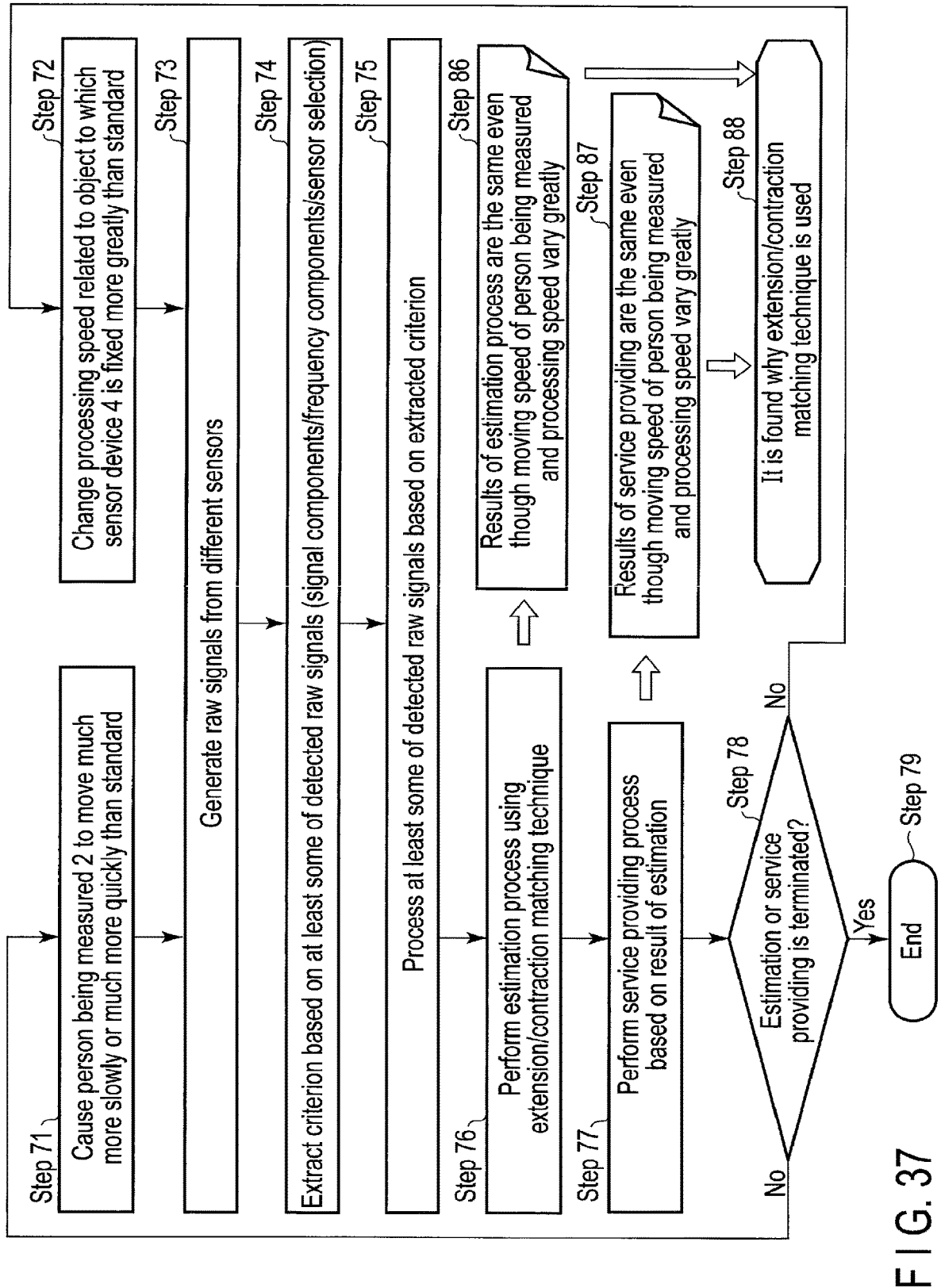
FIG. 37 is an illustration of a tendency to an extension/contraction matching process in the present embodiment.

For example, if the detected raw signals (acceleration waveforms) are collected from the three-axis acceleration sensor 72 with the elevator car 202 moving vertically using a rope 204 as shown in FIG. 36A, the value of the apparent gravitational acceleration G varies. If the angle θyz is calculated using the foregoing equation (2) or (3) as a result, an error occurs in the value of the calculated angle θyz.

Furthermore, when the door of the elevator car 202 is opened to move a large dolly 302 on which the dolly 122 is put, the apparent gravitational acceleration component is superimposed in a direction parallel to the floor surface 128. In this case, even though the equation (1) in which the value of the gravitational acceleration G is not used is used, an error is mixed into the value of the angle θyz calculated from the raw signals (acceleration waveforms) detected from the three-axis acceleration sensor 72 of the wristband-shaped activity meter (sensor device 4) attached to the person being measured 2.

The present embodiment is not limited to the above. As shown in (a) of FIG. 36B, a disturbance signal containing low-frequency components can be added using a slope (Step 51 in FIG. 35). For example, even though the behavior of the person being measured 2 is estimated using the wristband-shaped activity meter (sensor device 4) when the person being measured 2 applies force to the dolly 122, which is stopped in advance by a fixed stopper 312, to start to move it, a variation in contents of the behavior estimation (Step 64 in FIG. 35) and a difference in contents of service providing (Step 65 in FIG. 35) will be caused.

Similarly, as shown in (b) of FIG. 36B, a similar symptom appears even when the person being measured 2 starts to move the dolly 122 after he or she releases a vertical moving stopper 314 to stop the dolly 122 on a slope. It can be seen from a variation in results of the estimation (Step 64 in FIG. 35) and a difference in service to be provided (Step 65 in FIG. 35) that the technologies of the present embodiment and its application examples are adopted.

On the other hand, as a method for adding a disturbance signal containing low-frequency components to the three-axis geomagnetism sensor 74 (Step 51 in FIG. 35), a permanent magnet 304 can be stuck on the surface of the wristband-shaped activity meter 4 to add a disturbance in the geomagnetism direction, as shown in (a) of FIG. 37C.

Furthermore, as a method for adding a disturbance signal containing low-frequency components to the photoelectric signals obtained from the optical sensors (solar cell panels) 262, 264 and 266 (Step 51 in FIG. 35), a light 306 serving as a light emitting source can be placed in a fixed light stand 308 to disturb the sunlight direction.

A method using the expansion/contraction matching technique for the behavior estimation and state estimation in the present embodiment or its application examples has been described. As an example of the expansion/contraction matching technique, the DP matching (dynamic programming matching) has been described with reference to FIGS. 18 to 20. The method shown in FIG. 37 makes it possible to discover whether or not the expansion/contraction matching technique was used at the time of the estimation process (behavior estimation or state estimation).

The expansion/contraction matching technique has the feature that a similarity among patterns can be calculated while considering partial expansion/contraction in the patterns. From different sensors used in the system (signal processing system) according to the present embodiment or its application examples, the value of the detected raw signals may often vary over time. Especially in this case, when the movement speed of the person being measured 2 and the state change speed (e.g., moving speed) of a predetermined object such as the dolly 122 are changed, partial expansion/contraction (expansion/contraction in the time axis direction) is generated in the variation in the value of the detected raw signals regarding a lapse of time.

If, therefore, the estimation process (behavior estimation or state estimation) is performed using the foregoing expansion/contraction matching technique when partial extension/contraction occurs (in the time axis direction) in the detected raw signals collected from the different sensors in accordance with the moving speed of the person being measured 2 and the state change speed of a predetermined object in the system (signal processing system) according to the present embodiment or its application examples, the advantage of improving the accuracy of the estimation is brought about. In other words, even though the movement of the person being measured 2 and the state change speed of the predetermined object vary temporarily, the temporal change in processing speed is absorbed at a stage of the estimation process (behavior estimation or state estimation).

For example, as a method for varying the behavior speed of the person being measured 2, the person being measured 2 is caused to move much more slowly or much more quickly than standard as shown in Step 71.

As a method for changing the processing speed of a specific object, the speed (processing speed) at which an object (e.g., the dolly 122) to which the sensor device 6 is fixed can be changed more greatly than standard as shown in Step 72. As a specific method, the dolly 122 can be moved quickly (high-speed processing) or slowly (low-speed processing).

Then, the raw signals detected from the different sensors are collected (Step 73) and at least some of the detected raw signals (predetermined signal components and predetermined frequency components or sensor selection) are processed (Step 75).

Prior to the signal processing, predetermined information can be extracted from at least some of the detected raw signals (predetermined signal components and predetermined frequency components or sensor selection) and the signal processing can be performed based upon a result of the detected information (Step 75). The predetermined criteria 102 to 110 can be caused to correspond to the predetermined information (Step 74).

After that, if the extension/contraction matching technique is employed when the estimation process (behavior estimation or state estimation) is performed (Step 76), there is a tendency that the results of the estimation process are the same even though the moving speed of the person being measured and the processing speed vary greatly (Step 86).

Furthermore, when the service providing process is performed based upon a result of the process performed in Step 76 (Step 77), there is a tendency that the results of the service providing are the same even though the moving speed of the person being measured and the processing speed vary greatly (Step 87).

If, therefore, a tendency that the result of the estimation process or that of the service providing does not vary when the speed is changed can be found (Step 86 and Step 87), it can be understood why the extension/contraction matching technique is used for the estimation process (Step 88).

Moreover, the foregoing cycle is repeated until the estimation process or the service providing is terminated as shown in Step 78. If the cycle is so repeated, the number of samples to check the result of the estimation process and that of the service providing for each cycle is increased. If the extension/contraction matching technique is used, the probability that the determination can be made is increased.

In the system (signal processing system) according to the present embodiment shown in FIGS. 12 and 13, the drive device 44 is set to allow service to be provided to a user based upon a result of each of the different estimation processes. As one example of the drive device 44, FIG. 38 shows the glasses-type wearable terminal 1100. Part of the glasses-type wearable terminal 1100 may have a function of the sensor device. In other words, the glasses-type wearable terminal 1100 may include a camera and a microphone or have a vibration detection function to detect a predetermined instruction (control information) input from a person equipped with the terminal (person being measured 2). As the instruction input from the person, for example, he or she can block a lens unit of the camera, clap his or her hands for the microphone, request the next display by voice, provide the vibration detection function with a predetermined vibration, etc. If the glasses-type wearable terminal 1100 that originally has a function of the drive device 44 has a function of the sensor device, the advantage that the person equipped with the terminal (worker or person being measured 2) can input data without using his or her hands is brought about. Furthermore, the person equipped with the terminal (worker or person being measured 2) may estimate his or her behavior or state with the behavior estimation engine 56 (FIG. 12 or 13) based upon the input data.

The glasses-type wearable terminal 1100 includes a projection unit (display information generation unit) 1102, a screen (optical path synthesis unit) 1106, a drive unit (which may also be referred to as an image display circuit, a light source drive circuit and a signal processing unit) 1134, a wireless communication unit 1136 and the like and is operated by power applied from a power supply unit 1132 that is, for example, a button cell.

The wireless communication unit 1136 built in the glasses-type wearable terminal 1100 performs information communication between the edge device 42 and the server 40 connected to an external network. The information communicated from the edge device 42 is displayed to the person equipped with the terminal (worker or person being measured 2) through the projection unit 1102.

The projection unit 1102 includes a light source unit 1104, an image display unit 1110, a half mirror surface 1112, a total reflection surface 1114, a light emission surface 1116, a lens group 1120 and the like. The information communicated from the edge device 42 is displayed on the image display unit 1110 of the projection unit 1102 as video information or image information. Then, non-parallel light (light with divergence properties: referred to as diverging light) 1108 which is emitted from the light source unit 1104 of the projection unit 1102 is applied to the image display unit 1110 via the half mirror surface 1112, and the light reflected by the unit 1110 is projected onto the screen 1106 via the lens group 1120.

The screen 1106 includes a front-side transparent refractive body 1124, a Fresnel lens type half mirror surface 1122 and a back-side transparent refractive body 1126. Part of the diverging light 1108 is reflected by the Fresnel lens type half mirror surface 1122 and arrives at the eyes of the person equipped with the terminal (worker or person being measured 2) through the front-side transparent refractive body 1124 to form a virtual image corresponding to the image displayed on the image display unit 1110.

As the light source unit 1104, a dimmer type white LED light source can be used. The dimmer type white LED light source includes a plurality of light emitting diodes (LED) which adjust the output light amounts independently and whose emission colors are different from one another. This brings about the advantage capable of displaying the optimum emission color corresponding to the usage environment to the person equipped with the terminal (worker or person being measured 2). For example, when the glasses-type wearable terminal 1100 is used in a clean room of lighting environment the color of which is mainly orange, an image can be displayed in combination of colors excluding the orange color. If, furthermore, an image is displayed in the color that can be easily recognized by the person equipped with the terminal (worker or person being measured 2), the advantage that he or she can avoid eye fatigue and its related migraine is brought about.

For example, a reflective liquid crystal display (LCD) module is used for the image display unit 1110, and an image displayed thereon is controlled by the drive unit 1134. The drive unit also controls an emission state of the light source unit 1104.

FIG. 39A shows a procedure in which a worker equipped with the glasses-type wearable terminal 1100 performs an operation in response to an operation instruction from the edge device 42. As a specific example of the operation, the worker may inspect a manufacturing apparatus, repair a malfunctioning machine, and the like.

For example, when a worker equipped with the glasses-type wearable terminal 1100 arrives at a workplace, he or she pushes an work start button and make a special gesture. A detection signal from a predetermined sensor device inserted into the work start button is transmitted to the edge device 42. Alternatively, an imaging device that monitors the behavior of the worker may determine the gesture automatically and transmit a result of the determination to the edge device 42.

The contents of the work are divided in advance into a plurality of work units (a plurality of divided works). When the completion of a work of one unit is detected (Step SA5), the next work instruction (Step SA6) is displayed on the glasses-type wearable terminal 1100.

Figure 39B:
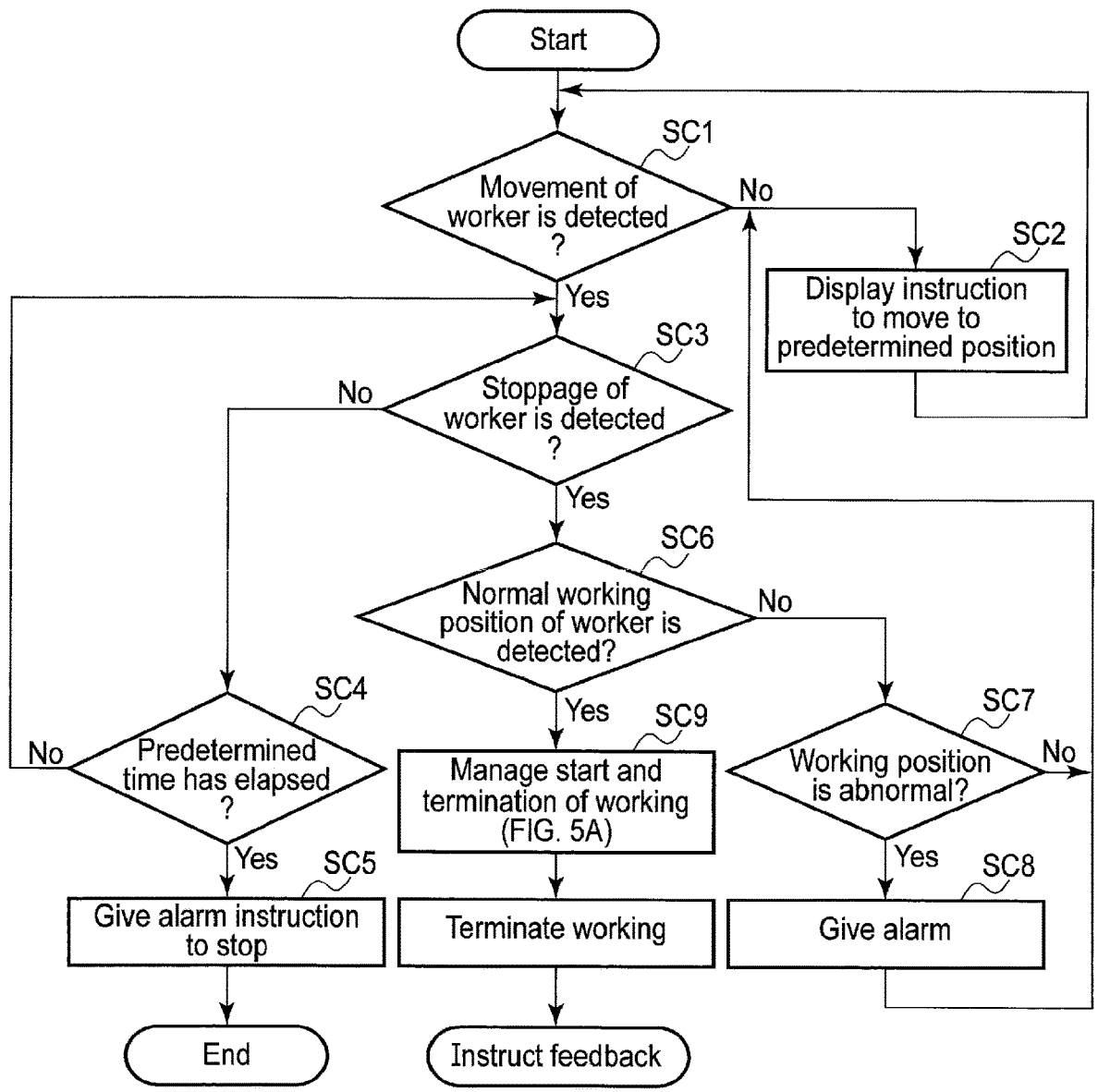
FIG. 39B is a flowchart of another operation example of the application example of the system according to the present embodiment.

FIG. 39B shows an example of another operation to be performed by a system using the glasses-type wearable terminal 1100 according to the present embodiment. FIG. 39B shows a control operation to be performed after the worker has moved to the workplace.

The glasses-type wearable terminal 1100 has the position detection function 98 shown in FIG. 12 or 13. The edge device 42 detects a position of the worker equipped with the glasses-type wearable terminal 1100 using the position detection function 98 (Step SC1). When the edge device 42 supplies a movement instruction to the worker through the glasses-type wearable terminal 1100 (Step SC2), the worker starts to move.

When the stoppage of the worker is detected (Step SC3), it is determined whether the worker stops in a normal position (an instructed target position) (Step SC6). If the worker does not stop after a while, it is determined whether time elapses a given period of time or longer (Step SC4). If the worker does not stop when time elapses a given period of time or longer, it is determined that any trouble has occurred, and the alarm is given through the glasses-type wearable terminal 1100 to instruct the worker to stop (Step SC5).

When the worker does not stop in the normal position in Step SC6, it is determined that the work position is an abnormal position (Step SC7), and the alarm is given through the glasses-type wearable terminal 1100 (Step SC8) to instruct the worker to move to a predetermined position.

On the other hand, when the worker stops in the normal position, the work instruction described with reference to FIG. 39A is started.

Figure 40:
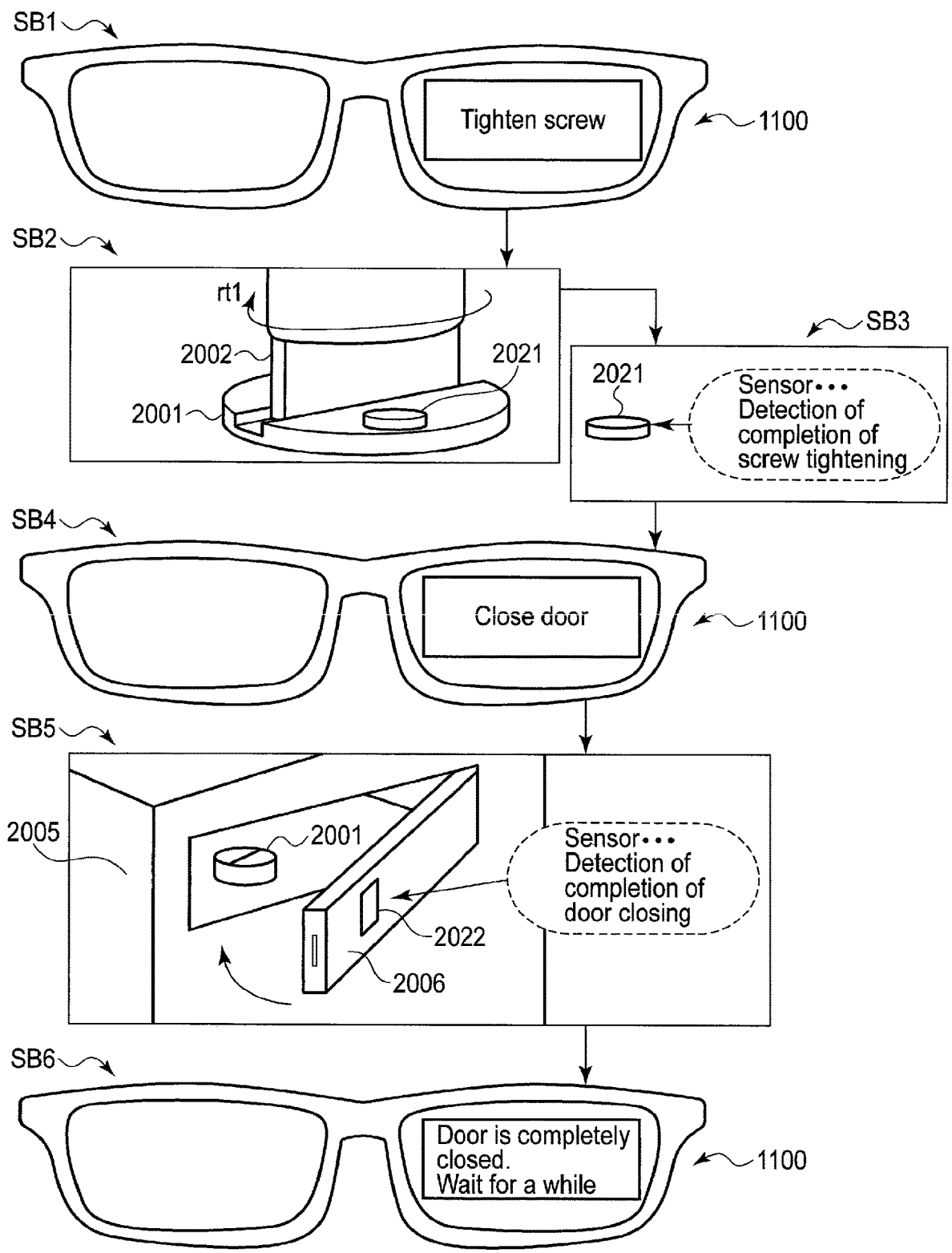
FIG. 40 is an illustration of an application example of the present embodiment.

FIG. 40 shows an example of a work process to be performed by a worker according to the foregoing work instruction. Consider here that the worker equipped with the glasses-type wearable terminal 1100 arrives at a workplace and pushes a work start button in the workplace (or makes a special gesture). When the work start button is pushed, communications are carried out between the glasses-type wearable terminal 1100 and the edge device 42. Assume here that the work of the worker in the workplace is to tighten a screw 2001 in a housing 2005 of a manufacturing apparatus. As the housing before the start of the work, the top 2006 of the housing 2005 is opened and the opening can be seen.

In accordance with the contents of the instruction transmitted from the edge device 42, a message such as "TIGHTEN THE SCREW" is displayed on the glasses-type wearable terminal 1100 (Step SB1). In accordance with the contents of the instruction, the worker inserts a driver 2002 in the housing from the opening thereof and starts to tighten a screw 2001.

A sensor (e.g., angular velocity sensor) 2021 attached to the screw 2001 or the driver 2002 allows the angular velocity to be detected (Step SB2). Thus, when the screw tightening work is started, the angular velocity sensor 2021 detects the rotation of the screw.

When the rotation detection signal is transmitted to the edge device 42, the start of the work is recognized. When the start of the work is recognized, the edge device 42 outputs an instruction to erase the current message "TIGHTEN THE SCREW".

When the tightening of the screw 2001 is completed, the detection output of the angular velocity sensor 2021 becomes zero. Upon receipt of the sensor detection signal, the edge device 42 determines the "completion of tightening of the screw" (Step SB3).

Immediately after that, the edge device 42 transmits the next instruction. Consider here that, for example, a message "CLOSE THE DOOR" is displayed (Step SB4). When the worker closes the door 2006 in response to the instruction (Step SB5), the angular velocity sensor 2022 attached to the door 2006 detects a corresponding signal.

In other words, when the door 2006 turns in a direction in which the door is closed, the angular velocity sensor 2022 detects the start of the turn. When the detection signal is transmitted, the edge device 42 detects the "start of turn of door 2006".

When the door 2006 is closed and its turn is stopped, the angular velocity sensor 2022 detects the stoppage of the door 2006 (detects that the door is closed). If a sensor detection signal is transmitted at this time, the edge device 42 determines that "the door is completely closed" (Step SB5). Then, the next instruction is transmitted to the glasses-type wearable terminal 1100. The edge device 42 transmits a message such as "DOOR IS COMPLETELY CLOSED. PLEASE WAIT FOR A WHILE" (Step SB6).

The rotation axis direction serving as a criterion to detect the rotation by the angular velocity sensors 2021 and 2022 does not always coincide with the gravitation direction. For example, when the angular velocity sensors 2021 and 2022 are placed in an oblique direction with respect to the gravitation direction, the vertical-direction vibration of the floor due to the movement of the worker is transmitted to the angular velocity sensors 2021 and 2022, and it is very likely that disturbance noise will be mixed into a rotation angle detection signal.

In order to reduce disturbance noise from the rotation angle detection signal, the three-axis acceleration sensor 72 is also built in at once in the system (signal processing system) according to the present embodiment. Accordingly, the direction θyz of the criterion B (gravitation direction) 104, which influences the angular velocity sensors 2021 and 2022, is extracted. If the signal processing (rotation transformation) between the angular velocities is performed using the angle θyz, an angular velocity detection signal from which disturbance noise components based upon an external vibration are reduced can be generated. This signal processing brings about the advantage that the edge device 42 can correctly grasp the work (behavior) of the worker and the conditions of the door 2006 and the screw 2001.

FIG. 41 shows a detailed configuration of the sensor device. The sensors 2021 and 2022, which detect whether the worker has completed a predetermined work on a production site or the like, has a configuration capable of additionally being set in the existing device (corresponding to the screw 2001 or door 2006 shown in FIG. 40) such as the existing environment or production facilities.

As a method for automatically detecting that a worker has completed his or her work, there is a method for purchasing a new production device that incorporates in advance a plurality of sensors 2021 and 2022 for detecting whether a predetermine work has been completed in order to replace the existing device. This method however involves huge business investment costs for the purchase. Adopting a method for additionally setting the sensors 2021 and 2022, each of which is very inexpensive, in the existing environment or production facilities brings about the advantage capable of automatically detecting whether a worker has completed his or her work very inexpensively.

As a method for setting the sensors 2021 and 2022 automatically, a bonding section 3008 is formed in a section where the sensors 2021 and 2022 and the existing environment or production facilities are in contact with each other in the embodiment shown in FIG. 41. Specifically, the bonding section 3008 for the contact portion of the existing environment and the existing device can be formed of, e.g., an adhesive sheet whose strength is high. In this case, when the sensors 2021 and 2022 are shipped, a cover sheet is attached in advance to the contact portion of the existing environment and the existing device of the bonding section 3008. The cover sheet is removed in the place where the sensors 2021 and 2022 are placed, and the bonding section 3008 is bonded directly to the existing environment and the existing device. The present embodiment is not limited to this. The bonding section 3008 for the contact portion of the existing environment and the existing device is not caused to have any adhesive properties (or bonding properties) in advance, but an adhesive can be caused to penetrate a portion in which the bonding section 3008 is in direct contact with the existing environment or the existing device and can be fixed thereto when the sensors 2021 and 2022 are placed. As another method for placing the sensors 2021 and 2022 additionally, they can be fixed to the existing environment or the existing device by a screw using the bonding section 3008 for the contact portion of the existing environment and the existing device.

In the configuration shown in FIG. 41, an acceleration sensor unit or an angular velocity sensor unit 3006 is disposed adjacent to the bonding section 3008 for the contact portion of the existing environment and the existing device. The closer to the existing environment of a target to be set additionally and the surface of the existing device the place where the acceleration sensor unit or the angular velocity sensor unit 3006 is disposed, the more accurately the acceleration and angular velocity of the existing environment and the existing device themselves can be detected.

As shown in FIG. 41, therefore, the acceleration sensor unit or the angular velocity sensor unit 3006 is disposed in a position closer to a device (or an environmental object) to be set additionally than a control unit 3002, a short-range wireless communication unit 3004 or an environmental vibration generation device 3000. This brings about the advantage that the acceleration and angular velocity of a subject (corresponding to the screw 2001 or door 2006 in FIG. 40) can be detected.

As an acceleration sensor in the present embodiment, a low-G acceleration sensor whose measurement range is not higher than 20 G (1 G represents the gravitational acceleration of the earth) is used. When the low-G acceleration sensor is used as an acceleration sensor, the exterior wall section of the acceleration sensor unit or the angular velocity sensor unit 3006 configures a fixed section and a sensor device movable section is placed therein (in the interior of the acceleration sensor unit or the angular velocity sensor unit 3006) (the detailed configuration of the interior is omitted from FIG. 41). The acceleration is detected using variations in the position of the sensor device movable section with the fixed section. In the present embodiment, a capacitance detection system (which detects a variation in capacitance between the fixed section and the sensor device movable section) or a piezoresistive system (which detects a distortion caused in a spring portion connecting the fixed section and the sensor device movable section using a piezoresistive element disposed in the spring portion) can be used.

In the present embodiment, furthermore, a vibration system using a micro-electromechanical system (MEMS) can be utilized as an angular velocity sensor (gyro sensor). Like the foregoing acceleration sensor, the angular velocity sensor (gyro sensor) is basically configured by a fixed section that is configured by the exterior wall of the acceleration sensor unit or the angular velocity sensor unit 3006 and a sensor device movable section placed therein (in the interior of the acceleration sensor unit or the angular velocity sensor unit 3006). In the fixed section, first comb-teeth electrodes and second comb-teeth electrodes are arranged orthogonally. A voltage is applied to the first comb-teeth electrodes alternately to vibrate the sensor device movable section at fixed periods. When the acceleration sensor unit or the angular velocity sensor unit 3006 rotates, Coriolis force is generated and the sensor device movable section rotates relative to the fixed section. Then, the angular velocity is detected by considering the rotational displacement as a variation in capacitance using the second comb-teeth electrodes. The present embodiment is not limited to the foregoing mechanical system, but a magnetism system, an optical system or a mechanical system can be used in the angular velocity sensor (gyro sensor).

The data based upon the acceleration and angular velocity detected by the foregoing method is transmitted to the edge device 42 via the short-range wireless communication unit 3004. The control of the operation of the short-range wireless communication unit 3004 and the processing of signals obtained from the acceleration sensor unit or the angular velocity sensor unit 3006 are performed by the control unit 3002. As shown in FIG. 41, the short-range wireless communication unit 3004 and the control unit 3002 are arranged in the same row, which brings about the advantage capable of decreasing the height of the sensors 2021 and 2022 themselves.

As shown in FIG. 41, in the present embodiment, the environmental vibration generation device (a piezoelectric system or an electrostatic system) 3000 supplies power (power source) necessary for operating the acceleration sensor unit or the angular velocity sensor unit 3006, and the short-range wireless communication unit 3004 and the control unit 3002. The use of wires as a power source (power supply) to the sensors 2021 and 2022 involves complication associated with a change in wiring made each time the positions of the sensors 2021 and 2022 are changed. If a number of sensors 2021 and 2022 are placed using a replaceable battery as a power source (power supply), the problem that the battery replacement operation is very complicated will occur. In the present embodiment, the feature that the sensors 2021 and 2022 detect acceleration and angular velocity is used and the energy of the acceleration and angular velocity to be detected is used as a power source (power supply) is used. It is thus unnecessary to supply power by wire, which brings about the advantage that a worker is relieved of not only complexity of wiring change due to a change in placement position of the sensors 2021 and 2022 but also complexity of battery exchange.

In the event of an earthquake, the upper floor of a high-rise building is generally shaken more than a one-story building. In such a structure projecting from the shaking surface, a greater shake occurs in a location away from the direct shaking surface (shaking amplitude is large). Using this phenomenon, in the present embodiment, as shown in FIG. 41, the environmental vibration generation device 3000 is disposed at a position farthest from the bonding section 3008 for the contact portion of the existing environment and the existing device. In other words, the environmental vibration generation device 3000 is disposed at a position farther from the bonding section 3008 for the contact portion of the existing environment and the existing device than the acceleration sensor unit or the angular velocity sensor unit 3006 or the short-range wireless communication unit 3004 or the control unit 3002. Accordingly, the advantage capable of maximizing power generation efficiency is brought about.

FIG. 42 shows a basic configuration of the environmental vibration generation device 3000. Part of the configuration is similar to the basic configuration of the acceleration sensor or the angular velocity sensor described above. In other words, the environmental vibration generation device 3000 includes a fixed section 3100 and a sensor device movable section 3102, and the sensor device movable section 3102 is movable with respect to the fixed section 3100 in response to the external environmental vibration.

An instantaneous voltage generation unit 3104 is so formed that it can be moved in synchronization with the movement of the sensor device movable section 3102 to generate an instantaneous voltage in accordance with the movement of the sensor device movable section 3102. To use a piezo (piezoelectric) device as the instantaneous voltage generation unit 3104 is referred to as "a piezoelectric system" and to use an electret (an insulator with semi-permanent charges) is referred to as "an electrostatic system".

The instantaneous voltage generated by the instantaneous voltage generation unit 3104 is boosted along with DC electrification and smoothing in a voltage boosting unit 3106. Then, the power output from the voltage boosting unit 3106 is stored in a storage unit 3108.

A specific operation principle of the environmental vibration generation device 3000 shown in FIG. 42 will be described with reference to FIGS. 43 to 47. In both cases where the "piezoelectric system" is adopted and the "electrostatic system" is adopted for the instantaneous voltage generation unit 3104, the operations subsequent to that of the voltage boosting unit 3106 are common to both the cases as shown in FIGS. 43 to 47. In the case of the "piezoelectric system", the output of a piezoelectric device 3130 is connected to an input terminal 3116. In the case of the "electrostatic system", the output of a metal electrode substrate 3138 is connected to the input terminal 3116.

Specifically, as shown in FIGS. 43 to 47, in the "piezoelectric system", a connecting section that connects the fixed section 3100 and the sensor device movable section 3102 corresponds to the instantaneous voltage generation unit 3104, and the piezoelectric device 3130 is disposed in the connecting section. If the sensor device movable section 3102 is greatly displaced from a neutral position with respect to the fixed section 3100, an electromotive voltage is generated between both terminals of the piezoelectric device 3130. If the sensor device movable section 3102 returns to the neutral position, an electromotive voltage to be generated between both terminals of the piezoelectric device 3130 is reduced.

As shown in FIGS. 43 to 47, an electret material 3134 is set in the fixed section 3100 in the "electrostatic system". The electret means an insulator with semi-permanent charges. As a specific material thereof, for example, CYTOP (registered trademark) can be used. In the embodiment shown in FIGS. 43 to 47, the surface of the electret material 3134 is always charged negatively. An electret electrode substrate 3132 is connected to the electret material 3134 to hold the relative potential of the electret material 3134 constantly at "0 V". An opposing electrode 3136 in a movable state is disposed close to the electret material 3134 that is charged negatively. As the opposing electrode 3136 moves to the electret material 3134, an instantaneous voltage is generated. Thus, the opposing electrode 3136 is disposed in the instantaneous voltage generation unit 3104 described with reference to FIG. 42. The metal electrode substrate 3138 is connected to the opposing electrode 3136, and the opposing electrode 3136 is supplied with charges through the metal electrode substrate 3138. Thus, the sensor device movable section 3102 described with reference to FIG. 42 includes the metal electrode substrate 3138. It can be said that the sensor device movable section 3102 or the instantaneous voltage generation unit 3104 can be configured by the combination of the metal electrode substrate 3138 and the opposing electrode 3136. Based upon the electromagnetic capacitor theory, the absolute value of the amount of negative charges on the surface of the electret material 3134 and the amount of positive charges on the opposing surface of the opposing electrode 3136 close thereto need to coincide with each other. If, therefore, the position of the opposing electrode 3136 coincides with that of the electret material 3134, the largest amount of positive charges gather on the opposing surface of the opposing electrode 3136. If the position of the opposing electrode 3136 is greatly displaced from that of the electret material 3134, the amount of positive charges gathering on the opposing surface of the opposing electrode 3136 becomes small. The positive charges gathering on the opposing surface move to another place through the metal electrode substrate 3138.

Though not shown in FIG. 42, FIGS. 43 to 47 show that a signal detection unit 3110 is disposed at the exit of the instantaneous voltage generation unit 3104. Using the output from the signal detection unit 3110, acceleration and angular velocity can be detected. Specifically, a resistor 3120 is set in the signal detection unit 3110, and instantaneous current generated from the instantaneous voltage generation unit 3104 flows through the resistor 3120. When current flows through the resistor 3120, a voltage is generated instantaneously at either end of the resistor 3120. The instantaneous voltage is buffered by a differential buffer amplifier 3112 to allow a change in instantaneous current to be monitored from outside.

FIGS. 43 to 47 show the use of a Cockcroft-Walton circuit as an example of the voltage boosting circuit 3106. The present embodiment is not limited to this circuit, but another circuit can be used if it is able to at least rectify and smoothen a current or amplify a voltage. Furthermore, there is a capacitor element 3128 as an example of the storage unit 3108. However, the present embodiment is not limited to the capacitor element, but another rechargeable storage battery can be used.

Arrow 3114 shown in FIGS. 43 to 47 indicates a direction in which the sensor device movable section moves, and arrow 3142 indicates a direction of current. As shown in FIG. 43, when the sensor device movable section 3102 moves to the left side, the amount of distortion of the piezoelectric device 3130 becomes small and thus an electromotive voltage between both terminals (both surfaces) in the piezoelectric device 3130 becomes low. Accordingly, the reduced positive charges flow from the input terminal 311 to the piezoelectric device 3130. In this descriptions the right side and left side represent the directions on the drawings.

In the electrostatic system, when the position of the opposing electrode 3136 is moved to the left side, the amount of positive charges deposited on the surface of the opposing electrode 3136 increases and thus the deposited positive charges flow into the input terminal 3116 through the metal electrode substrate 3138. As a result, even in both cases of the "piezoelectric system" and the "electrostatic system", current 3184 flows from the right side to the left side in the resistor 3120. Since the positive charges are supplied from the left-side electrode of a capacitor element 3122-1, the left-side electrode is charged positively after the supply. Then, based upon the electromagnetic capacitor theory, the current 3148 flows into the right-side electrode of the capacitor element 3122-1 through a diode element 3126-1 to supply the positive charges. As another example, when the sensor device movable section 3102 moves to the left side, if no charges remain at both electrodes of the capacitor element 3122-1, the potentials of the electrodes become negative. Thus, it can also be said that the current 3184 flows toward the right-side electrode of the capacitor element 3122-1.

Figure 44:
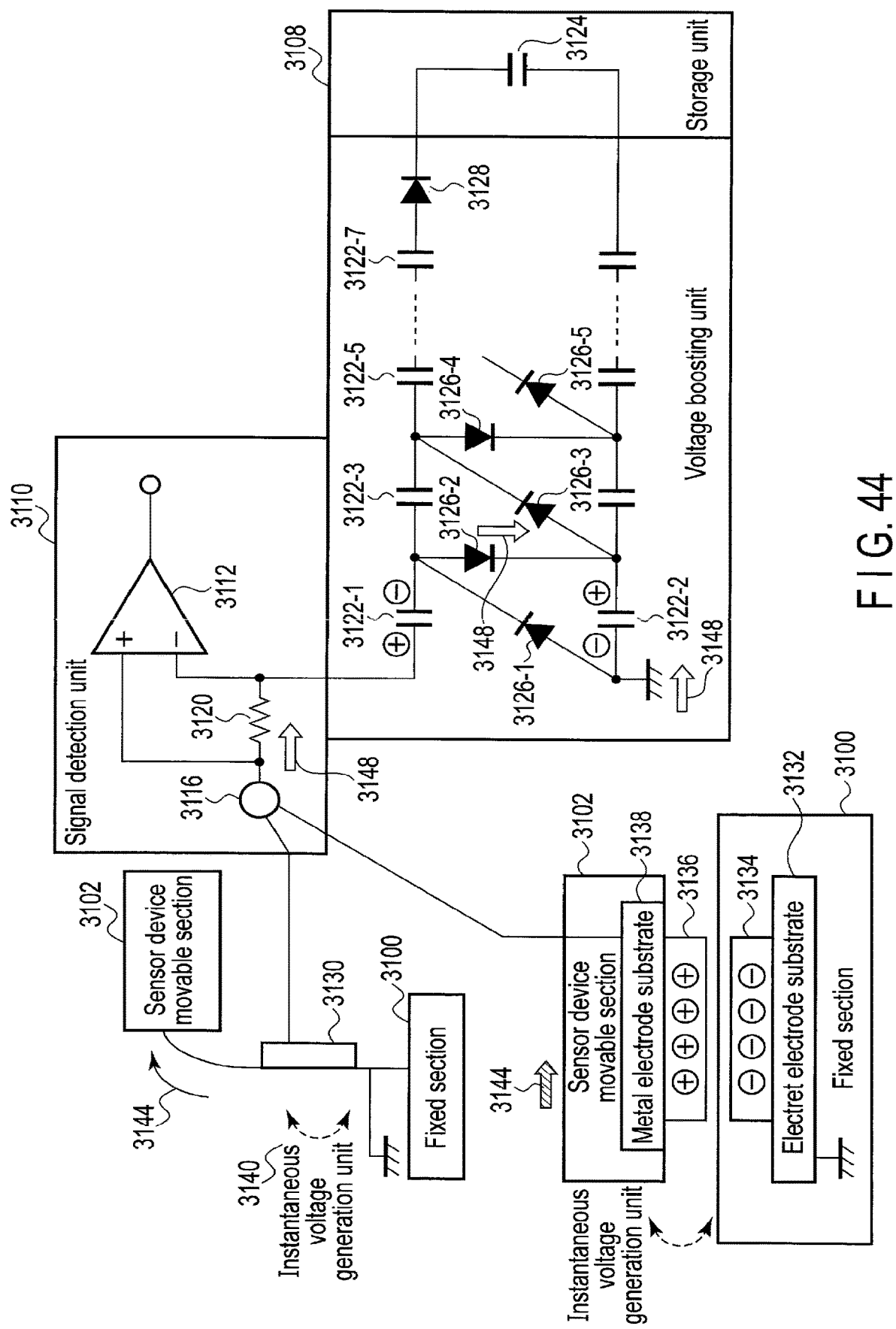
FIG. 44 is an illustration (2) of the principle of storage of the interior of the environmental vibration power-generating device.

When the sensor device movable section 3102 moves to the right side as shown in FIG. 44, the electromotive power increases at either end of the piezoelectric device 3130 and current flows from the left side to the right side in the resistor 3120 in the "piezoelectric system". In the "electrostatic system", the position of the opposing electrode 3136 is greatly displaced from that of the electret material 3134 and thus current flows from the left side to the right side in the resistor 3120 in order to reduce the amount of positive charges deposited on the surface of the opposing electrode 3136. At this time, the positive charges stored in the right-side electrode of the capacitor element 3122-1 move to the right-side electrode of a capacitor element 3122-2 through a diode element 3126-2. Then, negative charges are stored in the left-side electrode of the capacitor element 3122-2 to cancel the positive charges. As for this phenomenon, the following description can also be given. When the sensor device movable section 3102 moves to the right side, the potential of the right end of the resistor 3120 becomes positive. In the charge distribution in the capacitor element 3122-1 shown in FIG. 43, the potential of the right-side electrode of the capacitor element 3122-1 becomes very high and thus the current 3148 flows through the diode element 3126-2, Consequently, positive charges are stored in the right-side electrode of the capacitor element 3122-2 and negative charges are stored in the left-side electrode thereof.

After that, when the sensor device movable section 3102 returns to the left side as shown in FIG. 45, the current 3148 flows from the right side of the resistor 3120 to the left side thereof. If the charge distribution in either electrode of the capacitor element 3122-1 remains unchanged as shown in FIG. 44, the potential of the right-side electrode of the capacitor element 3122-1 becomes very low. As a result, the current 3148 flows toward the right-side electrode of the capacitor element 3122-1 through the diode element 3126-1 and positive charges are stored in the right-side electrode of the capacitor element 3122-1. At the same time, current flows into the instantaneous voltage generation unit 3104 from the left-side electrode of the capacitor element 3122-1 through the resistor 3120, with the result that negative charges are stored in the left-side electrode of the capacitor element 3122-1.

Figure 46:
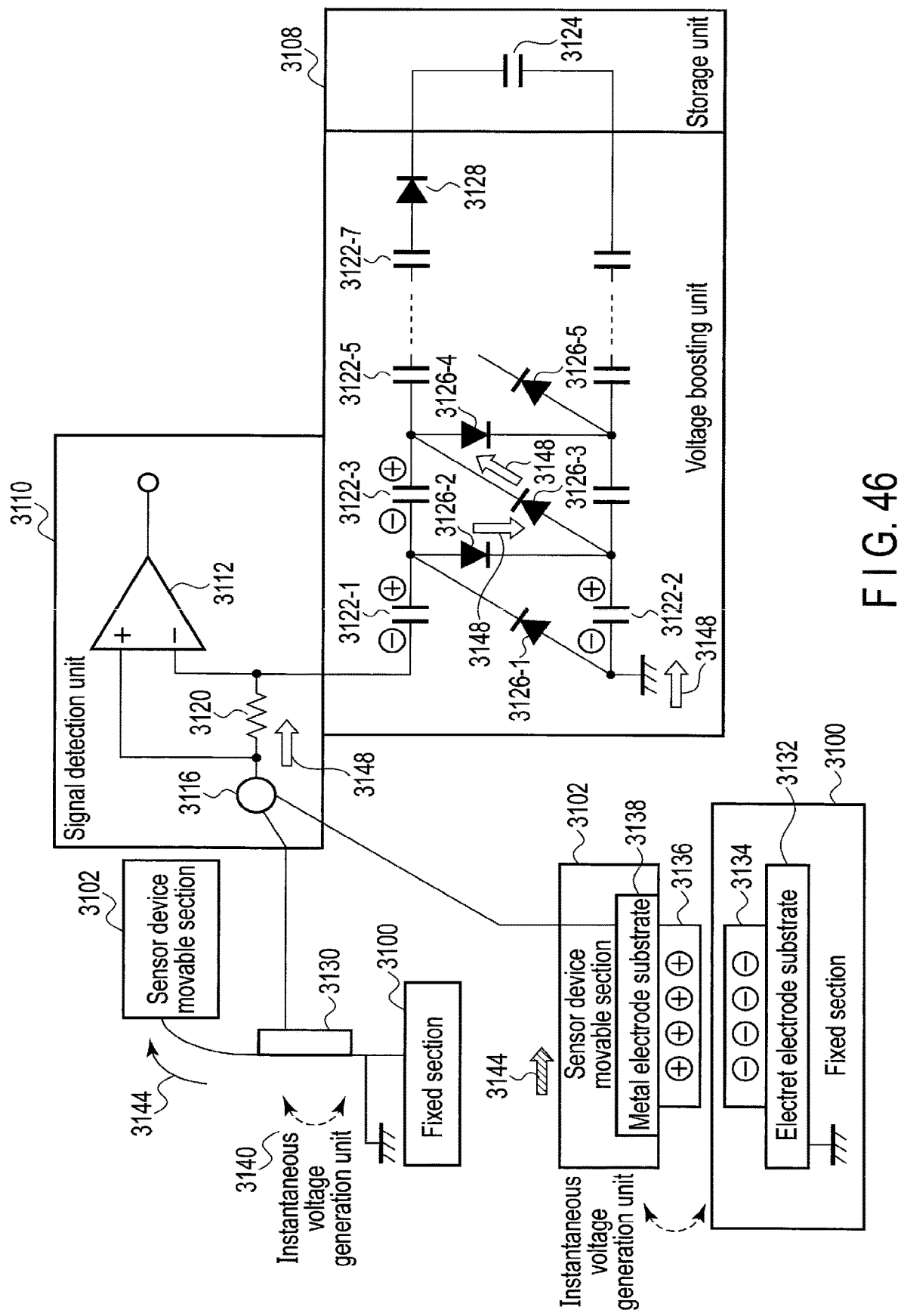
FIG. 46 is an illustration (4) of the principle of storage of the interior of the environmental vibration power-generating device.
Figure 47:
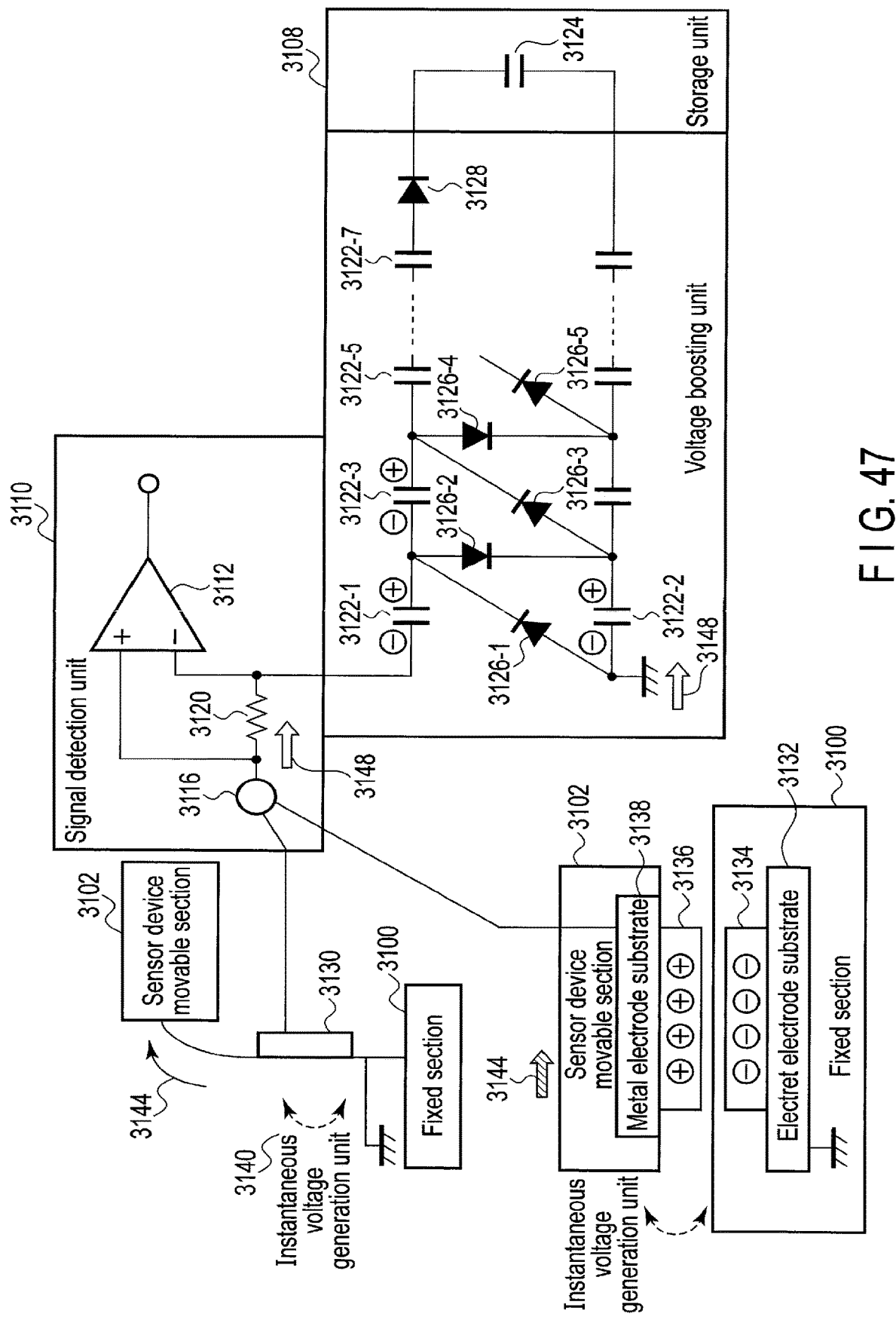
FIG. 47 is an illustration (5) of the principle of storage of the interior of the environmental vibration power-generating device.

FIG. 46 shows the sensor device movable section that has started to move toward the right side. It shows a momentary state in which the charge distribution in the electrodes at both ends of the capacitor element 3122-1 is held as shown in FIG. 45 when the current 3148 starts to flow from the left side of the resistor 3120 to the right side thereof at the start of the movement. Since, in this case, the potential of the right-side electrode of the capacitor element 3122 becomes very high, current starts to flow from the right-side electrode of the capacitor element 3122-1 to the right-side electrode of a capacitor element 3122-3 through diode elements 3126-2 and 3126-3. As a result, the charge distribution is generated in the electrodes at both ends of the capacitor element 3122-3 (voltages are generated/held at both ends of the capacitor element 3122-3) as shown in FIG. 47. The voltages are thus stored sequentially at both ends of the capacitor elements 3122-2 to 3122-8.

In the present embodiment, the interior of the sensor shown in FIG. 41 is so configured that the acceleration sensor unit or the angular velocity sensor unit 3006 and the environmental vibration generation device 3000 are disposed separately from each other. In contrast to this, as an application example of the present embodiment, both can be formed integrally as one unit. The basic structure in this case is shown in FIG. 48. If a section that generates an acceleration signal or an angular velocity signal and an environmental vibration generation section are formed integrally as one unit, the advantage capable of decreasing the total size of the sensors 2021 and 2022 is brought about.

In FIG. 48, the fixed section 3100 includes a plurality of instantaneous voltage generation units (1) 3104-1 to (n) 3104-*n*. Each of the instantaneous voltage generation units (1) 3104-1 to (n) 3104-*n* includes signal detection units (1) 3110-1 to (n) 3110-*n*. The detailed configuration of each of the instantaneous voltage generation units (1) 3104-1 to (n) 3104-*n* and that of each of the signal detection units (1) 3110-1 to (n) 3110-*n* may be the same as that of the instantaneous voltage generation unit 3104 and that of the signal detection unit 3110 described with reference to FIGS. 43 to 47. The present embodiment is not limited to this configuration, but another configuration can be employed if it has a function of fulfilling a similar function. Since the fixed section 3100 is disposed in common to the instantaneous voltage generation units (1) 3104-1 to (n) 3104-*n* (the fixed section 3100 is shared with the instantaneous voltage generation units, the advantage capable of decreasing the total size of the sensors 2021 and 2022 is brought about.

A signal computation unit 3200 computes a signal detected from each of the signal detection units (1) 3110-1 to (n) 3110-n to extract an acceleration signal and an angular velocity signal.

In parallel with the foregoing signal processing circuit, voltage boosting units (1) 3106-1 to (n) 3106-n are disposed to correspond to the instantaneous voltage generation units (1) 3104-1 to (n) 3104-n, respectively. The detailed configuration of the voltage boosting units (1) 3106-1 to (n) 3106-n may be the same as that of the voltage boosting unit 3106 described with reference to FIGS. 43 to 47. The present embodiment is not limited to this configuration, but another configuration can be employed if it has a function of fulfilling a similar function. The outputs of the voltage boosting units (1) 3106-1 to (n) 3106-n are synthesized by a synthesis unit 3210 and then connected to the storage unit 3108. In FIG. 48, the synthesis unit 3210 is configured to be connected electrically. As shown in FIGS. 43 to 47, the capacitor element 3128 is disposed immediately before the exit of each of the voltage boosting units (1) 3106-1 to (n) 3106-n in order to prevent a backflow and thus no problems occur though it is simply electrically connected as shown in FIG. 48. The present embodiment is not limited to this configuration. The powers can be synthesized by a sophisticated method.

Figure 49:
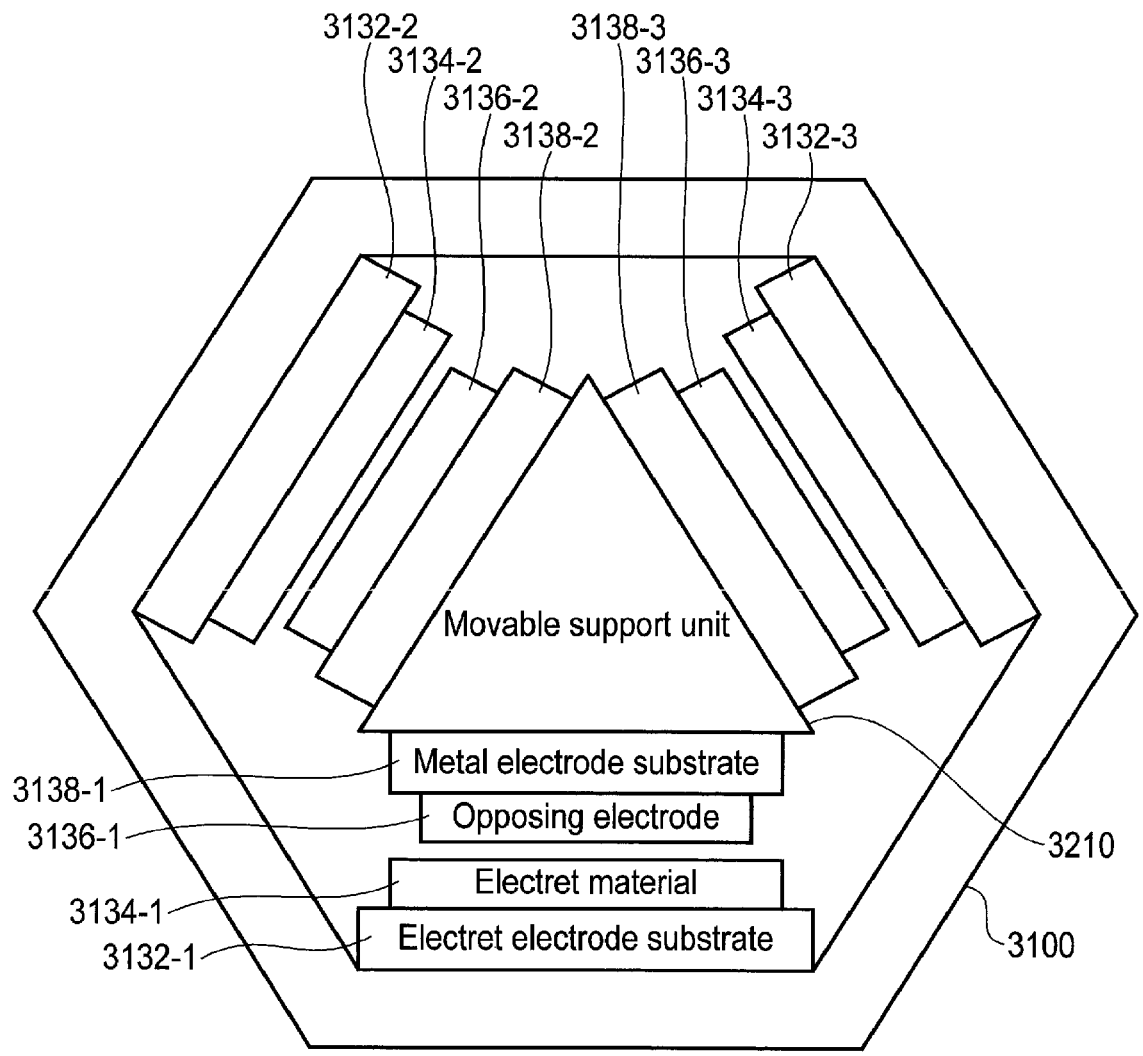
FIG. 49 is an illustration (1) of arrangement of a plurality of instantaneous voltage generators in the sensor device.

As a specific example of arrangement of the instantaneous voltage generation units (1) 3104-1 to (n) 3104-n shown in FIG. 48, an embodiment using, e.g., the "electrostatic system" will be described. FIG. 49 shows a one-way direction section arrangement. In the common fixed section 3100, electret electrode substrates (1) 3132-1 to (3) 3132-3 and electret materials (1) 3132-1 to (3) 3132-3 are laminated one on another.

In the center of the movable section, a triangular prism-shaped movable support unit 3210 is disposed movable relative to the fixed section 3100. The movable support unit 3210 can be moved in a direction orthogonal to the drawing of FIG. 49 (front-side direction and back-side direction). On the sides (rectangular surfaces) of the triangular prism of the movable support unit 3210, metal electrode substrates (1) 3138-1 to (3) 3138-3 and opposing electrodes (1) 3136-1 to (3) 3136-3 are disposed and all of them are synchronized and can be moved.

Figure 50:
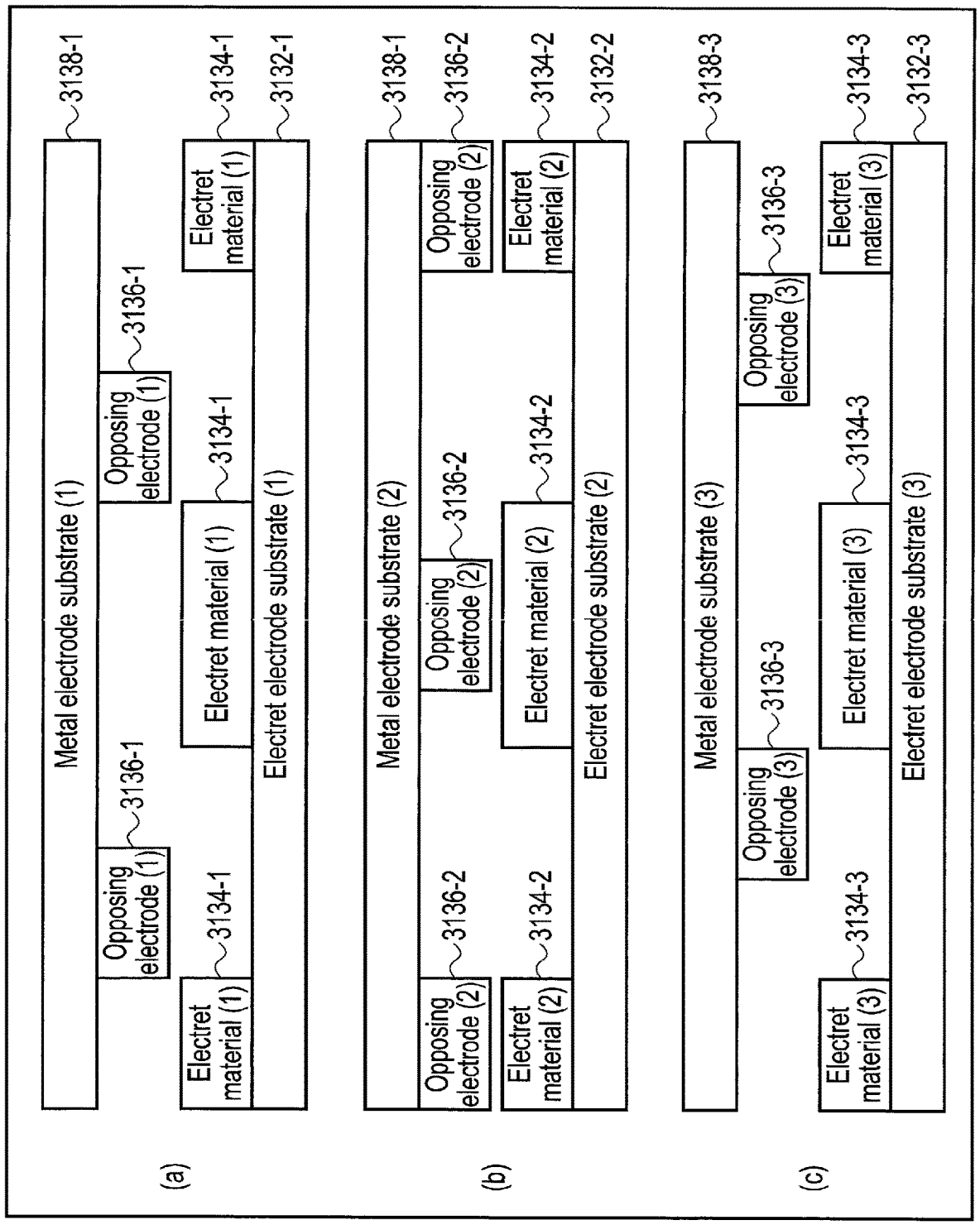
FIG. 50 is an illustration (2) of arrangement of a plurality of instantaneous voltage generators in the sensor device.

FIG. 50 shows a relationship in arrangement among the opposing electrodes (1) 3136-1 to (3) 3136-3 along the moving direction of the movable support unit 3210. The opposing electrodes (1) 3136-1 to (3) 3136-3 corresponding to the electret materials (1) 3134-1 to (3) 3134-3 are displaced from one another. This displacement brings about the advantage capable of detecting not only the absolute values of an acceleration amount and angular velocity but also the directions thereof simultaneously.

Consider the case where the metal electrode substrates (1) 3138-1 to (3) 3138-3 are simultaneously displaced horizontally based on the relationship in position shown in FIG. 50. In this case, the absolute value of negative charges deposited on the surface of the opposing electrode (2) 3136-2 decreases irrespective of the displacement direction. If the metal electrode substrates (1) 3138-1 to (3) 3138-3 are displaced at once to the right side, the absolute value of negative charges deposited on the surface of the opposing electrode (1) 3136-1 does not vary, but the absolute value of negative charges deposited on the surface of the opposing electrode (3) 3136-3 increases. If the metal electrode substrates (1) 3138-1 to (3) 3138-3 are displaced at once to the left side to the contrary, the absolute value of negative charges deposited on the surface of the opposing electrode (3) 3136-3 does not vary, but the absolute value of negative charges deposited on the surface of the opposing electrode (1) 3136-1 increases. From the strength and direction of current flowing toward the opposing electrodes (1) 3136-1 to (3) 3136-3 (the results of signal computation in the signal computation unit 3200), the moving direction and the moving speed variation of the metal electrode substrates (1) 3138-1 to (3) 3138-3 can be seen.

The present embodiment is not limited to the arrangement shown in FIG. 50 but can be directed to another arrangement. For example, the opposing electrodes (1) 3136-1 to (3) 3136-3 can be aligned with one another and instead the electret materials (1) 3134-1 to (3) 3134-3 can be displaced from one another.

The one-axis direction movement of the movable support unit 3210 has been described above. If the same principle is expanded, three-axis direction acceleration and three-axis angular velocity can be detected.

As is seen from the description given with reference to FIGS. 43 to 47, the environmental vibration generation device 3000 shown in FIG. 41 generates acceleration or angular velocity continuously to store voltages in the capacitor elements 3122-1 to 3122-8 gradually. Conversely, when neither acceleration nor angular velocity is generated for a long period of time, the power stored in the storage unit 3108 (in the capacitor element 3124 in the interior thereof (FIGS. 43 to 47)) is gradually discharged. Thus, when the environmental vibration generation device 3000 is in a stationary state for a long period of time, it becomes difficult to supply drive power to the acceleration sensor unit or the angular velocity sensor unit 3006, the short-range wireless communication unit 3004 and the control unit 3002. In the present embodiment utilizing this feature, acceleration or angular velocity is output with timing when it becomes low. This brings about the advantage capable of securing a stable supply of power from the environmental vibration generation device 3000 and detecting the changed acceleration or angular velocity with high accuracy.

While a worker is working, the sensors 2021 and 2022 is vibrating and rotating. Power of the environmental vibration generation device 3000 is thus stored in the interior of the sensors 2021 and 2022. When the worker's working is completed, the vibration and rotation of the sensors 2021 and 2022 is stopped, with the result that the edge device 42 is informed of the stoppage of vibration and rotation of the sensors 2021 and 2022 during a period in which the power storage amount of the environmental vibration generation device 3000 is secured.

The timing of change of the acceleration or angular velocity can be extracted by the control unit 3002 shown in FIG. 41 and so can be an acceleration value or an angular velocity value immediately after the extraction of the timing. A method for extracting the timing of change of the acceleration or angular velocity and an acceleration value or an angular velocity value immediately after the extraction of the timing will be described with reference to FIG. 51. The values of the acceleration or angular velocity obtained from the signal computation unit 3200 shown in FIG. 48 are input to the control unit 3002. The control unit 3002 includes a reference timing generation unit 3302 and processes an acceleration signal or an angular velocity signal transmitted from the signal computation unit 3200 each time reference timing is generated from the reference timing generation unit 3302.

As an index for detecting a variation in acceleration or angular velocity, in the angular velocity, an accumulated value of "angular velocity in a constant rotation direction" or an average value for each timing described above can be used. In the acceleration, the inversion of the acceleration direction is often repeated; thus, "an absolute value of acceleration" or "an amplitude value of a signal varying in the positive and negative directions" or the like can be calculated to compute an accumulated value or an average value for each timing described above. The present embodiment is not limited to this. An absolute value is computed and an amplitude value is calculated for the angular velocity, and an accumulated value and an average value can be calculated for the acceleration in consideration of the direction. These computations are performed by a calculation unit 3304 for calculating a power storage amount or an average value within a given period of time.

In the present embodiment, a calculated value and its subsequent calculated value are compared every predetermined timing in order to extract timing of change. In other words, the index obtained from the calculation unit 3304 for calculating a power storage amount or an average value within a given period of time, is stored temporarily in a calculation result temporal storage unit 3306 and compared with an index, which is obtained immediately after the former index from the calculation unit 3304, by a comparison unit 3308. When a result of the comparison exceeds a preset given value (including both the case where an index value is larger than the given value and the case where it is smaller than the given value), the comparison unit 3308 considers that the index value "has greatly varied" and outputs a voltage to (displays a flag on) a change timing notification terminal 3314. Thus, a point of switching between output values of the change timing notification terminal 3314 represents change timing. Simultaneously, an index value immediately after the change is output to a changed-value output terminal 3312.

In FIG. 51, the control unit is shown in the form of a block diagram of a circuit. The present embodiment is not limited to this. The foregoing processing method can be executed by programs/software to be executed by a processor.

Using the switching point timing of the output values of the change timing notification terminal 3314 as a trigger, the output values of the changed-value output terminal 3312 are communicated to the edge device 42 from the short-range wireless communication unit 3004 (FIG. 41).

The sensors 2021 and 2022 capable of detecting acceleration or angular velocity as described above can be used not only in the workplace described with reference to FIG. 40 but also in any other application fields. For example, they can be used in the infrastructure health market such as an automatic deterioration diagnosis of infrastructure under social infrastructure environment. Specifically, the sensors 2021 and 2022 used in the system according to the present embodiment can be used in a hammering test to inspect a partial deterioration of bridges and tunnels (a deteriorated portion is predicted from the pitch and tone of sound generated by hammering part of the infrastructure). In this case, it is bonded to the pillars, walls and ceilings of a bridge and a tunnel using the bonding section 3008 to be bonded to the existing environment and existing device. The vibration generated when a worker hammers a specific portion is sensed by the sensors 2021 and 2022 and the results of the vibration are collected by the edge device 42, with the result that a deterioration can be predicted.

In FIG. 52, (a) shows steps before and after a screwing operation. In other words, the vibration state before a worker approaches is a state of a normal period 3402. When the worker starts to tighten a screw, the normal period shifts to a screwing period 3404. when the screwing is completed, the screwing period shifts to a screwing completion period 3406.

In FIG. 52, (b) shows a measured acceleration value or a measured angular velocity value in the position of the screw 2001 in each step. In the normal period 3402 prior to the screwing operation, the vibration state is a normal state. In the screwing completion period 3406, too, the vibration state returns to the normal vibration state. As a result, the acceleration or angular velocity greatly changes at the instant when the normal period 3402 shifts to the screwing period 3404 and at the instant when the screwing period 3404 changes to the screwing completion period 3406.

The instant when the acceleration or angular velocity has greatly changed is extracted automatically and immediately afterward an acceleration value or an angular velocity value (or an amount of accumulation or an average during a predetermined period) is transmitted to the edge device 42 as the information described with reference to (c) of FIG. 52.

Figure 53:
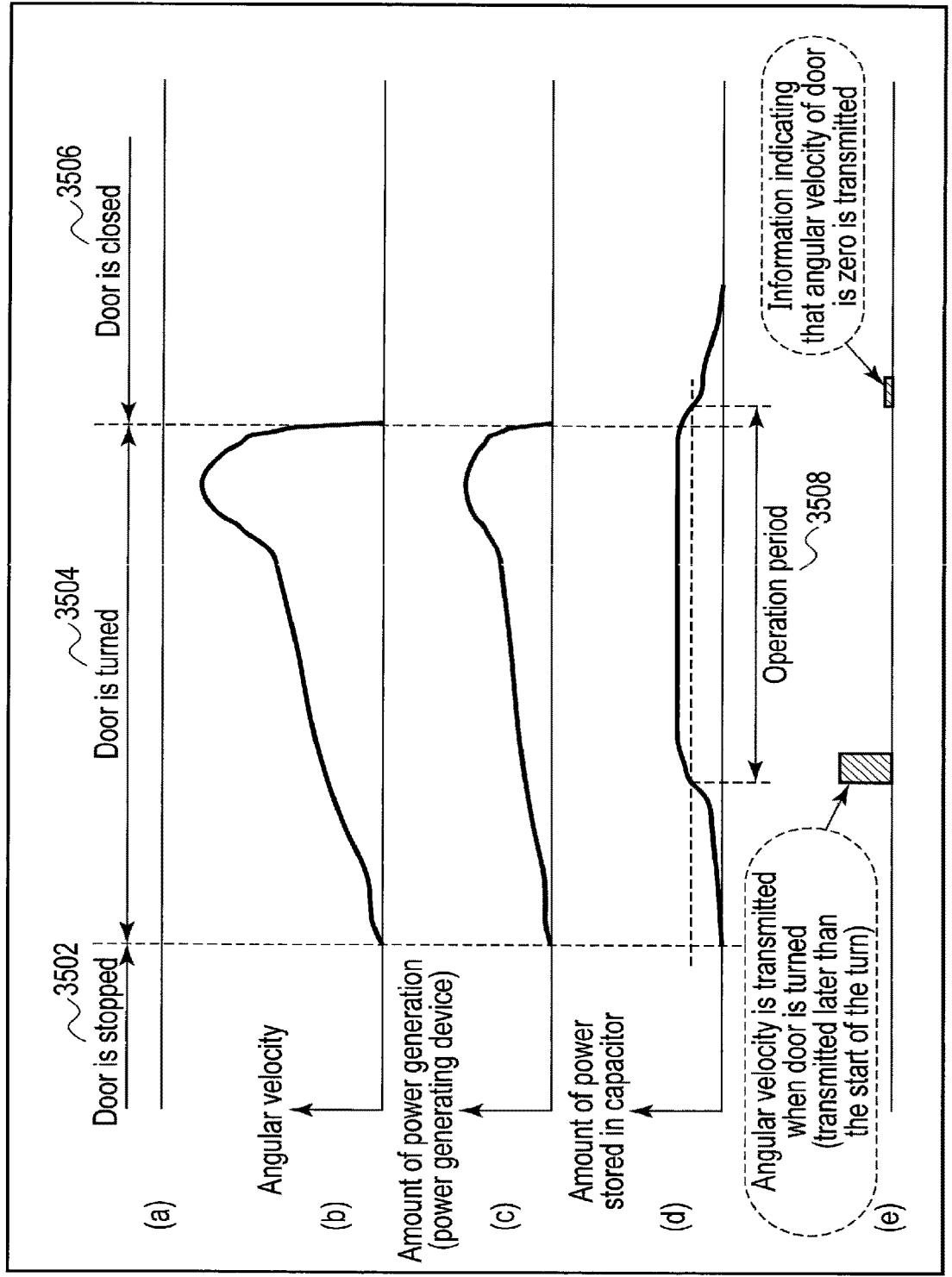
FIG. 53 is an illustration of a changed angular velocity state when a door is closed.

FIG. 53 shows a variation in angular velocity that is detected by the sensor 2022 attached to the door 2006 in the embodiment described with reference to FIG. 40 when the door 2006 is closed. As shown in (a) of FIG. 53, the timing can be divided into a time period during which the door is stopped 3502, a time period during which the door is turned 3504 and a time period during which the door is closed 3506. In FIG. 53, (b) shows a variation in angular velocity that is detected by the sensor 2022 attached to the door during each of the time periods. The value of angular velocity increases during the time period during which the door is turned 3504 and becomes the largest immediately before the door is closed. An example of the amount of power storage (amount of power generation) in the environmental vibration generation device 3000 (FIG. 41) is shown in (c) of FIG. 53. The environmental vibration generation device 3000 does not start to generate power (store power) before the door starts to turn. Only during the time period in which the amount of power storage exceeds a predetermined value corresponds to an operation period 3508 of the short-range wireless communication unit 3004 and the control unit 3002.

Short-range wireless communication can be carried out only during the operation period 3508. As shown in (e) of FIG. 53, therefore, communication information is transmitted to the edge device 42 later than the start of turn of the door. The point at which the time period during which the door is turned 3504 is switched to the time period during which the door is closed 3506 is included in the operation period 3508, information indicating that "the angular velocity of the door is zero" is communicated immediately after that point.

In the system according to the embodiment shown in FIG. 39A or 39B, when power is always stably supplied to sensors 2500 and 1152, short-range wireless communication can be carried out between the sensors 2500 and 1152 and the edge device 42 at any time. Thus, the timing of short-range wireless communication between the sensors 2500 and 1152 to which power can stably be supplied or the glasses 1100 and the edge device 42 is basically controlled by the edge device 42.

In contrast, the sensors 2021 and 2022 that receive power from the environmental vibration generation device 3000 is able to carry out short-range wireless communication only during the operation period 3508 as shown in (d) of FIG. 53. This timing cannot be predicted by the edge device 42. In the system according to the present embodiment, therefore, only the sensors 2021 and 2022 that receive power from the environmental vibration generation device 3000 is provided with the initiative of timing of the short-range wireless communication. This brings about the advantage capable of stable short-range wireless communication.

In this case, the timing of short-range wireless communication managed by the edge device 42 and the timing of short-range wireless communication performed voluntarily by the sensors 2021 and 2022 overlap each other to cause an unstable factor of short-range wireless communication. To resolve this problem, in the system according to the present embodiment, a wireless band (wireless reference frequency) of short-range wireless communication managed by the edge device 42 and a wireless band (wireless reference frequency) of short-range wireless communication performed voluntarily by the sensors 2021 and 2022 are separated from each other to prevent a cross talk therebetween. Thus, the short-range wireless communication managed by the edge device 42 can be stabilized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A behavior estimating method for estimating behavior of a person to be measured equipped with an activity meter including a signal processing unit that includes a battery, a three-axis acceleration sensor, a three-axis geomagnetism sensor, a signal amplifier group, an A/D converter, a controller, a memory, a communication controller, and a behavior estimation engine, the method comprising:
   amplifying three-axis-direction detected raw signals obtained from the three-axis acceleration sensor and the three-axis geomagnetism sensor;
   converting the three-axis-direction detected raw signals into digital signals;
   storing the digital signals in the memory;
   signal processing using the digital signals by the controller;
   wherein
   the signal processing includes:
   presetting a first angle between a gravitation direction and a direction of action when a first person with an average height handles an object to be operated;
   calculating the digital signals acquiring different acceleration waveforms, the digital signals being acquired when a second person being measured handles the object;
   extracting a second angle between the gravitation direction and the direction of action of the second person being measured from the different acceleration waveforms, wherein the gravitation direction is obtained instantaneously;
   performing a coordinate transformation process among the different acceleration waveforms based upon a difference of the preset first angle and the extracted second angle;
   sending a result of the coordinate transformation to the behavior estimation engine; and
   performing behavior estimation of the second person being measured using the result.

2. The behavior estimating method of claim 1, wherein a threshold value used for the behavior estimation is allowed to be changed depending upon the second angle.

3. The behavior estimating method of claim 1, wherein an extension/contraction matching technique is employed in at least part of the behavior estimation process.

4. A behavior estimating system comprising:
   a battery;
   a three-axis acceleration sensor;
   a three-axis geomagnetism sensor;
   a signal amplifier group;
   an A/D converter;
   a controller;
   a memory;
   a communication controller; and
   a behavior estimation engine; wherein:
   the three-axis acceleration sensor and the three-axis geomagnetism sensor generate three-axis-direction detected raw signals;
   the signal amplifier group amplifies the three-axis-direction detected raw signals;
   the A/D converter converts the three-axis-direction detected raw signals into digital signals;
   the memory stores the digital signals;
   the controller processes the digital signals;
   a first angle between a gravitation direction and a direction of action of a first person with an average height is preset when the first person handles an object to be operated;
   a second angle between the gravitation direction and the direction of action of a second person being measured is obtained when the second person handles the object, wherein the gravitation direction is obtained instantaneously;
   a difference between the first angle and the second angle is obtained, and the gravitation direction and the direction of action of the second person are coordinate transformed based on the difference of the first angle and the second angle;
   the result data of the coordinate transformation is sent to the behavior estimation engine; and
   behavior estimation of the second person is measured using the result data.

5. The behaver estimation system of claim 4, wherein the behavior estimation engine is provided in an edge device.

6. The behaver estimation system of claim 4, wherein the battery, the three-axis acceleration sensor, the three-axis geomagnetism sensor, the signal amplifier group, the A/D converter, the controller, the memory, and the communication controller are provided in a wrist band.

* * * * *